US009295737B2

(12) United States Patent
Bussat et al.

(10) Patent No.: US 9,295,737 B2
(45) Date of Patent: Mar. 29, 2016

(54) TARGETING VECTOR-PHOSPHOLIPID CONJUGATES

(71) Applicant: BRACCO SUISSE SA, Manno (CH)

(72) Inventors: Philippe Bussat, Pers-Jussy (FR); Samir Cherkaoui, Feigeres (FR); Hong (Helen) Fan, Shanghai (CN); Bernard Lamy, Saint-Julien-en-Genevois (FR); Palaniappa Nanjappan, Princeton, NJ (US); Radhakrishna K. Pillai, Cranbury, NJ (US); Sibylle Pochon, Troinex (CH); Bo Song, Princeton, NJ (US); Rolf E. Swenson, Princeton, NJ (US)

(73) Assignee: BRACCO SUISSE SA, Manno (CH)

( * ) Notice: Subject to any disclaimer, the term of this patent is extended or adjusted under 35 U.S.C. 154(b) by 214 days.

(21) Appl. No.: 14/190,860

(22) Filed: Feb. 26, 2014

(65) Prior Publication Data
US 2014/0206837 A1 Jul. 24, 2014

Related U.S. Application Data

(60) Continuation of application No. 12/257,552, filed on Oct. 24, 2008, now abandoned, which is a division of application No. 11/608,395, filed on Dec. 8, 2006, now Pat. No. 7,794,693.

(60) Provisional application No. 60/833,342, filed on Jul. 25, 2006, provisional application No. 60/749,240, filed on Dec. 9, 2005.

(51) Int. Cl.
*A61K 38/00* (2006.01)
*C07K 14/00* (2006.01)
*A61K 49/22* (2006.01)
*A61K 47/48* (2006.01)
*C07K 7/08* (2006.01)
*C07K 14/52* (2006.01)
*C07K 14/71* (2006.01)

(52) U.S. Cl.
CPC .......... *A61K 49/227* (2013.01); *A61K 47/48238* (2013.01); *A61K 49/223* (2013.01); *C07K 7/08* (2013.01); *C07K 14/001* (2013.01); *C07K 14/52* (2013.01); *C07K 14/71* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 2,913,451 A | 11/1959 | De La Mater et al. | |
| 4,093,709 A | 6/1978 | Choi et al. | |
| 4,131,648 A | 12/1978 | Choi et al. | |
| 4,138,344 A | 2/1979 | Choi et al. | |
| 4,180,646 A | 12/1979 | Choi et al. | |
| 4,391,797 A | 7/1983 | Folkman et al. | |
| 4,544,500 A | 10/1985 | Bittle et al. | |
| 4,718,433 A | 1/1988 | Feinstein | |
| 4,774,958 A | 10/1988 | Feinstein | |
| 4,844,882 A | 7/1989 | Widder et al. | |
| 4,899,755 A | 2/1990 | Lauffer et al. | |
| 4,900,540 A | 2/1990 | Ryan et al. | |
| 5,021,556 A | 6/1991 | Srinivasan | |
| 5,075,099 A | 12/1991 | Srinivasan et al. | |
| 5,118,797 A | 6/1992 | Jurisson et al. | |
| 5,123,414 A | 6/1992 | Unger | |
| 5,137,928 A | 8/1992 | Erbel et al. | |
| 5,180,816 A | 1/1993 | Dean | |
| 5,183,653 A | 2/1993 | Linder et al. | |
| 5,223,409 A | 6/1993 | Ladner et al. | |
| 5,230,882 A | 7/1993 | Unger | |
| 5,271,928 A | 12/1993 | Schneider et al. | |
| 5,316,921 A | 5/1994 | Godowski et al. | |
| 5,364,613 A | 11/1994 | Sieving et al. | |
| 5,367,080 A | 11/1994 | Toner et al. | |
| 5,380,519 A | 1/1995 | Schneider et al. | |
| 5,387,409 A | 2/1995 | Nunn et al. | |
| 5,413,774 A | 5/1995 | Schneider et al. | |
| 5,445,813 A | 8/1995 | Schneider et al. | |
| 5,469,854 A | 11/1995 | Unger et al. | |

(Continued)

FOREIGN PATENT DOCUMENTS

AU 2003213730 7/2003
AU 2003228276 9/2009

(Continued)

OTHER PUBLICATIONS

U.S. Appl. No. 14/109,508, filed Dec. 17, 2013.
Abandoned U.S. Appl. No. 10/661,156, filed Sep. 11, 2003.
Abandoned U.S. Appl. No. 10/939,890, filed Sep. 13, 2004.
Abandoned U.S. Appl. No. 12/257,552, filed Oct. 24, 2008.
Abandoned U.S. Appl. No. 13/160,666, filed Jun. 15, 2011.
U.S. Appl. No. 14/031,562, filed Sep. 19, 2013.
Office Action of Canadian Application No. 2,666,005 dated Jun. 11, 2014.
Office Action of Japanese Application No. 2013-025796 dated Jul. 18, 2014.

(Continued)

*Primary Examiner* — Anand Desai
(74) *Attorney, Agent, or Firm* — Pearl Cohen Zedek Latzer Baratz LLP

(57) ABSTRACT

Peptide vectors having high KDR binding affinity and processes for making such vectors are provided. The peptide vectors may be conjugated to phospholipids and included in ultrasound contrast agent compositions. Such ultrasound contrast agents are particularly useful in therapeutic and diagnostic methods, such as in imaging KDR-containing tissue and in the evaluation and treatment of angiogenic processes associated with neoplastic conditions. The present invention also provides processes for the large scale production of highly pure dimeric and monomeric peptide phospholipid conjugates as well as precursor materials used to form the conjugates. The present invention further provides processes for the large scale production of highly pure peptide phospholipid conjugates which contain very low levels of TFA.

6 Claims, 11 Drawing Sheets

(56) References Cited

U.S. PATENT DOCUMENTS

| | | |
|---|---|---|
| 5,474,756 A | 12/1995 | Tweedle et al. |
| 5,529,766 A | 6/1996 | Klaveness et al. |
| 5,531,980 A | 7/1996 | Schneider et al. |
| 5,536,490 A | 7/1996 | Klaveness et al. |
| 5,547,656 A | 8/1996 | Unger |
| 5,547,856 A | 8/1996 | Godowski et al. |
| 5,556,610 A | 9/1996 | Yan et al. |
| 5,556,939 A | 9/1996 | Flanagan et al. |
| 5,558,856 A | 9/1996 | Klaveness et al. |
| 5,558,857 A | 9/1996 | Klaveness et al. |
| 5,567,414 A | 10/1996 | Schneider et al. |
| 5,578,292 A | 11/1996 | Schneider et al. |
| 5,580,563 A | 12/1996 | Tam |
| 5,585,112 A | 12/1996 | Unger et al. |
| 5,597,549 A | 1/1997 | Schneider et al. |
| 5,607,661 A | 3/1997 | Berg et al. |
| 5,608,110 A | 3/1997 | Ramalingam et al. |
| 5,627,286 A | 5/1997 | Ramalingam et al. |
| 5,637,289 A | 6/1997 | Klaveness et al. |
| 5,643,553 A | 7/1997 | Schneider et al. |
| 5,656,254 A | 8/1997 | Ramalingam et al. |
| 5,658,551 A | 8/1997 | Schneider et al. |
| 5,662,885 A | 9/1997 | Pollak et al. |
| 5,665,329 A | 9/1997 | Ramalingam et al. |
| 5,670,133 A | 9/1997 | Zamora |
| 5,686,060 A | 11/1997 | Schneider et al. |
| 5,686,292 A | 11/1997 | Schwall et al. |
| 5,688,487 A | 11/1997 | Linder et al. |
| 5,707,624 A | 1/1998 | Nickoloff et al. |
| 5,711,933 A | 1/1998 | Bichon et al. |
| 5,720,934 A | 2/1998 | Dean et al. |
| 5,723,584 A | 3/1998 | Schatz |
| 5,759,515 A | 6/1998 | Rhodes et al. |
| 5,759,996 A | 6/1998 | Cheng et al. |
| 5,766,860 A | 6/1998 | Terman et al. |
| 5,769,080 A | 6/1998 | Unger et al. |
| 5,770,421 A | 6/1998 | Morris et al. |
| 5,773,024 A | 6/1998 | Unger et al. |
| 5,773,412 A | 6/1998 | Cheng et al. |
| 5,780,006 A | 7/1998 | Pollak et al. |
| 5,798,091 A | 8/1998 | Trevino et al. |
| 5,840,275 A | 11/1998 | Bichon et al. |
| 5,846,518 A | 12/1998 | Yan et al. |
| 5,846,519 A | 12/1998 | Tweedle et al. |
| 5,849,261 A | 12/1998 | Dean et al. |
| 5,851,999 A | 12/1998 | Ulrich et al. |
| 5,855,866 A | 1/1999 | Thorpe et al. |
| 5,861,301 A | 1/1999 | Terman et al. |
| 5,863,520 A | 1/1999 | Bichon et al. |
| 5,871,959 A | 2/1999 | Rong et al. |
| 5,876,973 A | 3/1999 | Marchionni |
| 5,877,289 A | 3/1999 | Thorpe et al. |
| 5,879,658 A | 3/1999 | Dean et al. |
| 5,885,866 A | 3/1999 | Chen |
| 5,886,142 A | 3/1999 | Thakur et al. |
| 5,908,610 A | 6/1999 | Schneider et al. |
| 5,911,972 A | 6/1999 | Schneider et al. |
| 5,935,820 A | 8/1999 | Hu et al. |
| 5,942,385 A | 8/1999 | Hirth |
| 5,976,495 A | 11/1999 | Pollak et al. |
| 5,990,263 A | 11/1999 | Dugstad et al. |
| 6,025,331 A | 2/2000 | Moses et al. |
| 6,033,645 A | 3/2000 | Unger et al. |
| 6,040,157 A | 3/2000 | Hu et al. |
| 6,051,230 A | 4/2000 | Thorpe et al. |
| 6,057,428 A | 5/2000 | Keyt et al. |
| 6,071,495 A | 6/2000 | Unger et al. |
| 6,071,532 A | 6/2000 | Chaikof et al. |
| 6,093,382 A | 7/2000 | Wedeking et al. |
| 6,110,433 A | 8/2000 | Kleinsorgen et al. |
| 6,110,443 A | 8/2000 | Schneider et al. |
| 6,123,922 A | 9/2000 | Bichon et al. |
| 6,130,071 A | 10/2000 | Alitalo et al. |
| 6,136,293 A | 10/2000 | Schneider et al. |
| 6,143,274 A | 11/2000 | Tweedle et al. |
| 6,146,657 A | 11/2000 | Unger et al. |
| 6,165,458 A | 12/2000 | Foldvari et al. |
| 6,171,614 B1 | 1/2001 | Chaikof et al. |
| 6,183,725 B1 | 2/2001 | Yan et al. |
| 6,187,288 B1 | 2/2001 | Schneider et al. |
| 6,200,548 B1 | 3/2001 | Bichon et al. |
| 6,204,011 B1 | 3/2001 | Kendall et al. |
| 6,207,152 B1 | 3/2001 | Schwall et al. |
| 6,221,839 B1 | 4/2001 | Alitalo et al. |
| 6,231,834 B1 | 5/2001 | Unger et al. |
| 6,245,318 B1 | 6/2001 | Klibanov et al. |
| 6,245,530 B1 | 6/2001 | Alitalo et al. |
| 6,258,378 B1 | 7/2001 | Schneider et al. |
| 6,261,535 B1 | 7/2001 | Thorpe et al. |
| 6,261,537 B1 | 7/2001 | Klaveness et al. |
| 6,264,917 B1 | 7/2001 | Klaveness et al. |
| 6,274,166 B1 | 8/2001 | Sintov et al. |
| 6,312,661 B1 | 11/2001 | Reubi |
| 6,312,665 B1 | 11/2001 | Modi |
| 6,322,770 B1 | 11/2001 | Rajopadhye et al. |
| 6,331,289 B1 | 12/2001 | Klaveness et al. |
| 6,359,115 B1 | 3/2002 | Kendall et al. |
| 6,361,946 B1 | 3/2002 | Alitalo et al. |
| 6,403,088 B1 | 6/2002 | Alitalo et al. |
| 6,451,764 B1 | 9/2002 | Lee et al. |
| 6,521,211 B1 | 2/2003 | Unger et al. |
| 6,524,533 B1 | 2/2003 | Tyrrell |
| 6,528,039 B2 | 3/2003 | Unger |
| 6,537,520 B1 | 3/2003 | Rajopadhye et al. |
| 6,548,048 B1 | 4/2003 | Cuthbertson et al. |
| 6,548,663 B1 | 4/2003 | Cheesman et al. |
| 6,576,608 B1 | 6/2003 | Lee et al. |
| 6,610,269 B1 | 8/2003 | Klaveness et al. |
| 6,645,933 B1 | 11/2003 | Alitalo et al. |
| 6,680,047 B2 | 1/2004 | Klaveness et al. |
| 6,689,352 B2 | 2/2004 | Achen et al. |
| 6,710,165 B2 | 3/2004 | Lee et al. |
| 6,730,658 B1 | 5/2004 | Alitalo et al. |
| 6,733,755 B2 | 5/2004 | Tchistiakova et al. |
| 6,773,696 B2 | 8/2004 | Unger |
| 6,777,534 B1 | 8/2004 | Klagsbrun et al. |
| 6,800,273 B2 | 10/2004 | Rajopadhye et al. |
| 6,818,220 B1 | 11/2004 | Alitalo et al. |
| 6,841,367 B1 | 1/2005 | Kendall et al. |
| 6,841,382 B2 | 1/2005 | Kendall et al. |
| 6,875,741 B2 | 4/2005 | Pillutla et al. |
| 6,984,373 B2 | 1/2006 | Wescott et al. |
| 7,034,105 B2 | 4/2006 | Alitalo et al. |
| 7,078,015 B2 | 7/2006 | Unger |
| 7,199,100 B2 | 4/2007 | Betz et al. |
| 7,211,240 B2 | 5/2007 | Arbogast et al. |
| 7,261,876 B2 | 8/2007 | Arbogast et al. |
| 7,666,979 B2 | 2/2010 | Fan et al. |
| 7,794,693 B2 | 9/2010 | Bussat et al. |
| 7,854,919 B2 | 12/2010 | Arbogast et al. |
| 7,910,088 B2 | 3/2011 | Arbogast et al. |
| 7,985,402 B2 | 7/2011 | Bussat et al. |
| 8,551,450 B2 | 10/2013 | Bussat et al. |
| 8,623,822 B2 | 1/2014 | Arbogast et al. |
| 8,632,753 B2 | 1/2014 | Fan et al. |
| 8,642,010 B2 | 2/2014 | Sato et al. |
| 8,663,603 B2 | 3/2014 | Arbogast et al. |
| 2001/0031485 A1 | 10/2001 | Backer et al. |
| 2001/0038842 A1 | 11/2001 | Achen et al. |
| 2002/0001566 A1 | 1/2002 | Rajopadhye et al. |
| 2002/0010137 A1 | 1/2002 | Ashkenazi et al. |
| 2002/0015680 A1 | 2/2002 | Harris |
| 2002/0037289 A1 | 3/2002 | Thorpe et al. |
| 2002/0058619 A1 | 5/2002 | Tchistiakova et al. |
| 2002/0065218 A1 | 5/2002 | Achen et al. |
| 2002/0068697 A1 | 6/2002 | Tournaire et al. |
| 2002/0086013 A1 | 7/2002 | King |
| 2002/0091082 A1 | 7/2002 | Aiello |
| 2002/0098187 A1 | 7/2002 | Ferrera et al. |
| 2002/0102215 A1 | 8/2002 | Klaveness et al. |
| 2002/0102217 A1 | 8/2002 | Klaveness et al. |
| 2002/0102260 A1 | 8/2002 | Achen et al. |
| 2002/0119149 A1 | 8/2002 | Jakobsen et al. |
| 2002/0136721 A1 | 9/2002 | Schwall et al. |

(56) References Cited

U.S. PATENT DOCUMENTS

| | | | |
|---|---|---|---|
| 2002/0164667 A1 | 11/2002 | Alitalo et al. |
| 2003/0023046 A1 | 1/2003 | Ferrara et al. |
| 2003/0027246 A1 | 2/2003 | Pedyczak et al. |
| 2003/0055006 A1 | 3/2003 | Siemeister et al. |
| 2003/0082103 A1 | 5/2003 | Wartchow et al. |
| 2003/0091567 A1 | 5/2003 | Alitalo et al. |
| 2003/0124120 A1 | 7/2003 | Harris |
| 2003/0125493 A1 | 7/2003 | Harris et al. |
| 2003/0129223 A1 | 7/2003 | Wartchow et al. |
| 2003/0149262 A1 | 8/2003 | Cheesman et al. |
| 2003/0157025 A1 | 8/2003 | Unger et al. |
| 2003/0166523 A1 | 9/2003 | Achen et al. |
| 2003/0166873 A1 | 9/2003 | Lee et al. |
| 2003/0176674 A1 | 9/2003 | Rosen et al. |
| 2003/0180305 A1 | 9/2003 | Rajopadhye et al. |
| 2003/0180718 A1 | 9/2003 | Pillutla et al. |
| 2003/0195147 A1 | 10/2003 | Pillutla et al. |
| 2003/0236190 A1 | 12/2003 | Pillutla et al. |
| 2004/0009122 A1 | 1/2004 | Klaveness et al. |
| 2004/0018974 A1 | 1/2004 | Arbogast et al. |
| 2004/0023887 A1 | 2/2004 | Pillutla et al. |
| 2004/0033949 A1 | 2/2004 | Bunting et al. |
| 2004/0037820 A1 | 2/2004 | Alitalo et al. |
| 2004/0141922 A1 | 7/2004 | Klaveness et al. |
| 2004/0147448 A1 | 7/2004 | Alitalo et al. |
| 2004/0147449 A1 | 7/2004 | Siemeister et al. |
| 2004/0147726 A1 | 7/2004 | Alitalo et al. |
| 2004/0213790 A1 | 10/2004 | Lee et al. |
| 2004/0223911 A1 | 11/2004 | Bednarski et al. |
| 2004/0224398 A1 | 11/2004 | Anand-Apte |
| 2004/0248781 A1 | 12/2004 | Kerbel |
| 2004/0266694 A1 | 12/2004 | Tchistiakova et al. |
| 2005/0002865 A1 | 1/2005 | Klaveness et al. |
| 2005/0037967 A1 | 2/2005 | Rosenblum |
| 2005/0100963 A1 | 5/2005 | Sato et al. |
| 2005/0147555 A1 | 7/2005 | Fan et al. |
| 2005/0181995 A1 | 8/2005 | Kawai et al. |
| 2005/0214859 A1 | 9/2005 | Dransfield et al. |
| 2005/0250700 A1 | 11/2005 | Sato et al. |
| 2006/0003926 A1 | 1/2006 | Rajopadhye et al. |
| 2006/0008930 A1 | 1/2006 | Toyoda et al. |
| 2006/0063699 A1 | 3/2006 | Larsen |
| 2006/0078501 A1 | 4/2006 | Goertz et al. |
| 2006/0089307 A1 | 4/2006 | Kulseth |
| 2007/0172428 A1 | 7/2007 | Arbogast et al. |
| 2007/0243139 A1 | 10/2007 | Arbogast et al. |
| 2008/0152594 A1 | 6/2008 | Bussat et al. |
| 2009/0131636 A1 | 5/2009 | Bussat et al. |
| 2011/0286936 A1 | 11/2011 | Bussat et al. |
| 2013/0266519 A1 | 10/2013 | Bussat et al. |
| 2014/0031520 A1 | 1/2014 | Bussat et al. |
| 2014/0161732 A1 | 6/2014 | Arbogast et al. |

FOREIGN PATENT DOCUMENTS

| | | |
|---|---|---|
| CA | 2477935 | 10/2003 |
| CA | 2631716 | 6/2007 |
| EP | 0122624 | 10/1984 |
| EP | 0123235 | 10/1984 |
| EP | 0324938 | 7/1989 |
| EP | 0365467 | 4/1990 |
| EP | 0458745 | 11/1991 |
| EP | 0474833 | 3/1992 |
| EP | 0536350 | 4/1993 |
| EP | 0554213 | 8/1993 |
| EP | 0580726 | 2/1994 |
| EP | 0619743 | 10/1994 |
| EP | 0627940 | 12/1994 |
| EP | 0666868 | 8/1995 |
| EP | 0682530 | 11/1995 |
| EP | 0711127 | 5/1996 |
| EP | 0744962 | 12/1996 |
| EP | 0804932 | 11/1997 |
| EP | 0831932 | 4/1998 |
| EP | 0842273 | 5/1998 |
| EP | 0848755 | 6/1998 |
| EP | 0881915 | 12/1998 |
| EP | 0977600 | 2/2000 |
| EP | 1007101 | 6/2000 |
| EP | 1064376 | 1/2001 |
| EP | 1068224 | 1/2001 |
| EP | 1081913 | 3/2001 |
| EP | 1166798 | 1/2002 |
| EP | 1166799 | 1/2002 |
| EP | 1238986 | 9/2002 |
| EP | 1261370 | 12/2002 |
| EP | 1268760 | 1/2003 |
| EP | 1278771 | 1/2003 |
| EP | 1292335 | 3/2003 |
| EP | 1306095 | 5/2003 |
| EP | 03002373 | 8/2003 |
| EP | 1432433 | 6/2004 |
| EP | 1444991 | 8/2004 |
| EP | 1259248 | 12/2004 |
| EP | 1519193 | 3/2005 |
| EP | 1574518 | 9/2005 |
| EP | 1586333 | 10/2005 |
| EP | 1966388 | 9/2008 |
| EP | 2014310 | 1/2009 |
| EP | 2301587 | 3/2011 |
| EP | 2359864 | 8/2011 |
| JP | 94-41458 | 2/1994 |
| JP | 07300452 A2 | 11/1995 |
| JP | 11-506327 | 6/1999 |
| JP | A-11-507638 | 7/1999 |
| JP | 2002-330772 | 11/2002 |
| JP | 3398382 | 2/2003 |
| JP | 2004-500854 | 1/2004 |
| JP | 2009-518448 | 5/2009 |
| WO | WO 86/06605 | 11/1986 |
| WO | WO 91/03200 | 3/1991 |
| WO | WO 92/14748 | 9/1992 |
| WO | WO 93/13809 | 7/1993 |
| WO | WO 94/00144 | 1/1994 |
| WO | WO 94/10202 | 5/1994 |
| WO | WO 95/01187 | 1/1995 |
| WO | WO 95/03280 | 2/1995 |
| WO | WO 95/06633 | 3/1995 |
| WO | WO 95/21631 | 8/1995 |
| WO | WO 95/28179 | 10/1995 |
| WO | WO 95/28967 | 11/1995 |
| WO | WO 96/03427 | 2/1996 |
| WO | WO 96/15815 | 5/1996 |
| WO | WO 96/17628 | 6/1996 |
| WO | WO 96/23524 | 8/1996 |
| WO | WO 96/23525 | 8/1996 |
| WO | WO 96/23526 | 8/1996 |
| WO | WO 96/38557 | 12/1996 |
| WO | WO 96/40285 | 12/1996 |
| WO | WO 97/05250 | 2/1997 |
| WO | WO 97/09427 | 3/1997 |
| WO | WO 97/17442 | 5/1997 |
| WO | WO 97/18841 | 5/1997 |
| WO | WO 97/29783 | 8/1997 |
| WO | WO 97/36619 | 10/1997 |
| WO | WO 98/05364 | 2/1998 |
| WO | WO 98/16198 | 4/1998 |
| WO | WO 98/17324 | 4/1998 |
| WO | WO 98/18495 | 5/1998 |
| WO | WO 98/18496 | 5/1998 |
| WO | WO 98/18497 | 5/1998 |
| WO | WO 98/18498 | 5/1998 |
| WO | WO 98/18500 | 5/1998 |
| WO | WO 98/18501 | 5/1998 |
| WO | WO 98/28179 | 7/1998 |
| WO | WO 98/33917 | 8/1998 |
| WO | WO 98/46612 | 10/1998 |
| WO | WO 98/47538 | 10/1998 |
| WO | WO 98/47541 | 10/1998 |
| WO | WO 98/52618 | 11/1998 |
| WO | WO 98/53051 | 11/1998 |
| WO | WO 98/53857 | 12/1998 |
| WO | WO 98/57666 | 12/1998 |

(56) References Cited

FOREIGN PATENT DOCUMENTS

| | | |
|---|---|---|
| WO | WO 98/58053 | 12/1998 |
| WO | WO 99/17809 | 4/1999 |
| WO | WO 99/29861 | 6/1999 |
| WO | WO 99/40102 | 8/1999 |
| WO | WO 99/40947 | 8/1999 |
| WO | WO 99/55383 | 11/1999 |
| WO | WO 99/58162 | 11/1999 |
| WO | WO 99/64052 | 12/1999 |
| WO | WO 00/20027 | 4/2000 |
| WO | WO 00/27414 | 5/2000 |
| WO | WO 00/44777 | 8/2000 |
| WO | WO 00/45856 | 8/2000 |
| WO | WO 00/63380 | 10/2000 |
| WO | WO 00/75167 | 12/2000 |
| WO | WO 01/16135 | 3/2001 |
| WO | WO 01/42284 | 6/2001 |
| WO | WO 01/52875 | 7/2001 |
| WO | WO 01/54723 | 8/2001 |
| WO | WO 01/57067 | 8/2001 |
| WO | WO 01/62942 | 8/2001 |
| WO | WO 01/64235 | 9/2001 |
| WO | WO 01/70268 | 9/2001 |
| WO | WO 01/70681 | 9/2001 |
| WO | WO 01/70945 | 9/2001 |
| WO | WO 01/72829 | 10/2001 |
| WO | WO 01/79479 | 10/2001 |
| WO | WO 01/82870 | 11/2001 |
| WO | WO 01/83693 | 11/2001 |
| WO | WO 01/91805 | 12/2001 |
| WO | WO 01/93836 | 12/2001 |
| WO | WO 01/97850 | 12/2001 |
| WO | WO 01/97860 | 12/2001 |
| WO | WO 02/06789 | 1/2002 |
| WO | WO 02/07747 | 1/2002 |
| WO | WO 02/16412 | 2/2002 |
| WO | WO 02/28895 | 4/2002 |
| WO | WO 02/057299 | 7/2002 |
| WO | WO 02/060950 | 8/2002 |
| WO | WO 02/072011 | 9/2002 |
| WO | WO 02/083849 | 10/2002 |
| WO | WO 02/092573 | 11/2002 |
| WO | WO 02/096367 | 12/2002 |
| WO | WO 03/000842 | 1/2003 |
| WO | WO 03/000844 | 1/2003 |
| WO | WO 03/018797 | 3/2003 |
| WO | WO 03/027246 | 4/2003 |
| WO | WO 03/028643 | 4/2003 |
| WO | WO 03/035839 | 5/2003 |
| WO | WO 03/070747 | 8/2003 |
| WO | WO 03/074005 | 9/2003 |
| WO | WO 03/080653 | 10/2003 |
| WO | WO 03/084574 | 10/2003 |
| WO | WO 03/094617 | 11/2003 |
| WO | WO 03/103581 | 12/2003 |
| WO | WO 04/001064 | 12/2003 |
| WO | WO 2004/033949 | 4/2004 |
| WO | WO 2004/058802 | 7/2004 |
| WO | WO 2004/058803 | 7/2004 |
| WO | WO 2004/064595 | 8/2004 |
| WO | WO 2004/065621 | 8/2004 |
| WO | WO 2004/069284 | 8/2004 |
| WO | WO 2004/078778 | 9/2004 |
| WO | WO 2004/085617 | 10/2004 |
| WO | WO 2004/0108074 | 12/2004 |
| WO | WO 2005/011722 | 2/2005 |
| WO | WO 2005/016963 | 2/2005 |
| WO | WO 2005/037862 | 4/2005 |
| WO | WO 2005/070472 | 8/2005 |
| WO | WO 2005/072417 | 8/2005 |
| WO | WO 2006/015385 | 2/2006 |
| WO | WO 2007/067979 | 6/2007 |
| WO | WO2007067979 | 6/2007 |

OTHER PUBLICATIONS

Office Action Issued for U.S. Appl. No. 14/031,562, dated Sep. 26, 2014.
Canadian Office Action issued for Canadian Application No. 2,826,960, dated Feb. 5, 2015.
Korean Office Action issued for Korean Patent Application No. 10-2014-7014542, dated Feb. 10, 2015.
Canadian Office Action issued for Canadian Application No. 2,666,005, dated Feb. 23, 2015.
Final Office Action issued in Korean Patent Application No. 10-2013-7021393, dated Apr. 29, 2014, and an English translation thereof.
Office Action issued in Chinese Patent Application No. 2013-10052906.3, dated Mar. 21, 2014, and an English translation thereof.
U.S. Appl. No. 60/360,851, filed Mar. 1, 2002, Sato et al.
U.S. Appl. No. 60/440,201, filed Jan. 15, 2003, Marinelli et al.
U.S. Appl. No. 60/440,411, filed Jan. 15, 2003, Sato et al.
U.S. Appl. No. 60/451,588, filed Mar. 3, 2003, Dransfield et al.
Adams, "Insight into Tyrosine Phosphorylation in v-Fps using Proton Inventory Techniques," Biochemistry. Aug. 20, 1996:35(33):10949-56.
Alberico et al., "Preparation and handling of peptides containing methionine and cysteine," Fmoc Solid Phase Peptide Synthesis—A Practical Approach (Chan, W. C. and White, P. D. Eds.) Oxford University Press, New York, N.Y. Chap. 4, pp. 87-114 (2000).
Alexander et al., "Intracranial black-blood MR angiography with high-resolution 3D fast spin echo," Magnetic Resonance in Medicine, 40(2): 298-310 (1998).
Allcock et al., "Polyphosphazenes: New Polymers with Inorganic Backbone Atoms" Science 193:1214-19 (1976).
Alon et al. "Streptavidin contains an RYD sequence which mimics the RGD receptor domain of fibronectin." Biochem. Biophys. Res. Commun. 170:1236-41 (1990).
Anderson et al., "Fiber Optic Immunochemical Sensor for Continuous, Reversible Measurement of Phenytoin," Clin. Chem. 34:7, pp. 1417-1421 (1988).
Andreu et al., "Formation of Disulfide Bonds in Synthetic Peptides and Proteins," Peptide Synthesis Protocols (Pennington, M. W. and Dunn, B. M. Eds.) Humana Press, Totowa N.J. Chap. 7, pp. 91-169 (1994).
Andrieux et al. "Amino acid sequences in fibrinogen mediating its interaction with its platelet receptor, GPllbllla." Journal of Biological Chemistry, 264(16):9258-8265 (1989).
Angeloni et al., The Mannich bases in polymer synthesis: 3. Reduction of poly(beta-aminoketone)s to poly(gamma-aminoalcohol)s and their N-alkylation to poly(gamma-hydroxyquaternary ammonium salt)s, Polymer 23, pp. 1693-1697 (1982).
Ashraf, M. et al., "Solid phase synthesis of peptide dimers and trimers linked through an N-terminal lysine residue" Tetrahedron Letters 2003, 44, 9115-9119.
Backes et al., "Activation Method to Prepare a Highly Reactive Acylsulfonamide "Safety-Catch" Linker for Solid-Phase Synthesis" J. Am. Chem. Soc., 118(12):3055-56 (1996).
Bajusz, "Peptide related drug research," Journal of Peptide Science 9(6), 321-332 (2003).
Bardelli et al., "A Peptide representing the carboxyl-terminal tail of the met receptor inhibits kinase activity and invasive growth," J. Biol. Chem. Oct. 8, 1999; 274(41):29274-81.
Barlos et al., "Convergent Peptide Synthesis" In Fmoc Solid Phase Peptide Synthesis. A Practical Approach, WC Chan, PD White(eds), Oxford University Press, 2000, 215-228.
Bax et al., "The Structure of Phosphorylated GSK-3beta Complexed with a Peptide, FRATtide. that Inhibits Beta-Catenin Phosphorylation" Structure. Dec. 2001;9 (12):1143-52.
Ben-Yedidia, T. et al., "Design of peptide and polypeptide vaccines," Current Opinion in Biotechnology vol. 8, pp. 442-448 (1997).

(56) References Cited

OTHER PUBLICATIONS

Bikfalvi et al., "Interaction of vasculotopin/vascular endothelial cell growth factor with human umbilical vein endothelial cells: binding, internalization, degradation and biological effects," J. Cell Physiol, 149: 50-59, 1991.

Binetruy-Tournaire et al., "Identification of a peptide blocking vascular endothelial growth factor (VEGF)-mediated angiogenesis," EMBO J., Apr. 3, 2000, vol. 19, No. 7, pp. 1525-1533.

Blackwell et al., "Highly efficient synthesis of covalently cross-linked peptide helices by ring-closing metathesis," Angew. Chem. Int. Ed., 37(23):3281-3284 (1998).

Botti et al. "Cyclic Peptides from Linear Unprotected Peptide Precursors through Thiazolidine Formation" J. Am. Chem. Soc., 118:10018-10034 1996.

Cann et al., "Partial Activation of the Isulin Receptor Kinase Domain by Juxtamembrane Autophosphorylation." Biochemistry. Aug. 11, 1998;37(32):11289-300.

Carlsson et al., "Protein Thiolation and Reversible Protein-Protein Conjugation," Biochem. J., 173:723-737 (1978).

Chan et al. "New N- and O-arylations with phenylboronic acids and cupric acetate" Tetrahedron Letters 39:2933-36 (1998).

Chen et al. "Evaluation of an 111In-DOTA—Rhenium Cyclized α-MSH Analog: A Novel Cyclic-Peptide Analog with Improved Tumor-Targeting Properties" J Nucl Med Dec. 1, 2001 vol. 42 No. 12 1847-1855.

Chen, H. et al., "Interaction of dendrimers (artificial proteins) with biological hydroxyapatite crystals," Journal of Dental Research 82, 443-448 (2003).

Chinol, M. et al. "Biodistribution in Tumor-bearing Mice of Two 90Y-Labelled Biotins Using Three-step Tumor Targeting," Nuclear Medicine Communications, vol. 18, No. 2, Feb. 1997, pp. 176-182.

Cho et al., "Purification and Characterization of a Soluble Catalytic Fragment of the Human Transmembrane Leukocyte Antigen Related (LAR) Protein Tyrosine Phosphatase from an Escherichia coli Expression System" Biochemistry 37(51):17754-17764 (1998).

Clark et al., "Covalent Capture and Stabilization of Cylindrical β-Sheet Peptide Assemblies" Chem. Eur. J., 5(2):782-792 (1999).

Clark et al., "Supramolecular Design by Covalent Capture. Design of a Peptide Cylinder via Hydrogen-Bond-Promoted Intermolecular Olefin Metathesis" J Am. Chem. Soc., 117(49):12364-12365 (1995).

Date et al., HGF/NK4 is a specific antagonist for pleiotrophic actions of hepatocyte growth factor. FEBS Lett. Dec. 22, 1997; 420(1): 1-6.

Davis, L.G. et al. "Basic Methods in Molecular Biology", Elsevier, New York, p. 364 (1986).

Dawson, P.E. et al., "Synthesis of Native Proteins by Chemical Ligation," Ann. Rev. Biochem. 69, 923-960 (2000).

De Villiers, et al., "Solubilization of poorly water soluble non-steroidal anti-inflammatory drugs at low pH with N-methylglucamine," S. Afr. Pharmazie, 55, 544-546 (2000).

Edelman et al., "Extracranial carotid arteries: evaluation with "black blood" MR angiography" Radiology, 177(1):45-50 (1990).

Evans et al. "Synthesis of Diaryl Ethers through the Copper-Promoted Arylation of Phenols with Arylboronic Acids. An Expedient Synthesis of Thyroxine," Tetrahedron Lett 39:2937-2940 (1998).

Fairbrother et al., "Novel peptides selected to bind vascular endothelial growth factor target the receptor-binding site," Biochemistry 37(51): 17754-17764, 1998.

Falorni et al., "New 1,3,5-triazine derivatives as templates for the homogeneous phase synthesis of chemical libraries" Tetrahedron Lett., 39(41):7607-7610 (1998).

Fields, G.B. et al., "Principles and Practice of Solid Phase Synthesis" in Synthetic Peptides, A Users Guide, Grant, G.A. ed., W.H. Freeman Co. NY. 1992, Chap. 3 pp. 77-183.

Folkman et al., Cancer Medicine, 5th Edition (B.C. Decker Inc.; Ontario, Canada, 2000) pp. 132-152.

Fukumura et al., "Tumor induction of VEGF promoter activity in stromal cells," Cell 94: 715-725, 1998.

Futaki, "Creation of ion channel function using synthetic peptides," Journal of Synthetic Organic Chemistry, Japan, vol. 56, No. 28; 125-133 (1998).

Gestwicki, J. E. et al., "Influencing Receptor-Ligand Binding Mechanisms with Multivalent Ligand Architecture," J. Am. Chem. Soc. 124, 14922-14933 (2002).

Goodrich et al. "A Quantitative Study of Ramped Radio Frequency, Magnetization Transfer, and Slab Thickness in Three-Dimensional Time-of-Flight Magnetic Resonance Angiography in a Patient Population" Investigative Radiology, 31(61):323-32 (1996).

Goodwin et al., "Advances in pretargeting biotechnology," Biotechnology Advances 19(6), 435-450 (2001).

Hanahan et al., "Patterns and emerging mechanisms of the angiogenic switch during tumorigenesis," Cell 86: 353-364, 1996.

Hanessian et al., "Synthesis of a Versatile Peptidomimetic Scaffold" in Methods in Molecular Medicine, vol. 23: Peptidomimetics Protocols, W.M. Kazmierski Ed. (Humana Press Inc. Totowa, NJ 1999), Chapter 10, pp. 161-174.

Hart et al., "Cyclophilin Inhibition by a (Z)-Alkene cis-Proline Mimic" J. Org. Chem., 64:2998-2999 (1999).

Harvath et al., "Laminin peptides stimulate human neutrophil motility," J. Immunol. Jun. 1, 1994; 152(11):5447-56.

Heller, "Controlled Release of Biologically Active Compounds from Bioerodible Polymers," Biomaterials, 1:51-57 (1980).

Herynk et al., "Down-Regulation of c-Met Inhibits Growth in the Liver of Human Colorectal Carninoma Cells," Cancer Research 63, 2990-2996, Jun. 1, 2003.

Hetian et al., A Novel Peptide Isolated from a Phage Display Library Inhibits Tumor Growth and Metastasis by Blocking the Binding of Vascular Endothelial Growth Factor to its Kinase Domain Receptor. J Biol Chem. Nov. 8, 2002;277(45):43137-42. Epub Aug. 14, 2002.

Hillairet de Boisferon, M. et al., "Enhanced Targeting Specificity to Tumor Cells by Simultaneous Recognition of Two Antigens," Bioconjugate Chem. 11, 452-460 (2000).

Hiller et al. "Biotin binding to avidin. Oligosaccharide side chain not required for ligand association." Biochem J. 248:167-171 (1987).

Holmes et al., "Site specific 1:1 opioid: albumin conjugate with in vitro activity and long in vivo duration," Bioconjug Chem 11: 439-444, 2000.

Howie et al. "Synthetic peptides representing discontinuous CD4 binding epitopes of HOV-1 gp120 that induce T cell apoptosis and block cell death induced by gp120", FASEB J, 12(11):991-998 (1998).

Hsu et al., "Autophosphorylation of the Intracellular Domain of the of the epidermal growth Factor Receptor Results in Different Effects on its Tyrosine Kinase Activity with Various Peptide Substrates. Phosphorylation of Peptides Representing Tyr(P) Sites of Phospholipase C-gamma." J Biol Chem. Jan. 5, 1991; 266(1):603-8.

Hunter et al. "Native Chemical Ligation of Hydrophobic Peptides in Lipid Bilayer Systems," Bioconjugate Chem. 15, 437-440. (2004).

Hutchinson, "Evanescent wave biosensors Real-time analysis of biomolecular interactions" Molec. Biotechnology 1995: 3: 47-54.

Inman, J. et al., "Synthesis of N.alpha.-(tert-butoxycarbonyl)-N.epsilon.-[N-(bromoacetyl)-.beta.-alanyl]-L-lysine: Its use in peptide synthesis for placing a bromoacetyl cross-linking function at any desired sequence position", Bioconjugate Chem, 2:458-463 1991.

Iwamoto et al., "YIGSR, a synthetic laminin pentapeptide, inhibits experimental metastasis formation," Science, Nov. 20, 1987; 238(4830):1132-4.

Jackson, D. C. et al., "Preparation and properties of totally synthetic immunogens," Vaccine 18, 355-361 (2000).

Jia et al., "Peptides encoded by exon 6 of VEGF inhibit endothelial cell biological responses and angiogenesis induced by VEGF," Biochem Biophys Res Commun. Apr. 27, 2001; 283(1):164-73.

Johnson et al. "Libraries of N-alkylaminoheterocycles from nucleophilic aromatic substitution with purification by solid supported liquid extraction" Tetrahedron Lett.,54(16):4097-4106 (1998).

Kihlberg, "Glycopeptide synthesis," In Fmoc Solid Phase Peptide Synthesis—A Practical Approach (Chan, W.C. and White, P.D. eds) Oxford University Press, New York, NY, Chap. 8, pp. 195-213 (2000).

Kim et al., "Inhibition of vascular endothelial growth factor-induced angiogenesis suppresses tumor growth in vivo," Nature 362: 841-844, 1993.

(56) References Cited

OTHER PUBLICATIONS

Kitagawa et al., "Synthesis of Two Substance P Analogs, [8-Tyr] and [5-Asn] Substance P," Chem. Pharm. Bull., 26(9): 2899-2903 (1978).
Knudsen, et al., "Potent Derivatives of Glucagon-like Peptide-1 with Pharmacokinetic Properties Suitable for Once Daily Administration," J. Med. Chem., 43:1664-1669 (2000).
Laemmli et al., "Cleavage of Structural Proteins during the Assembly of the Head of Bacteriophage T4" Nature, 227:680-685 (1970).
Lam et al. "New aryl/heteroaryl C N bond cross-coupling reactions via arylboronic acid/cupric acetate arylation" Tetrahedron Letters 39:2941-2944 (1998).
Lanza et al. "High-frequency ultrasonic detection of thrombi with a targeted contrast system" Ultrasound in Med. & Bio., 23(6):863-870 (1997).
Lecouter et al., "Identification of an angiogenic mitogen selective for endocrine gland endothelium," Nature, Aug. 30, 2001; 412(6850):877-84.
Liu et al. "99mTc-Labeled Small Peptides as Diagnostic Radiopharmaceuticals" Chem. Rev., 99 (9), pp. 2235-2268 (1999).
Liu, S. et al., "99mTc-Labeling of Hydrazinonicotiniamide-Conjugated Vitronection Receptor Antagonist Useful for Imaging Tumors," Bioconjugate Chem. 12, 624-629 (2001).
Loffet, A. Q. Peptides as drugs: is there a market? In: Peptides: The Wave of the Future, Proceedings of the Second International and the Seventeenth American Peptide Symposium, San Diego, CA United States, Jun. 9-14, 2001; Lebl, M., and Houghten, R. A. Eds.; American Peptide Society: San Diego, Calif. 2001; pp. 214-216.
Lu et al., "Acquired antagonistic activity of a bispecific diabody directed against two different epitopes on vascular endothelial growth factor receptor 2," J. Immunol. Methods, Nov. 11, 1999, vol. 230, No. 1-2, pp. 159-171.
Lu, D. et al. "Identification of the Residues in the Extracellular Region of KDR Important for Interaction with Vascular Endothelial Growth Factor and Neutralizing Anti-KDR Antibodies", J. Biol. Chem., May 2000, vol. 275, No. 19, pp. 14321-14330.
Lucke, A. J. et al., "Designing supramolecular structures from models of cyclic peptide scaffolds with heterocyclic constraints," Journal of Molecular Graphics & Modelling 21(5), 341-355 (2003).
Malmborg et al. Selection of binders from phage displayed antibody libraries using the BIAcore™ biosensor. J Immunol Methods 1996;198:51-7.
Mammen, M. et al., "Polyvalent interactions in biological systems: Implications for design and use of multivalent ligands and inhibitors," Angew. Chem. Int. Edn. Engl. 37, 2754-2794 (1998).
Matsudiara et al., "Sequence from picomole quantities of proteins electroblotted onto polyvinylidene difluoride membranes," J. Biol Chem Jul. 25, 1987; 262(21): 10035-8.
Mayer et al., "Peptides, Frontiers of Peptide Science," in Proceedings of the 15th American peptide Symposium, Tam and Kaumaya (Eds.), Jun. 14-19, 1995, Nashville, Tenn. (Klumer Academic Pub., Boston), pp. 291-292.
Melkko et al. "Encoded self-assembling chemical libraries" Nature Biotechnology, vol. 22, No. 5, May 2004, pp. 568-574.
Mellor, S.L. et al., "Synthesis of Modified Peptides" in Fmoc Solid Phase Synthesis: A Practical Approach, White and Chan (eds), Oxford University Press, New York, 2000, Chap 6: pp. 169-178.
Merkx, R. et al., "Chemoselective coupling of peptide fragments using the Staudinger ligation." Tetrahedron Lett. 44, 4515-4518 (2003).
Miller et al., "Application of Ring-Closing Metathesis to the Synthesis of Rigidified Amino Acids and Peptides," J. Am. Chem. Soc. 118(40):9606-9614 (1996).
Miller et al., "Synthesis of Conformationally Restricted Amino Acids and Peptides Employing Olefin Metathesis," J. Am. Chem. Soc. 117(21):5855-5856 (1995).
Muller, K. et al. "A dimeric bispecific miniantibody combines two specificities with avidity" FEBS Letters, vol. 432, No. 1-2, Jul. 31, 1998, pp. 45-49.
Mutter et al., "Evolution versus design: template-directed self-assembly of peptides to artificial proteins (TASP)," Chimia 54, 552-557 (2000).
Neri, D. et al. "High-affinity Antigen Binding by Chelating Recombinant Antibodies" Journal of Molecular Biology, vol. 246, No. 3, Feb. 24, 1995, pp. 367-373.
Neufeld et al., "Vascular endothelial growth factor (VEGF) and its receptors," FASEB J 13: 9-22, 1999.
O'Brien-Simpson, N. et al., "Polymerization of Unprotected Synthetic Peptides: A View toward Synthetic Peptide Vaccines," Journal of the American Chemical Society 119, 1183-1188 (1997).
Offer et al., "Extending Synthetic Access to Proteins with a Removable Acyl Transfer Auxiliary," J. Am. Chem. Soc. 124, 4642-4646 (2002).
Oldberg et al. "Identification of a bone sialoprotein receptor in osteosarcoma cells." Journal of Biological Chemistry, 263(36):19433-19436 (1988).
Parr et al., "Hepatocyte growth factor activators, inhibitors and antagonists and their implication in cancer intervention" Histol Histopathol. Jan. 2001;16(1):251-68. Review.
Pepper et al., "Angiogenesis: a paradigm for balanced extracellular proteolysis during cell migration and morphogenesis," Enzyme Protein. 49(1-3): 138-62. 1996.
Pernerstorfer et al. "Cyclisation/cleavage of macrocycles by ring-closing metathesis on solid support—conformational studies" Chem. Commun., 20:1949-50 (1997).
Pillai et al, "A Flexible Method for Preparation of Peptide Homo- and Heterodimers Functionalized with Affinity Probes, Chelating Ligands and Latent Conjugating Groups" Biopolymers (Peptide Science), vol. 84, 576-585 (2006).
Pillai et al, "A Flexible Method for Preparation of Peptide Homo- and Heterodimers Functionalized with Affinity Probes, Chelating Ligands and Latent Conjugating Groups", The Ernst Felder Laboratories, Bracco Research USA, Inc., 305 College Road East, Princeton, New Jersey, 08540-6608, Jun. 29, 2005.
Pillai et al., "A Novel and Flexible Method for Preparation of Peptide Homo and Heterodimers Functionalized with Affinity Probes, Reporter Molecules and Chelating Ligands" Poster Presentation at the Third International and Twenty-Eight European Peptide Symposium, Prague, Czech Republic, Sep. 5-10, 2004.
Pillai et al., "A Novel and Flexible Method for Preparation of Peptide Homo- and Heterodimers Functionalized with Affinity Probes, Reporter Molecules and Chelating Ligands," from the Proceedings of the Peptides Third International and Twenty-Eight European Peptide Symposium, Sep. 5-10, 2004, Prague, Czech Republic, pp. 254-256.
Ploinsky et al. "Synthesis and conformational properties of the lanthionine-bridged opioid peptide [D-AlaL2,AlaL5]enkephalin as determined by NMR and computer simulations" Med.Chem 35:4185-4194 1992.
Plow et al., "Arginyl-glycyl-aspartic acid sequences and fibrinogen binding to platelet" Blood, 70(1):110-5 (1987).
Pritchard et al., "A Truncated V-abl-derived tyrosine-specific Tyrosine Kinase Expressed in *Escherichia coli*" Biochem J. Jan. 15, 1989;257(2):321-9.
Ripka et al., Synthesis of novel cyclic protease inhibitors using Grubbs olefin metathesis, Med. Chem. Lett., 8(4):357-360 (1998).
Risau et al., "Mechanisms of angiogenesis," Nature 386:671-674, 1997.
Robert, Bruno et al., "Tumor targeting with newly designed biparatopic antibodies directed against two different epitopes of the cecinoembryonic antigen (CEA)" International Journal of Cancer, New York, NY, US, vol. 81, Apr. 12, 1999, pp. 285-291.
Roberts et al., "Chemistry for peptide and protein PEGylation," Adv Drug Deliv Rev. Jun. 17, 2002; 54(4): 459-76.
Robey, et al., "Automated Synthesis of N-Bromoacetyl-Modified Peptides for the Preparation of Synthetic Peptide Polymers, Peptide-Protein Conjugates, and Cyclic Peptides", Anal. Biochem. 177: 373-377 (1989).
Rose, K. et al., "Stepwise Solid-Phase Synthesis of Polyamides as Linkers", J. Am. Chem. Soc., 1999, 121:7034-7038.
Rosebrough, S. F., "Two-step immunological approaches for imaging and therapy", Q.J. Nucl. Med., 40:234-251 (1996).

(56) References Cited

OTHER PUBLICATIONS

Rovero, P. et al., "Solid phase synthesis and dimerization of an azobenzene-containing peptide as photoisomerizable proteinase inhibitor" Letters in Peptide Science 1995, 2, 27-32.
Sadler, Kristen et al., "Peptide dendrimers: applications and synthesis," Reviews in Molecular Biotechnology 90(3-4), 195-229 (2002) (general review).
Sal-Man, N. et al., "Preassembly of membrane-active peptides is an important factor in their selectivity toward target cells," Biochemistry 41, 11921-11930 (2002).
Sato et al., "Development of mammalian serum albumin affinity purification media by peptide phage display," Biotechnol Prog. Mar.-Apr. 2002; 18(2):182-92.
Schaeper, U. et al., "Coupling of Gab1 to c-Met, Grb2 and Shp2 Mediates Biological Responses" The Journal of Cell Biology, vol. 149, No. 7, Jun. 26, 2000, pp. 1419-1432.
Schaffer et al., "Assembly of high-affinity insulin receptor agonists and antagonists from peptide building blocks," Proc Natl Acad Sci USA Apr. 15, 2003:100(8): 4435-9.
Schmitz et al."Catalytic specificity of phosphotyrosine kinases Blk, Lyn, c-Src and Syk as assess by phage display," J. Mol. Biol. Aug. 2, 1996; 260(5):664-77.
Schuck, P. "Reliable Determination of Binding Affinity and Kinetics Using Surface Plasmon Resonance Biosensors". Current Opinion in Biotechnology. vol. 8: 498-502 (1997).
Shrivastava et al., "A distinct strategy to generate high-affinity peptide binders to receptor tyrosine kinases," Protein Eng Des Sel. Sep. 2005; 18(9):417-24.
Sleep et al., "*Saccharomyces cerevisiae* strains that overexpress heterologous proteins," Biotechnology (NY) Feb. 1991; 9(2): 183-7.
Soker et al., "Inhibition of vascular endothelial growth factor (VEGF)-induced endothelial cell proliferation by a peptide corresponding to the exon 7-encoded domain of VEGF165," Journal of Biol Chem 272(50): 31582-31588 (1997).
Sole, N. A., et al. "Optimization of solid-phase synthesis of [Ala8]-Dynorphin" A. J. Org. Chem. 57, 5399-5403. (1992).
Souriau, C. et al. "Recombinant antibodies for cancer diagnosis and therapy." Expert Opin. Biol. Ther. 1(5), 845-855. (2001).
Stankova et al. "Library Generation through Successice Substitution of Trichlorotriazine" Mol. Diversity, 2(1/2):75-80 (1996).
Strawn et al., "Flk-1 as a target for tumor growth inhibition," Cancer Res 56: 3540-3545, 1996.
Tam, J. P. et al., "Antimicrobial Dendrimeric Peptides," European Journal of Biochemistry 269, 923-932 (2002).
Tam, J., "Vaccines 90. Modern approaches to new vaccines including prevention of AIDS," p. 21 (R. A. Lerner,et al. Eds., Cold Spring Harbor Lab., New York, 1990).
Tam, J.P., et al., "Tandem Ligation of Unprotected Peptides through Thiaprolyl and Cysteinyl Bonds in Water" J. Am. Chem. Soc. 123, 2487-2494 (2001).
Tamura, S. et al. "Expression and Function of c-Met, a Receptor for Hepatocyte Growth Factor, During T-Cell Development", Scand. J. Immunol. 1998, vol. 47, pp. 296-301.
Taub et al. "A monoclonal antibody against the platelet fibrinogen receptor contains a sequence that mimics a receptor recognition domain in fibrinogen." Journal of Biological Chemistry, 264(1):259-265 (1989).
Thomas et al., "A peptide sequence on carcinoembryonic antigen binds to a 80kD protein on Kupffer cells," Biochem Biophys Res Commun 188: 671-677, 1992.
Thumshirn, G. et al., "Multimeric cyclic RGD peptides as potential tools for tumor targeting: Solid-phase peptide synthesis and chemoselective oxime ligation," Chemistry—A European Journal 9(12), 2717-2725 (2003).
Tissot et al., "Characterizing the functionality of recombinant T-cell receptors in vitro: a pMHC tetramer based approach," J. Immunol. Methods 236(1-2): 147-165 (2000).
Todorovska et al., "Design and Application of Diabodies, Triabodies and Tetrabodies for Cancer Targeting," J. Immunol. Methods vol. 248, No. 1-2, pp. 47-66 (Feb. 1, 2001).

Tweedle et al., Magnetic Resonance Imaging (2nd ed.), vol. 1, Partain et al., eds. (W.B. Saunders Co., 1988), pp. 796-797.
Veikkola et al., "Regulation of angiogenesis via vascular endothelial growth factor receptors," Cancer Res 60: 203-212, 2000.
Veprek, P. and Jezek, J. (1999) Peptide and glycopeptide dendrimers. Part I. J. Pept. Sci. 5, 5-23.
Veprek, P. and Jezek, J. (1999) Peptide and glycopeptide dendrimers. Part II. J. Pept. Sci. 5, 203-220.
Wade, J.D. et al., "Use of thiazolidine-mediated ligation for site specific biotinylation of mouse EGF for biosensor immobilisation," Letters in Peptide Science, vol. 8(3-5), 211-220 (2002).
Wahl et al. "Analogues of oxytocin with an oxime bridge using chemo selectively addressable building blocks," Tetrahedron Lett. 37, 6861-6864 (1996).
Wedegaertner et al., "Effect of Carboxyl Terminal Truncation on the Tyrosine Kinase Activity of the Epidermal Growth Factor Receptor" Arch Biochem Boiphys. Jan. 1992; 292(1):27.3-80.
Wei, K. et al. "Quantification of Renal Blood Flow With Contrast-Enhanced Ultrasound" J. Am. Coll. Cardiol., vol. 37, No. 4., pp. 1135-1140 (2001).
Wilken, J. et al., "Chemical protein synthesis," Current Opinion in Biotechnology 9(4), 412-426 (1998).
Zuo, Z. et al., "An efficient route to the production of an IgG-like bispecific antibody" Protein Engineering, vol. 13, No. 5, pp. 361-367, 2000.
Notice of Allowance for U.S. Appl. No. 10/661,032, mailed Dec. 21, 2006.
Notice of Allowance for U.S. Appl. No. 10/661,032, mailed May 25, 2006.
Notice of Allowance for U.S. Appl. No. 10/792,582, mailed Oct. 30, 2007.
Notice of Allowance for U.S. Appl. No. 10/916,155, mailed Oct. 29, 2009.
Notice of Allowance for U.S. Appl. No. 11/608,395, mailed Feb. 19, 2010.
Notice of Allowance for U.S. Appl. No. 11/624,894, mailed Jun. 23, 2010.
Notice of Allowance for U.S. Appl. No. 11/688,968, mailed Sep. 21, 2010.
Notice of Allowance for U.S. Appl. No. 11/954,130, mailed Mar. 16, 2011.
Notice of Allowance for U.S. Appl. No. 12/012,011, mailed Jun. 9, 2011.
Notice of Allowance for U.S. Appl. No. 12/480,578, mailed Apr. 27, 2012.
Notice of Allowance issued in U.S. Appl. No. 10/379,287, mailed May 10, 2006.
Notice of Allowance issued in U.S. Appl. No. 10/379,287, mailed Oct. 18, 2006.
Office Action for U.S. Appl. No. 10/379,287, mailed Jun. 28, 2005.
Office Action for U.S. Appl. No. 10/661,032, mailed Aug. 1, 2005.
Office Action for U.S. Appl. No. 10/792,582, mailed Mar. 8, 2007.
Office Action for U.S. Appl. No. 10/916,155, mailed Aug. 12, 2009.
Office Action for U.S. Appl. No. 10/916,155, mailed Dec. 13, 2007.
Office Action for U.S. Appl. No. 11/608,395, mailed Dec. 2, 2008.
Office Action for U.S. Appl. No. 11/624,894, mailed Oct. 2, 2009.
Office Action for U.S. Appl. No. 11/624,894, mailed Sep. 30, 2009.
Office Action for U.S. Appl. No. 11/688,968, mailed Aug. 27, 2010.
Office Action for U.S. Appl. No. 11/688,968, mailed Oct. 28, 2009.
Office Action for U.S. Appl. No. 12/480,578, mailed Jan. 21, 2011.
Office Action for U.S. Appl. No. 12/888,736, mailed May 11, 2012.
Office Action issued in U.S. Appl. No. 10/661,156 and mailed Mar. 31, 2008.
Office Action issued in U.S. Appl. No. 10/661,156 and mailed Nov. 9, 2006.
Office Action issued in U.S. Appl. No. 11/954,130, mailed Sep. 2, 2010.
Office Action issued in U.S. Appl. No. 12/257,552, mailed Nov. 28, 2011.
Supplemental Notice of Allowance for U.S. Appl. No. 11/624,894, mailed Aug. 19, 2010.
Final Office Action for U.S. Appl. No. 10/379,287, mailed Jan. 24, 2006.

(56) References Cited

OTHER PUBLICATIONS

Final Office Action for U.S. Appl. No. 10/661,032, mailed Feb. 8, 2006.
Final Office Action for U.S. Appl. No. 11/624,894, mailed Mar. 10, 2010.
Final Office Action for U.S. Appl. No. 11/688,968, mailed Apr. 15, 2010.
Final Office Action for U.S. Appl. No. 12/480,578, mailed Nov. 25, 2011.
Final Office Action issued in U.S. Appl. No. 10/661,156 and mailed Jan. 7, 2009.
Final Office Action issued in U.S. Appl. No. 10/661,156 and mailed Jul. 26, 2007.
Final Office Action issued in U.S. Appl. No. 11/608,395, mailed Jun. 1, 2009.
Final Office Action issued in U.S. Appl. No. 11/954,130, mailed Dec. 23, 2010.
Final Office Action issued in U.S. Appl. No. 12/257,552, mailed Jul. 9, 2012.
Rodionov, ABRF Electronic Discussion Group (Jul. 28, 2000); Downloaded Jul. 1, 2012.
Kirpotin et al., "Sterically stabilized Anti-HER2 immunoliposomes: design and targeting to human breast cancer cells in vitro," Biochemistry 36: 66-75 (1997).
Dubey, et al., "Liposomes Modified with Cyclic RGD Peptide for Tumor Targeting," Journal of Drug Targeting, Jun. 2004, vol. 12, No. 5, pp. 257-264.
Extended European Search Report issued for European Patent Application No. 10190163.5, dated Jun. 29, 2012.
Notification of Reasons for Rejection issued in Japanese Patent Application No. 2008-544663, date of delivery Nov. 15, 2012, and an English translation thereof.
Office Action issued in Korean Patent Application No. 10-2008-7016674, dated Jun. 13, 2013, and an English translation thereof.
Preliminary Rejection issued for Korean Patent Application No. 10-2013-7021393, dated Oct. 30, 2013.
Office Action Issued for U.S. Appl. No. 14/109,508, dated Nov. 19, 2015.
Office Action Issued for U.S. Appl. No. 14/085,645, dated Oct. 8, 2015.
US 5,171,298, 12/1992, Walker et al. (withdrawn)

SEQUENCE LISTING

```
<160> NUMBER OF SEQ ID NOS: 5

<210> SEQ ID NO 1
<211> LENGTH: 29
<212> TYPE: PRT
<213> ORGANISM: Artificial
<220> FEATURE:
<223> OTHER INFORMATION: Description of Artificial Sequence:  synthetic
      peptide
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (29)..(29)
<223> OTHER INFORMATION: (DSPE-PEG2000-NH-Glut)-NH2

<400> SEQUENCE: 1

Arg Ala Gln Asp Trp Tyr Tyr Asp Glu Ile Leu Ser Met Ala Asp Gln
1               5                   10                  15

Leu Arg His Ala Phe Leu Ser Gly Gly Gly Gly Gly Lys
            20                  25
```

```
<210> SEQ ID NO 2
<211> LENGTH: 29
<212> TYPE: PRT
<213> ORGANISM: Artificial
<220> FEATURE:
<223> OTHER INFORMATION: Description of Artificial Sequence:  synthetic
      peptide
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (29)..(29)
<223> OTHER INFORMATION: NH2

<400> SEQUENCE: 2

Arg Ala Gln Asp Trp Tyr Tyr Asp Glu Ile Leu Ser Met Ala Asp Gln
1               5                   10                  15

Leu Arg His Ala Phe Leu Ser Gly Gly Gly Gly Gly Lys
            20                  25

<210> SEQ ID NO 3
<211> LENGTH: 29
<212> TYPE: PRT
<213> ORGANISM: Artificial
<220> FEATURE:
<223> OTHER INFORMATION: Description of Artificial Sequence:  synthetic
      peptide
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (29)..(29)
<223> OTHER INFORMATION: (NHS-Glut)-NH2

<400> SEQUENCE: 3

Arg Ala Gln Asp Trp Tyr Tyr Asp Glu Ile Leu Ser Met Ala Asp Gln
1               5                   10                  15

Leu Arg His Ala Phe Leu Ser Gly Gly Gly Gly Gly Lys
            20                  25

<210> SEQ ID NO 4
<211> LENGTH: 28
<212> TYPE: PRT
<213> ORGANISM: Artificial
<220> FEATURE:
<223> OTHER INFORMATION: Description of Artificial Sequence:  synthetic
      peptide
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (28)..(28)
<223> OTHER INFORMATION: (DSPE-PEG2000-NH-Glut)-NH2

<400> SEQUENCE: 4

Ala Gln Asp Trp Tyr Tyr Asp Glu Ile Leu Ser Met Ala Asp Gln Leu
1               5                   10                  15

Arg His Ala Phe Leu Ser Gly Gly Gly Gly Gly Lys
            20                  25

<210> SEQ ID NO 5
<211> LENGTH: 28
<212> TYPE: PRT
<213> ORGANISM: Artificial
```

```
-continued

<220> FEATURE:
<223> OTHER INFORMATION: Description of Artificial Sequence:  synthetic
      peptide
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (28)..(28)
<223> OTHER INFORMATION: NH2

<400> SEQUENCE: 5

Ala Gln Asp Trp Tyr Tyr Asp Glu Ile Leu Ser Met Ala Asp Gln Leu
1               5                   10                  15

Arg His Ala Phe Leu Ser Gly Gly Gly Gly Lys
            20                  25
```

TARGETING VECTOR-PHOSPHOLIPID CONJUGATES

RELATED APPLICATIONS

This application is a continuation of U.S. patent application Ser. No. 12/257,552, filed Oct. 24, 2008, which is a divisional of U.S. patent application Ser. No. 11/608,395, filed Dec. 8, 2006, now issued as U.S. Pat. No. 7,794,693, which claims priority to and benefit of U.S. Provisional Application No. 60/833,342, filed Jul. 25, 2006 and U.S. Provisional Application No. 60/749,240, filed Dec. 9, 2005, the contents of each which are hereby incorporated herein by reference.

FIELD OF THE INVENTION

The present invention relates to targeting vector-phospholipid conjugates and particularly targeting peptide-phospholipid conjugates, which are useful in therapeutic and diagnostic compositions and methods of preparation of the same. The invention includes targeted ultrasound contrast agents, and particularly targeted microbubbles which include such targeting vector-phospholipid conjugates.

BACKGROUND OF THE INVENTION

Angiogenesis, the formation of new blood vessels, occurs not only during embryonic development and normal tissue growth and repair, but is also involved in the female reproductive cycle, establishment and maintenance of pregnancy, and repair of wounds and fractures. In addition to angiogenesis that occurs in the normal individual, angiogenic events are involved in a number of pathological processes, notably tumor growth and metastasis, and other conditions in which blood vessel proliferation is increased, such as diabetic retinopathy, psoriasis and arthropathies. In addition, angiogenesis is important in the transition of a tumor from hyperplastic to neoplastic growth. Consequently, inhibition of angiogenesis has become an active cancer therapy research field.

Tumor-induced angiogenesis is thought to depend on the production of pro-angiogenic growth factors by the tumor cells, which overcome other forces that tend to keep existing vessels quiescent and stable. The best characterized of these pro-angiogenic agents or growth factors is vascular endothelial growth factor (VEGF) (Cohen et al., *FASEB J.*, 13: 9-22 (1999)). VEGF is produced naturally by a variety of cell types in response to hypoxia and some other stimuli. Many tumors also produce large amounts of VEGF, and/or induce nearby stromal cells to make VEGF (Fukumura et al., *Cell*, 94: 715-725 (1998)). VEGF, also referred to as VEGF-A, is synthesized as five different splice isoforms of 121, 145, 165, 189, and 206 amino acids. $VEGF_{121}$ and $VEGF_{165}$ are the main forms produced, particularly in tumors (see Cohen et al. 1999, supra). $VEGF_{121}$ lacks a basic domain encoded by exons 6 and 7 of the VEGF gene and does not bind to heparin or extracellular matrix, unlike $VEGF_{165}$. Each of the references cited in this paragraph is incorporated by reference in its entirety.

VEGF family members act primarily by binding to receptor tyrosine kinases. In general, receptor tyrosine kinases are glycoproteins having an extracellular domain capable of binding one or more specific growth factors, a transmembrane domain (usually an alpha helix), a juxtamembrane domain (where the receptor may be regulated, e.g., by phosphorylation), a tyrosine kinase domain (the catalytic component of the receptor), and a carboxy-terminal tail, which in many receptors is involved in recognition and binding of the substrates for the tyrosine kinase. There are three endothelial cell-specific receptor tyrosine kinases known to bind VEGF: VEGFR-1 (Flt-1), VEGFR-2 (KDR or Flk-1), and VEGFR-3 (Flt4). Flt-1 and KDR (also known as VEGFR-2 or Flk-1, which are used interchangeably herein) have been identified as the primary high affinity VEGF receptors. While Flt-1 has higher affinity for VEGF, KDR displays more abundant endothelial cell expression (Bikfalvi et al., J. Cell. Physiol., 149: 50-59 (1991)). Moreover, KDR is thought to dominate the angiogenic response and is therefore of greater therapeutic and diagnostic interest (see Cohen et al. 1999, supra). Expression of KDR is highly upregulated in angiogenic vessels, especially in tumors that induce a strong angiogenic response (Veikkola et al., Cancer Res., 60: 203-212 (2000)). The critical role of KDR in angiogenesis is highlighted by the complete lack of vascular development in homozygous KDR knockout mouse embryos (Folkman et al., Cancer Medicine, 5th Edition (B.C. Decker Inc.; Ontario, Canada, 2000) pp. 132-152).

KDR (kinase domain region) is made up of 1336 amino acids in its mature form. The glycosylated form of KDR migrates on an SDS-PAGE gel with an apparent molecular weight of about 205 kDa. KDR contains seven immunoglobulin-like domains in its extracellular domain, of which the first three are the most important in VEGF binding (Cohen et al. 1999, supra). VEGF itself is a homodimer capable of binding to two KDR molecules simultaneously. The result is that two KDR molecules become dimerized upon binding and autophosphorylate, becoming much more active. The increased kinase activity in turn initiates a signaling pathway that mediates the KDR-specific biological effects of VEGF.

Thus, not only is the VEGF binding activity of KDR in vivo critical to angiogenesis, but the ability to detect KDR upregulation on endothelial cells or to detect VEGF/KDR binding complexes would be extremely beneficial in detecting or monitoring angiogenesis.

It is well known that gas filled ultrasound contrast agents are exceptionally efficient ultrasound reflectors for echography. Such ultrasound contrast agents include, for example, gas-filled microvesicles such as gas-filled microbubbles and gas filled microballoons. Gas filled microbubbles are particularly preferred ultrasound contrast agents. (In this disclosure the term of "microbubble" specifically designates a gaseous bubble surrounded or stabilized by phospholipids). For instance injecting into the bloodstream of living bodies suspensions of air or gas-filled microbubbles in a carrier liquid will strongly reinforce ultrasonic echography imaging, thus aiding in the visualization of internal anatomical structures. Imaging of vessels and internal organs can strongly help in medical diagnosis, for instance for the detection of neoplastic, cardiovascular and other diseases.

For both diagnostic and therapeutic purposes it would be particularly beneficial to incorporate into gas filled ultrasound contrast agents, targeting vector compositions which exhibit high binding affinity for a desired target (such as, for example, KDR or the VEGF/KDR complex). For example, targeting vector-phospholipid conjugates and particularly targeting peptide-phospholipid conjugates may be used to prepare targeted, gas filled ultrasound contrast agents. In addition, it would be particularly beneficial to have methods for large scale production of highly purified forms of such targeting vector-phospholipid conjugates. Such compositions and methods would allow for production of compositions for use in diagnostic or therapeutic applications such as, for example, precise targeting of reporter moieties, tumoricidal agents or angiogenesis inhibitors to the target site.

SUMMARY OF THE INVENTION

The present invention provides targeting vector-phospholipid conjugates and particularly targeting peptide-phospholipid conjugates which are useful in the preparation of gas filled ultrasound contrast agents. In a preferred embodiment the targeting peptide-phospholipid conjugates include targeting peptides which exhibit high KDR binding affinity and thus are useful components of contrast agents for imaging of angiogenesis processes.

The present invention also provides monomeric and dimeric peptide phospholipid conjugates (also referred to herein as lipopeptides) which are useful in preparing gas filled ultrasound contrast agents, and particularly in preparing ultrasound contrast agents which target KDR and may be used for imaging of angiogenesis processes.

The present invention also provides methods and processes for the large scale production of highly pure monomeric and dimeric peptide phospholipid conjugates, particularly monomeric and dimeric peptide phospholipids conjugates having high KDR binding affinity.

The present invention also provides methods and processes for the large scale production of highly pure dimeric peptide phospholipid conjugates having minimal levels of trifluoroacetic acid (TFA).

The present invention also provides methods for synthesizing monomeric peptides in high purity and the construction of peptide phospholipid conjugates from multiple peptide subunits.

The present invention also provides monomeric peptides which bind KDR or the VEGF/KDR complex with high affinity, as well as methods of synthesizing and using such monomeric peptides.

The present invention also provides targeted ultrasound contrast agents prepared from such targeting vector-phospholipid conjugates. Such targeted ultrasound contrast agents are useful for imaging target-bearing tissue. In a preferred embodiment, the targeted ultrasound contrast agents are targeted microbubbles and the targeting vector-phospholipid conjugates include targeting peptides which exhibit high KDR binding affinity and thus are useful components of contrast agents for imaging KDR-bearing tissue and particularly for imaging of tumors and angiogenesis processes. Methods of preparing and using such targeted ultrasound contrast agents are also provided.

DETAILED DESCRIPTION

Applicants have unexpectedly discovered peptide phospholipid conjugates, which are useful in producing targeted ultrasound contrast agents and which have exceptional KDR binding efficiency. Two of these compounds are monomeric peptide phospholipid conjugates which include a linear peptide monomer which binds with high affinity to KDR while the other is a dimeric peptide phospholipid conjugate which includes two distinct monomer subunits, each binding to KDR. In addition, highly efficient methods for large scale production of purified forms of these conjugates and precursor materials have been discovered. Such methods include the production of dimeric peptide phospholipid conjugates having minimal levels of TFA.

The phospholipid may be selected from the group consisting of: phosphatidylethanolamines and modified phosphatidylethanolamines Particularly preferred phospholipids include phosphatidylethanolamines modified by linking a hydrophilic polymer thereto. Examples of modified phosphatidylethanolamines are phosphatidylethanolamines (PE) modified with polyethyleneglycol (PEG), in brief "PE-PEGs", i.e. phosphatidylethanolamines where the hydrophilic ethanolamine moiety is linked to a PEG molecule of variable molecular weight (e.g. from 300 to 5000 daltons), such as DPPE-PEG, DSPE-PEG, DMPE-PEG or DAPE-PEG. DSPE-PEG2000, DSPE-PEG3400, DPPE-PEG2000 and DPPE-PEG3400 are preferred, with DSPE-PEG2000 particularly preferred. Note that a salt form of the phospholipid may be used, such as, for example, the trimethyl ammonium salt, the tetramethylammonium salt, the triethylammonium salt, sodium salt, etc.

These compounds may be incorporated into gas filled ultrasound contrast agents, such as, for example, gas filled microbubbles to form contrast agents that provide excellent imaging of target-bearing tissue. In a preferred embodiment, targeting vector-phospholipid conjugates which include targeting peptides which bind with high affinity to KDR are incorporated into targeted microbubbles. As shown herein, such targeted microbubbles selectively localize at KDR-bearing tissue, permitting imaging of such tissue, and, in particular imaging of tumors and angiogenic processes, including those processes associated with neoplastic development.

Monomer Conjugates
Generally

Table 1 provides a description for the identification labels shown in FIGS. 1, 2, 9 and 10.

TABLE 1

```
1   Ac-RAQDWYYDEILSMADQLRHAFLSGGGGGK(DSPE-PEG2000-NH-Glut)-
    NH₂ (SEQ ID NO. 1)

2   Ac-RAQDWYYDEILSMADQLRHAFLSGGGGGK-NH₂ (SEQ ID NO. 2)

3   mono-NHS ester of glutaryl-peptide monomer (2)
    Ac-RAQDWYYDEILSMADQLRHAFLSGGGGGK(NHS-Glut)-NH₂ (SEQ ID
    NO. 3)

4   DSPE-PEG2000-NH2 phospholipid
    1,2-distearoyl-sn-glycero-3-phosphoethanolaminocarbonyloxy-(PEG2000)-amine 31  Ac-AQDWYYDEILSMADQLRHAFLSGGGGGK(DSPE-PEG2000-NH-Glut)-
    NH₂ (SEQ ID NO. 4)

32  Ac-AQDWYYDEILSMADQLRHAFLSGGGGGK-NH₂ (SEQ ID NO. 5)
```

Figure 1:
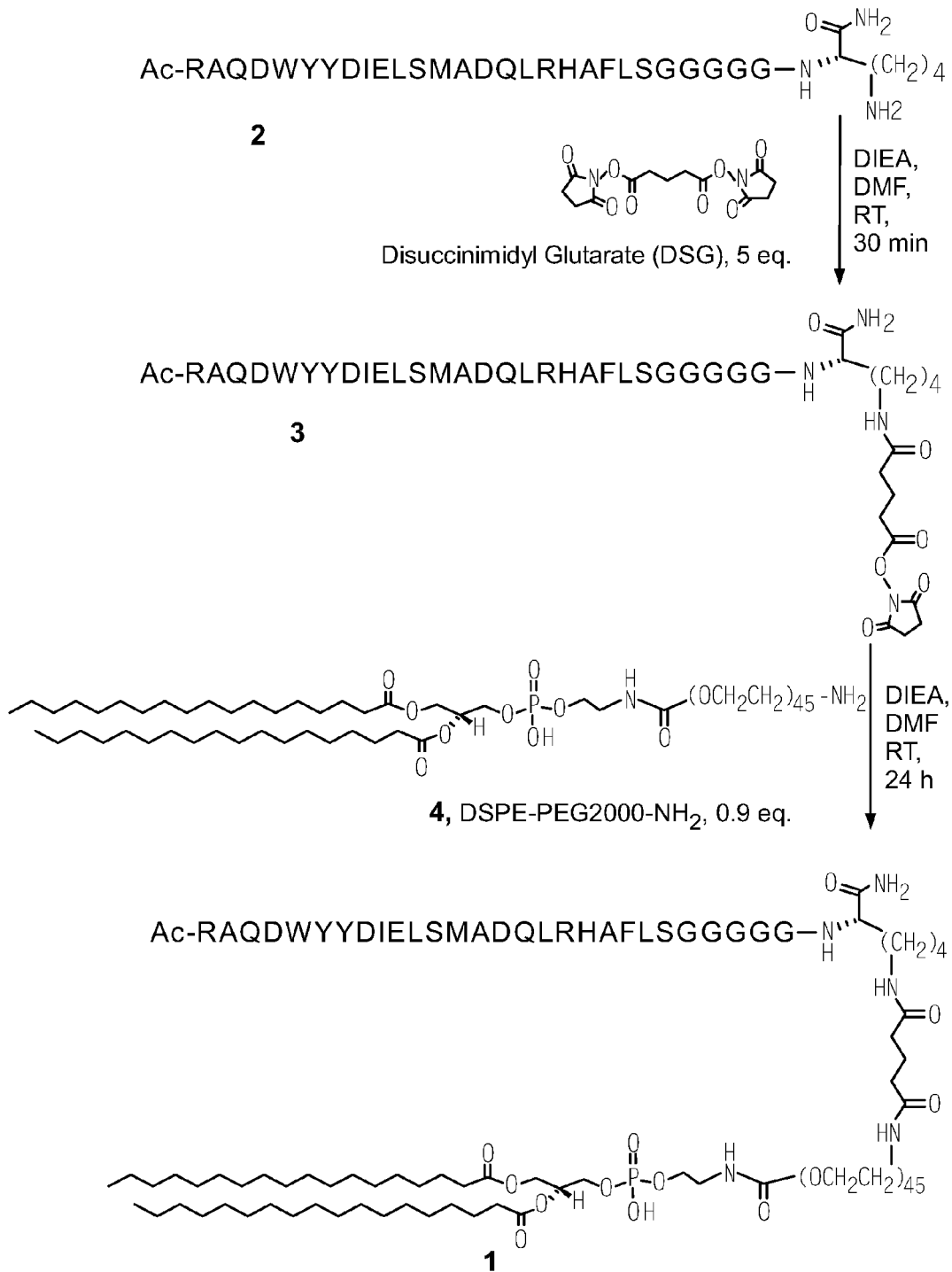
FIG. 1 illustrates a method for the production of a monomeric peptide phospholipid conjugate (1) from a linear peptide monomer (2).
Figure 2:
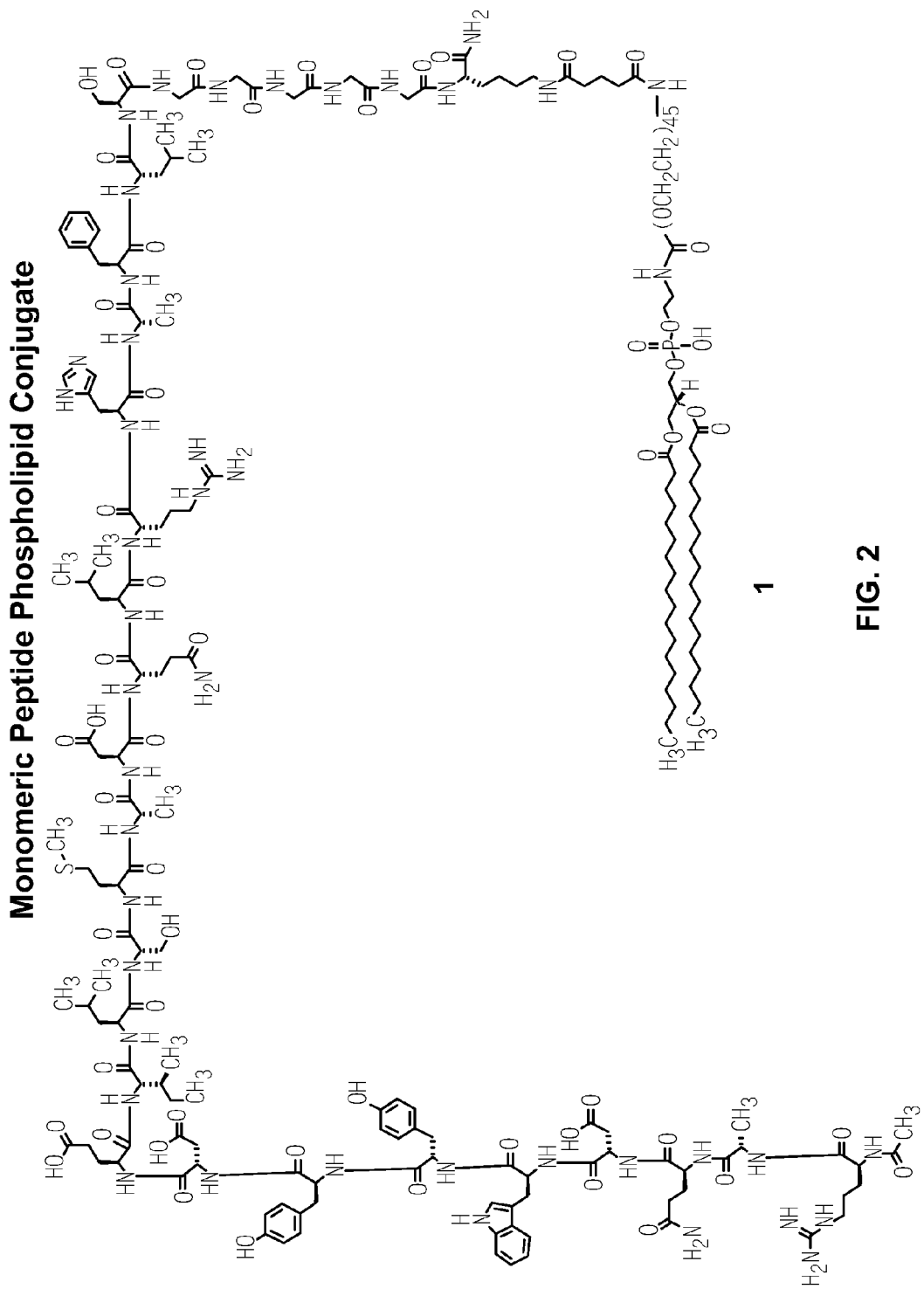
FIG. 2 illustrates a monomeric peptide phospholipid conjugate (1) including a peptide with high binding affinity for KDR.

As shown if FIGS. 1 and 2 the monomeric peptide phospholipid conjugate (1) N-acetyl-L-arginyl-L-alanyl-L-glutaminyl-L-aspartyl-L-tryptophyl-L-tryptophyl-L-aspartyl-L-isoleucyl-L-glutamyl-L-leucyl-L-serinyl-L-methionyl-L-alanyl-L-aspartyl-L-glutaminyl-L-leucyl-L-arginyl-L-histidyl-L-alanyl-Ll- phenylalanyl-L-leucyl-L-serinyl-glycyl-glycyl-glycl-glycyl-glycyl-{N6-[1,2-distearoyl-sn-glycero-3-phosphoethanolaminocarbonyloxy-(PEG2000)-aminoglutaryl]}-L-lysinamide, is a phospholipid conjugate. This conjugate is also referred to as Ac-RAQDWYYDEILSMADQLRHAFLSGGGGGK(DSPE-PEG2000-NH-Glut)-NH₂ (SEQ ID NO. 1) and Ac-Arg-Ala-Gln-Asp-Trp-Tyr-Tyr-Asp-Glu-Ile-Leu-Ser-Met-Ala-Asp-Gln-Leu-Arg-His-Ala-Phe-Leu-Ser-Gly-Gly-Gly-Gly-Gly-Lys(DSPE-PEG2000-NH-Glut)-NH₂. It comprises a 29 amino acid linear peptide monomer (2) N-acetyl-L-arginyl-L-alanyl-L-glutaminyl-L-aspartyl-L-tryptophyl-L-t tophyl-L-aspartyl-L-isoleucyl-L-glutamyl-L-leucyl-L-serinyl-L-methionyl-L-alanyl-L-aspartyl-L-glutaminyl-L-leucyl-L1-arginyl-L-histidyl-L-alanyl-L-phenylalanyl-L-leucyl-L-serinyl-glycyl-glycyl-glycl-glycyl-glycyl-L-lysinamide, also referred to as Ac-RAQDWYYDEILSMADQLRHAFLSGGGGGK-NH₂ (SEQ ID NO. 2) and Ac-Arg-Ala-Gln-Asp-Trp-Tyr-Tyr-Asp-Glu-Ile-Leu-Ser-Met-Ala-Asp-Gln-Leu-Arg-His-Ala-Phe-Leu-Ser-Gly-Gly-Gly-Gly-Gly-Lys-NH₂. This novel peptide monomer binds with high affinity to KDR. It should be understood that analogs and derivatives of the monomeric peptide phospholipid conjugate (1) and the linear peptide monomer (2) are intended to be included within the scope of the present invention.

Figure 9:
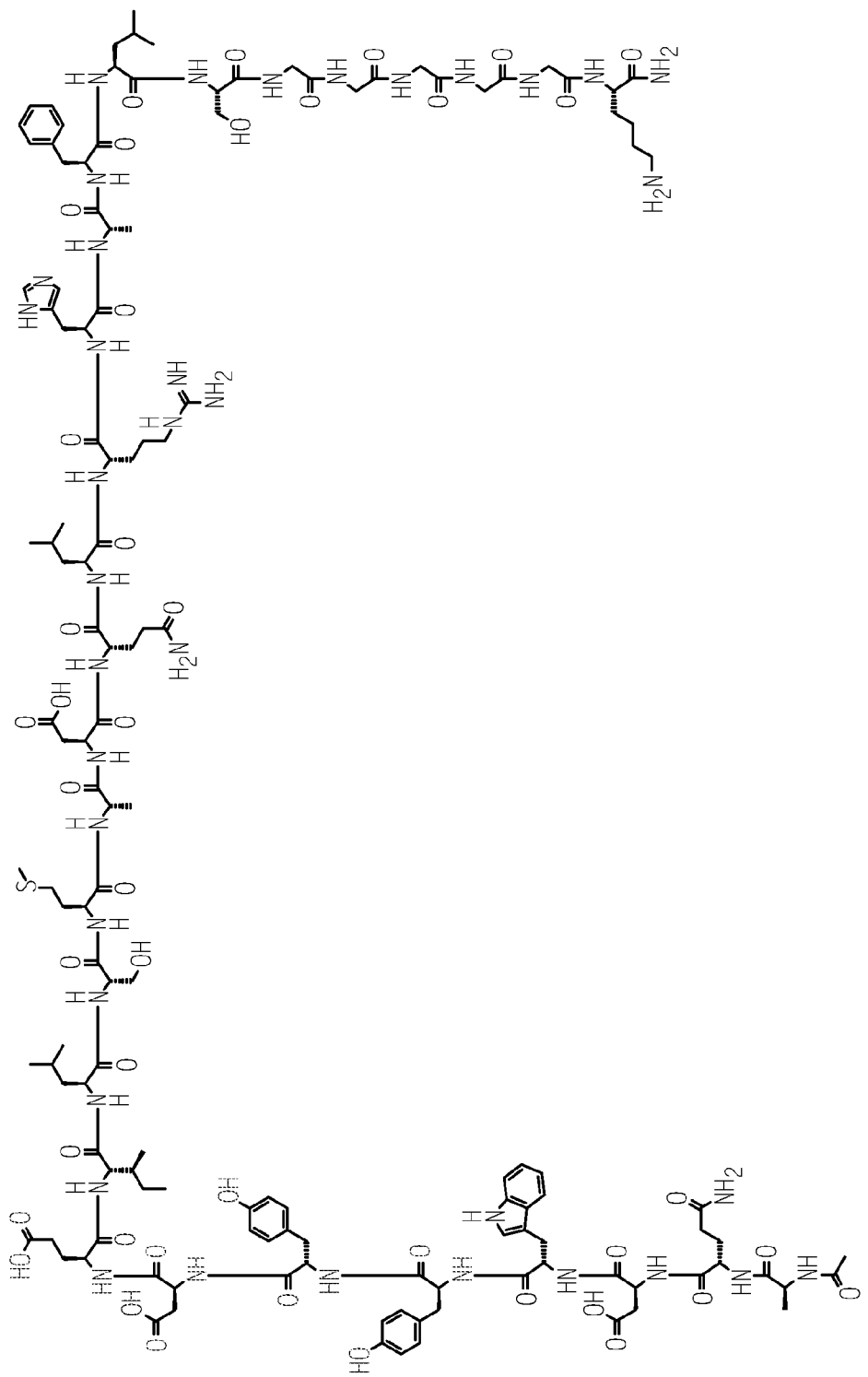
FIG. 9 illustrates another representative monomeric peptide (32) having a high binding affinity for KDR.
Figure 10:
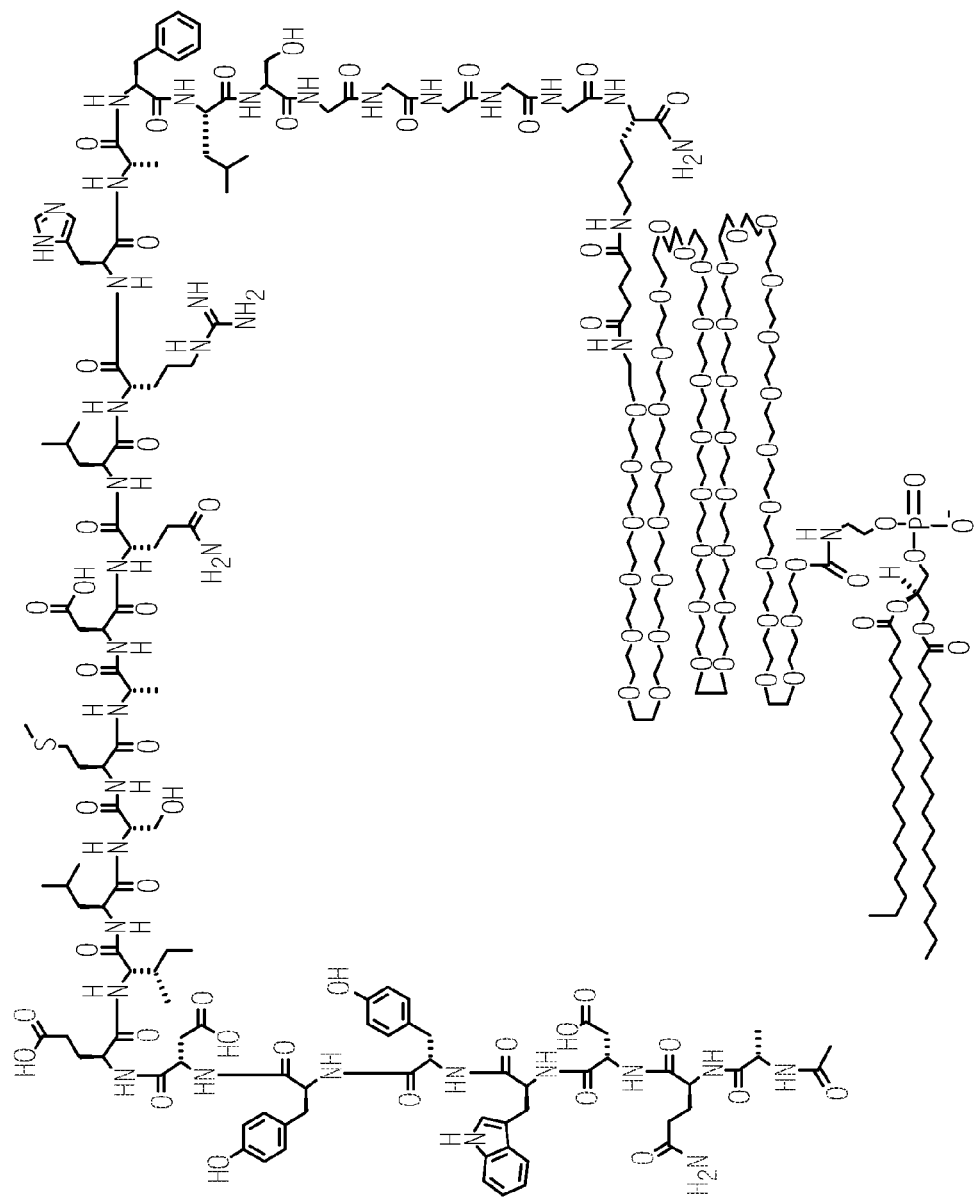
FIG. 10 illustrates another monomeric peptide-phospholipid conjugate (31) which includes the monomeric peptide shown in FIG. 9.

FIG. 10 provides the structure of another monomeric peptide phospholipid conjugate (31), N-acetyl-L-alanyl-L-glutaminyl-L-aspartyl-L-tryptophyl-L-tyrosyl-L-tyrosyl-L-aspartyl-L-glutamyl-L-isoleucyl-L-leucyl-L-seryl-L-methionyl-L-alanyl-L-aspartyl-L-glutamyl-L-leucyl-L-arginyl-L-histidyl- L-alanyl-L-phenylalanyl-L-leucyl-L-seryl-glycyl-glycyl-glycyl-glycyl-glycyl-{N6-[1,2-distearoyl-sn-glycero-3-phosphoethanolaminocarbonyloxy-(PEG2000)-aminoglutaryl]}-L-lysine-amide, a phospholipid conjugate. This conjugate is also referred to as Ac-AQDW-YYDEILSMADQLRHAFLSGGGGGK(DSPE-PEG2000-NH-Glut)-NH₂ (SEQ ID NO. 4) and Ac-Arg-Ala-Gln-Asp-Trp-Tyr-Tyr-Asp-Glu-Ile-Leu-Ser-Met-Ala-Asp-Gln-Leu-Arg-His-Ala-Phe-Leu-Ser-Gly-Gly-Gly-Gly-Gly-Lys (DSPE-PEG2000-NH-Glut)-NH₂. As shown in FIG. 9, the conjugate comprises a 28 amino acid linear peptide monomer (32), N-acetyl-L-alanyl-L-glutaminyl-L-aspartyl-L-tryptophyl-L-tyrosyl-L-tyrosyl-L-aspartyl-L-glutamyl-L-isoleucyl-L-leucyl-L- seryl-L-methionyl-L-alanyl-L-aspartyl-L-glutamyl-L-leucyl-L-arginyl-L-histidyl-L-alanyl-L-phenylalanyl-L-leucyl-L-seryl-glycyl-glycyl-glycyl-glycyl-glycyl-L-lysinamide, which is also referred to as Ac-AQDWYYDEILSMADQLRHAFLSGGGGGK-NH₂ (SEQ ID NO. 5) and Ac-Ala-Gln-Asp-Trp-Tyr-Tyr-Asp-Glu-Ile-Leu-Ser-Met-Ala-Asp-Gln-Leu-Arg-His-Ala-Phe-Leu-Ser-Gly-Gly-Gly-Gly-Gly-Lys-NH₂. As shown in co-pending application, U.S. application Ser. No. 10/661,156, filed Sep. 11, 2003, this peptide monomer binds with high affinity to KDR. It should be understood that analogs and derivatives of the monomeric peptide phospholipid conjugate and the linear peptide monomer are intended to be included within the scope of the present invention.

As shown in the Examples, ultrasound contrast agents such as gas filled microbubbles formulated with the monomeric peptide phospholipid conjugates (1) and (31) displayed high KDR binding which was confirmed using echographic examination of VX2 tumors in rabbits.

Ideally, to facilitate production of the monomeric peptide phospholipid conjugate (1) or (31), the linear peptide monomer (2) or (32) should be prepared in bulk. Then conjugation of the purified linear peptide monomer (2) or (32) to the phospholipid, such as, for example, a pegylated phospholipid in salt form, e.g., DSPE-PEG2000-NH₂ phospholipid ammonium salt (4) via the linker disuccinimidyl glutarate (DSG), may be used to provide monomeric peptide phospholipid conjugates (1) or (32).

Methods of Preparation of Monomer Peptide-Phospholipid Conjugates

In preparing monomeric peptide phospholipid conjugates (1) and (31), methods according to the present invention provide at least the following advantages: increased yield of peptide synthesis; reduced extent of racemization; avoidance of previously observed piperidine amide formation during synthesis, efficient purification of peptide monomers (2) and (32), development of a procedure for conjugation of peptide monomers (2) and (32) on larger scale; and development of purification protocols that would allow the ready separation of the monomeric peptide phospholipid conjugates (1) and (31) from the starting DSPE-PEG2000-NH₂ phospholipid ammonium salt (4).

Monomeric peptide phospholipid conjugates may be prepared as described below. It should be appreciated that the numerical values referred to in this representative description of the synthesis of monomeric peptide phospholipid conjugates are representative.

Linear peptide monomers may be prepared by SPPS. The sequence of the linear peptide monomers may be constructed as a C-terminal carboxamide on Pal-Peg-PS-resin (substitution level: 0.2 mmol/g). Peptide synthesis may be accomplished using Fmoc chemistry on a SONATA®/Pilot Peptide Synthesizer. Problems previously observed with this process have been racemization, incomplete couplings and piperidine amide formation, each of which contribute to suboptimal yield and purity. A dramatic decrease in the formation of the piperidine amide may be attained by the use of 25% piperidine in DMF containing HOBt (0.1M) as the reagent for Fmoc removal. Racemization may be considerably reduced by using DIC/HOBt as the activator for most couplings; a 3 h coupling time using a four-fold excess of pre-activated Fmoc-amino acid with an intervening wash with anhydrous DMF (6×). $N^{\alpha}$-Fmoc amino acids may be dissolved just before their coupling turn and pre-activated with DIC/HOBt in DMF for 4 min and transferred to the reaction vessel. This may be accomplished on the Sonata instrument by loading the solid Fmoc-amino acids into the amino acid vessels of the instrument and then programming the instrument to add DMF, HOBt/DMF and DIC/DMF sequentially with bubbling of the solution.

To optimize the yield, the problem of aggregation of the resin during the synthesis of longer peptides, which can be devastating even when optimal coupling reagents are employed, may be addressed. To reduce aggregation during peptide assembly the strategy of using pseudoproline dipeptides to incorporate X-Thr or X-Ser as dipeptides instead of sequential couplings of X and Thr or X and Ser, may be employed. For linear peptide monomers sequential couplings of $Leu^{11}$-$Ser^{12}$ and $Leu^{22}$-$Ser^{23}$ may be replaced by the single coupling of the pseudoproline dipeptide, Fmoc-Leu-Ser($\psi^{Me,Me}$pro)-OH. Additional optimization may be accomplished by reducing the number of couplings by using Fmoc-Gly-Gly-Gly-OH and Fmoc-Gly-Gly-OH, in lieu of serial coupling of Fmoc-Gly-OH. Activation of -Gly-Gly-OH segments may lead to cyclization of the activated acid function with the distal amide function to produce an inactive diketopiperazine; this may reduce coupling yields in a time dependant manner. This problem may be avoided by addition of Fmoc-$Gly_n$-OH (n=2, 3) to the reaction vessel and sequential addition of HOBt and DIC; the activated Fmoc-$Gly_n$-OH may be intercepted by the resin-bound amino group before appreciable cyclization to the diketopiperazine takes place. With these improvements, the synthesis of linear peptide monomers may be completed on the Sonata Peptide Synthesizer on a 10 mmol synthesis scale.

After chain elongation, the Fmoc may be removed from the N-terminus. The peptide and the free amino group may be acetylated. Then the peptide sequence may be cleaved from the resin and deprotected using "Reagent B" (TFA:water:phenol:triisopropylsilane, 88:5:5:2, v/v/w/v) for 4 h. After the cleavage reaction the crude peptide may be isolated as a solid by evaporation of the volatiles, trituration of the residue with diethyl ether and washing of the solid thus obtained using the same solvent. In another variation the peptide may be precipitated from the reaction mixture by addition of diethyl ether to the reaction mixture, collecting the solid thus formed and washing with the same solvent.

Linear peptide monomers may be purified as described below. Again, the numerical references are representative. Crude linear peptide monomers (0.5 g) may be dissolved in $CH_3CN$ (40 mL/g) and this solution may be diluted to a final volume of 100 mL with water. The solution may then be filtered. The filtered solution may be loaded onto the preparative HPLC column (Waters, XTerra® Prep MS C18, 10µ, 300 Å, 50×250 mm) equilibrated with 10% $CH_3CN$ in water (0.1% TFA). After loading, the composition of the eluent may then be ramped to 20% $CH_3CN$-water (0.1% TFA) over 1 min, and a linear gradient may be initiated at a rate of 0.6%/min of $CH_3CN$ (0.1% TFA) into water (0.1% TFA) and run for 50 min. Eluted fractions may be checked for purity on an analytical reversed phase C18 column (Waters XTerra MS-C18, 10µ, 120 Å, 4.6×50 mm) and fractions containing the product in >95% purity may be combined and freeze-dried. For each purification of 0.5 g of crude peptide 0.12 g (24%) of linear peptide monomer may be consistently isolated and will provide the peptide in the same yield and purity.

Synthesis of monomeric peptide phospholipid conjugates may be performed as described below. The numerical references are again representative. The last step in the synthesis may be the conjugation of the phospholipid, such as, for example, a pegylated phospholipid such as DSPE-PEG2000-$NH_2$ phospholipid ammonium salt to a linear peptide monomer. The PEG2000 moiety of DSPE-PEG2000-$NH_2$ phospholipid ammonium salt (4) is nominally comprised of 45 ethylene glycol units. It should be understood, however, that this material is a distribution of PEG containing species whose centroid is the nominal compound containing 45 ethylenoxy units. The conjugation of a linear peptide monomer with DSPE-PEG2000-$NH_2$ phospholipid ammonium salt may be accomplished by preparation of the glutaric acid monoamide mono NHS ester of a linear peptide monomer and reaction of this with the free amino group of the phospholipid ammonium salt. Thus a linear peptide monomer may be reacted with DSG (4 eq.) in DMF in the presence of DIEA (5 eq.) for 30 min. The reaction mixture may be diluted with ethyl acetate, which may result in precipitation of the peptide glutaric acid monoamide mono-NHS ester. The supernatant containing un-reacted DSG may be decanted and the intermediate peptide mono-NHS ester may be washed several times with ethyl acetate to remove traces of DSG. Mass spectral data confirms the formation of the peptide mono-NHS ester as a clean product. The solid mono-NHS ester may be dissolved in DMF and reacted with DSPE-PEG2000-$NH_2$ phospholipid ammonium salt (0.9 eq.) in the presence of DIEA (4 eq.) for 24 h. The linear peptide monomer glutaric acid monoamide mono-NHS ester may be used in excess to maximize the consumption of the phospholipid ammonium salt because free phospholipid ammonium salt may complicate the isolation of monomeric peptide phospholipid conjugates in highly pure form.

The reaction mixture may be diluted with a 1:1 mixture of water (0.1% TFA) and $CH_3CN$—$CH_3OH$ (1:1, v/v) (0.1% TFA) (~100 mL), applied to a reversed phase C2 column (Kromasil® Prep C2, 10µ, 300 Å, 50×250 mm, flow rate 100 mL/min) and the column may be eluted with a 3:1 mixture of water (0.1% TFA) and $CH_3CN$—$CH_3OH$ (1:1, v/v) (0.1% TFA) to remove hydrophilic impurities. Then the product may be eluted using a gradient of $CH_3CN$—$CH_3OH$ (1:1) (0.1% TFA) into water (0.1% TFA) (see Experimental Section for details). The collected fractions may be analyzed by reversed phase HPLC using an ELS detector which allows the detection of the desired product and the often difficult-to-separate DSPE-PEG2000-$NH_2$ phospholipid which has very little UV absorbance. This indicates the clear separation of the monomeric peptide phospholipid conjugates and DSPE-PEG2000-$NH_2$ phospholipid. The pure product-containing fractions may be collected, concentrated on a rotary evaporator (to reduce the content of methanol) and freeze-dried to provide monomeric peptide phospholipid conjugates as a colorless solid. In order to prepare the required quantity of the monomeric peptide phospholipid conjugates, several runs may be conducted employing 0.5 g to 1.0 g of linear peptide monomer. In all cases the target monomeric peptide phospholipid conjugates may be were isolated in high yield and purity (e.g., 57-60% yield and >99% purity).

Dimer Conjugate

Generally

Figure 3:
FIG. 3 illustrates a method for the production of a precursor dimer peptide (16) from peptide monomers.
Figure 4:
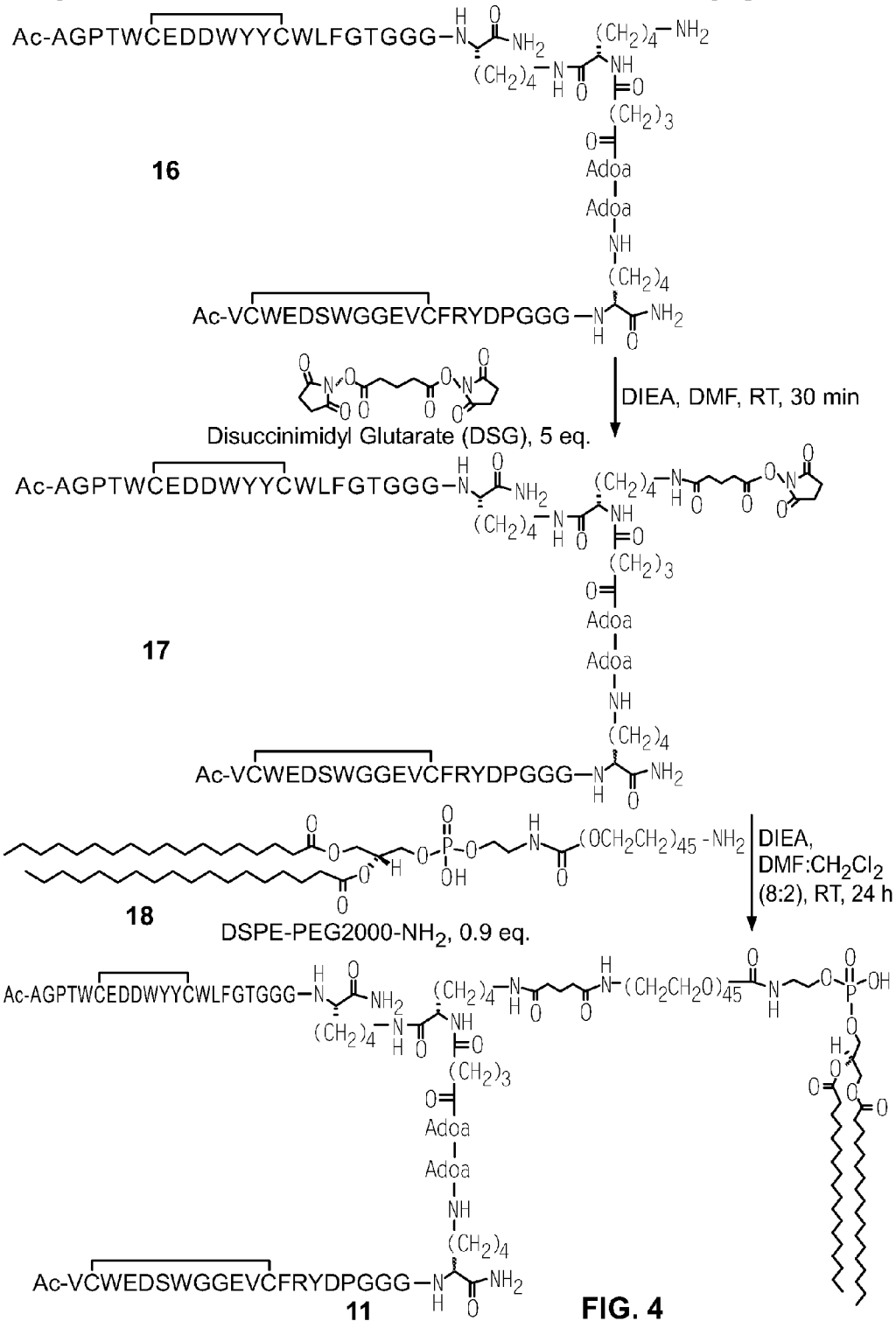
FIG. 4 illustrates a method for the conjugation of the precursor dimer peptide shown in FIG. 1 to DSPE-PEG2000-NH$_2$ to form a dimeric peptide phospholipid conjugate (11) containing peptides which bind with high affinity to KDR.
Figure 5:
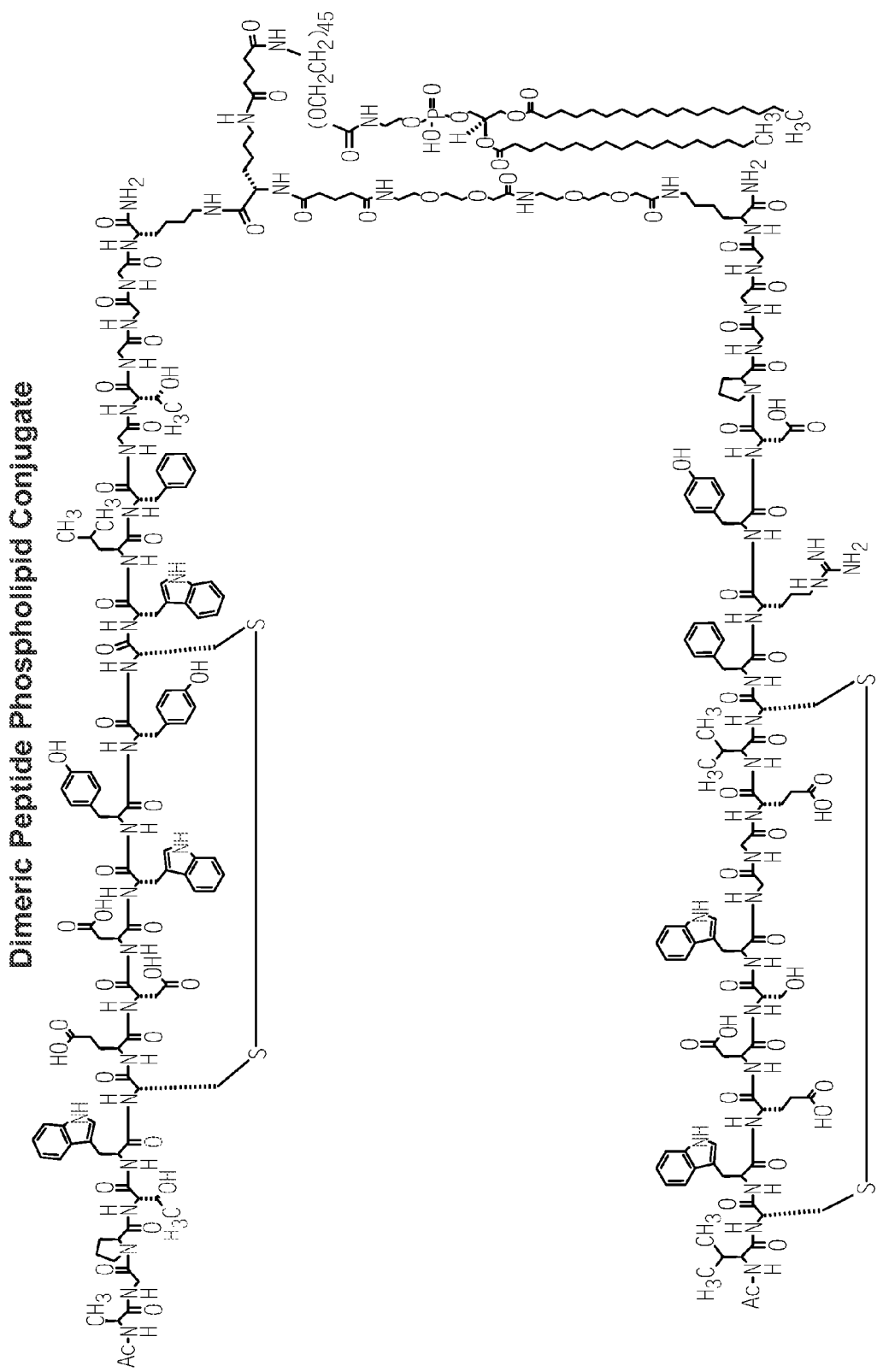
FIG. 5 illustrates a dimeric peptide-phospholipid conjugate (11) containing peptides which bind with high affinity to KDR.

Table 2 provides a description for the identification labels shown in FIGS. 3, 4 and 5.

Ultrasound contrast agents (e.g. gas filled microbubbles) formulated with the dimeric peptide phospholipid conjugate (11) displayed high KDR binding which was confirmed using echographic examination of VX2 tumors in rabbits.

Methods of Preparation of Dimer-Phospholipid Conjugates

To accomplish synthesis of the dimeric peptide phospholipid conjugate (11), the monomers used for this purpose optimally should be prepared in bulk. Then the monomers may be tethered to each other using di-succinimidyl glutarate as a linker to form the precursor dimer peptide (16), Acetyl-

TABLE 2

```
11  Ac-AGPTWCEDDWYYCWLFGTGGGK{Ac-VCWEDSWGGEVCFRYDP-
    GGGK[-Adoa-Adoa-Glut-K(DSPE-PEG2000-NH-Glut)]-NH₂ cyclic (2-12)
    disulfide}-NH₂ cyclic (6-13) disulfide 12  Ac-AGPTWCEDDWYYCWLFGTGGGK[K(ivDde)]-NH₂ cyclic (6-13) disulfide 13  Ac-VCWEDSWGGEVCFRYDPGGGK(Adoa-Adoa)-NH₂ cyclic (2-12) disulfide 14  mono-NHS ester of glutaryl-peptide 12
    Ac-AGPTWCEDDWYYCWLFGTGGGK[NHS-Glut-K(ivDde)]-NH₂ cyclic (6-13)
    disulfide 15  ivDde-bearing dimer
    Ac-AGPTWCEDDWYYCWLFGTGGGK{Ac-VCWEDSWGGEVCFRYDPGGGK[-
    Adoa-Adoa-Glut-K(ivDde)]-NH₂ cyclic (2-12) disulfide}-NH₂ cyclic (6-13) disulfide 16  Ac-AGPTWCEDDWYYCWLFGTGGGK[Ac-VCWEDSWGGEVCFRYDPGGGK(-
    Adoa-Adoa-Glut-K)-NH₂ cyclic (2-12) disulfide]-NH₂ cyclic (6-13) disulfide 17  Mono-NHS ester of glutaryl-peptide 16
    Ac-AGPTWCEDDWYYCWLFGTGGGK{Ac-VCWEDSWGGEVCFRYDPGGGK[-
    Adoa-Adoa-Glut-K(NHS-Glut)]-NH₂ cyclic (2-12) disulfide}-NH₂ cyclic (6-13)
    disulfide 18  DSPE-PEG2000-NH₂ phospholipid
```

As shown in those figures the dimeric peptide phospholipid conjugate (11) Acetyl-L-alanyl-glycyl-L-prolyl-L-threonyl-L-tryptophyl-L-cystinyl-L-glutamyl-L-aspartyl-L-aspartyl-L-tryptophyl-L-tyrosyl-L-tyrosyl-L-cystinyl-L-tryptophyl-1-leucyl-L-phenylalanyl-glycyl-L-threonyl-glycyl-glycyl-glycyl-L-lysyl[Acetyl-L-valyl-L-cystinyl-L-tryptophyl-L-glutamyl-L-aspartyl-L-seryl-L-tryptophyl-glycyl-glycyl-L-glutamyl-L-valyl-L-cystinyl-L-phenylalanyl-L-arginyl-L-tyrosyl-L-aspartyl-L-prolyl-glycyl-glycyl-glycyl-L- lysyl (distearylphosphoethanolaminocarbonoxy-PEG2000-amino-8-amino-3,6-dioxaoctanoyl-8-amino-3,6-dioxaoctanoyl-glutaryl-L-lysyl) amide cyclic (2-12) disulfide]-amide cyclic (6-13) disulfide, consists of two monomeric peptide chains which bind KDR: a 21 amino acid cyclic disulfide peptide monomer (13) Acetyl-L-valyl-L-cystinyl-L-tryptophyl-L-glutamyl-L-aspartyl-L-seryl-L-tryptophyl-glycyl-glycyl-L-glutamyl-L-valyl-L-cystinyl-L-phenylalanyl-L-arginyl-L-tyrosyl-L-aspartyl-L-prolyl-glycyl-glycyl-glycyl-L-lysyl(8-amino-3,6-dioxaoctanoyl-8-amino-3,6-dioxaoctanoyl)amide cyclic (2-12) disulfide, and a 22 amino acid cyclic disulfide peptide monomer (12) Acetyl-L-alanyl-glycyl-L-prolyl-L-threonyl-L-tryptophyl-L-cystinyl-L-glutamyl-L-aspartyl-L-aspartyl-L-tryptophyl-L-tyrosyl-L-tyrosyl-L-cystinyl-L-tryptophyl-L-leucyl-L-phenylalanyl-glycyl-L-threonyl- glycyl-glycyl-glycyl-L-lysinamide cyclic 6-13 disulfide tethered by a glutaryl linker. It should be understood that analogs and derivatives of the dimeric peptide phospholipid conjugate (11) and the cyclic disulfide peptide monomers (12) and (13) are intended to be included within the scope of the present invention.

L-alanyl-glycyl-L-prolyl-L-threonyl-L-tryptophyl-L-cystinyl-L-glutamyl-L-aspartyl-L-aspartyl-L-tryptophyl-L-tyrosyl-L-tyrosyl-L-cystinyl-L-tryptophyl-L-leucyl-L-phenylalanyl-glycyl-L-threonyl- glycyl-glycyl-glycyl-L-lysyl[Acetyl-L-valyl-L-cystinyl-L-tryptophyl-L-glutamyl-L-aspartyl-L-seryl-L-tryptophyl-glycyl-glycyl-L-glutamyl-L-valyl-L-cystinyl-L-phenylalanyl-L-arginyl-L-tyrosyl-L-aspartyl-L-prolyl-glycyl-glycyl-glycyl-L-lysyl(8- amino-3, 6-dioxaoctanoyl-8-amino-3,6-dioxaoctanoyl-glutaryl-L-lysyl) amide cyclic (2-12) disulfide]-amide cyclic (6-13) disulfide. Then conjugation of the purified precursor dimer peptide (16) to a DSPE-PEG2000-NH₂ phospholipid ammonium salt (18) again via disuccinimidyl glutarate may be used in order to provide the target dimeric peptide phospholipid conjugate (11).

In preparing dimeric peptide phospholipid conjugate (11), methods according to the present invention provide at least the following advantages: increased yield of automated chain elongation of the peptide sequences; reduced extent of racemization encountered during synthesis; avoidance of previously observed piperidine amide formation during synthesis of peptide monomer (13); cyclization of linear di-cysteine containing peptide precursors of (12) and (13) using procedures amenable to multigram scale yet allowing efficient and practical sample handling; efficient purification of monomer peptides (12) and (13); maximized yield and purity of precursor dimer peptide (16); development of a procedure for conjugation of the precursor dimer peptide (16) on larger scale; and development of purification protocols that would allow the ready separation of the target dimeric peptide phospholipid conjugate (11) from phospholipid ammonium salt (18).

The dimeric peptide phospholipid conjugate (11) may be prepared by automated synthesis of the peptide monomers (12), Ac-Ala-Gly-Pro-Thr-Trp-Cys-Glu-Asp-Asp-Trp-Tyr-Tyr-Cys-Trp-Leu-Phe-Gly-Thr-Gly-Gly-Gly-Lys(ivDde)-NH$_2$ cyclic (6-13) disulfide, and (13), Ac-Val-Cys-Trp-Glu-Asp-Ser-Trp-Gly-Gly-Glu-Val-Cys-Phe-Arg-Tyr-Asp-Pro-Gly-Gly-Gly-Lys(Adoa-Adoa)-NH$_2$ cyclic (2-12) disulfide, their efficient coupling using disuccinimidyl glutarate (DSG) to give an ivDde-protected dimer, its deprotection and subsequent coupling to DSPE-PEG2000-NH$_2$, also via a glutaryl linkage. Using procedures according to the present invention, monomer peptides may be synthesized on a 10 mmol scale without complication and after HPLC purification may be obtained in about 20% yield and >95% purity. Such methods allow dimer formation reactions and the subsequent conjugation to the phospholipid component providing formation of dimeric peptide phospholipid conjugate (11) to be carried out on a gram scale. The precursor dimer peptide (16) may be obtained from the monomer peptides routinely in about 32% yield and >95% purity. The dimeric peptide phospholipid conjugate (11) may be produced from the precursor dimer peptide (16) in 57-60% yield and >99% purity.

Dimeric peptide phospholipid conjugates may be prepared as described below. It should be appreciated that the numerical values referred to in this representative description of the synthesis of dimeric peptide phospholipid conjugates are representative.

Described below is a representative method for the solid phase synthesis and disulfide cyclization of a peptide monomer (12) Ac-Ala-Gly-Pro-Thr-Trp-Cys-Glu-Asp-Asp-Trp-Tyr-Tyr-Cys-Trp-Leu-Phe-Gly-Thr-Gly-Gly-Gly-Lys (ivDde)-NH$_2$ cyclic (6-13) disulfide, and a peptide monomer (13), Ac-Val-Cys-Trp-Glu-Asp-Ser-Trp-Gly-Gly-Glu-Val-Cys-Phe-Arg-Tyr-Asp-Pro-Gly-Gly-Gly-Lys(Adoa-Adoa)-NH$_2$ cyclic (2-12) disulfide.

The peptides may be constructed as their C-terminal carboxamides on Pal-Peg-PS-resin (substitution level: 0.2 mmol/g). Chain elongation may be accomplished using Fmoc chemistry employing optimized deprotection and coupling protocols on a SONATA®/Pilot Peptide Synthesizer on a 10 mmol synthesis scale. The optimized synthesis of the peptides by automated SPSS may be developed by study of peptide impurities and the effect of changes of particular elements of the protocols on the overall yield and purity of the peptides obtained.

Analysis of the impurities obtained from nonoptimized syntheses of the monomer peptides indicates that the major problems are racemization, incomplete couplings and piperidine amide formation (presumably via an intermediate aspartimide or glutarimide intermediate), each of which contributes to suboptimal yield and purity. A dramatic decrease in formation of the piperidine amide may be attained by the use of 25% piperidine in DMF containing HOBt (0.1M) as the reagent for fmoc removal. Racemization may be considerably reduced by using DIC/HOBt as the activator for most couplings; and a 3 h coupling time using a four-fold excess of pre-activated Fmoc-amino acid with an intervening wash with anhydrous DMF (6×). N-$^\alpha$Fmoc amino acids may be dissolved just before their coupling turn and pre-activated with DIC/HOBt in DMF for 4 min and transferred to the reaction vessel. This may be accomplished on the Sonata instrument by loading the solid Fmoc-amino acids into the amino acid vessels of the instrument and then programming the instrument to add DMF, HOBt/DMF and DIC/DMF sequentially with bubbling of the solution after each addition.

To optimize the yield, the problem of aggregation of the resin during the synthesis of longer peptides, which can be devastating even when optimal coupling reagents are employed, may be addressed. To reduce aggregation during peptide assembly the strategy of using pseudoproline dipeptides to incorporate X-Thr or X-Ser (X refers to the n−1 amino acid of the sequence) as dipeptides instead of sequential couplings of X and Thr or X and Ser, may be employed. Thus, for the monomer (12), Ac-Ala-Gly-Pro-Thr-Trp-Cys-Glu-Asp-Asp-Trp-Tyr-Tyr-Cys-Trp-Leu-Phe-Gly-Thr-Gly-Gly-Gly-Lys(ivDde)-NH$_2$ cyclic (6-13) disulfide, sequential coupling of suitably protected Thr and Gly (shown in bold above) may be replaced by the single coupling of the pseudoproline dipeptide, Fmoc-Gly-Thr($\psi^{Me,Me}$pro)-OH. Similarly, in the synthesis of the monomer (13), Ac-Val-Cys-Trp-Glu-Asp-Ser-Trp-Gly-Gly-Glu-Val-Cys-Phe-Arg-Tyr-Asp-Pro-Gly-Gly-Gly-Lys(Adoa-Adoa)-NH$_2$ cyclic (2-12) disulfide, the pseudoproline dipeptide, Fmoc-Asp(OtBu)-Ser($\psi^{Me,Me}$pro)-OH may be employed to replace the sequential coupling of suitably protected Ser and Asp (shown in bold font above). Further optimization may be accomplished by reducing the number of couplings by using Fmoc-Gly-Gly-Gly-OH and Fmoc-Gly-Gly-OH, in lieu of serial coupling of Fmoc-Gly-OH. Activation of -Gly-Gly-OH segments can lead to cyclization of the activated acid function with the distal amide function to produce an inactive diketopiperazine; this may reduce coupling yields in a time dependant manner. This problem may be avoided by addition of Fmoc-Gly$_n$-OH (n=2, 3) to the reaction vessel and sequential addition of HOBt and DIC; the activated Fmoc-Gly$_n$-OH may be intercepted by the resin-bound amino group before appreciable cyclization to the diketopiperazine takes place. After chain elongation is completed the N-terminal Fmoc protecting group may be removed from each of the peptides and the free amino group may be acetylated.

The pseudo-orthogonally protected derivative, Fmoc-Lys (ivDde)-OH may be used to enable the selective unmasking of the ε-amine of the C-terminal lysine of the monomer and dimer peptides and their subsequent functionalization, which also may be optimized. The ivDde group on the ε-amine of the C-terminal lysine of each of the peptide monomers may be removed using 10% hydrazine in DMF. Then Fmoc-Adoa, for monomer (13) or Lys(ivDde) for monomer (12) may be appended to the exposed lysine ε-amino group using 4 equivalents of the Fmoc amino acid and 4 equivalents each of DIC and HOBt in DMF for 10 h. After completion of the synthesis, the peptide sequence may be cleaved from the resin and deprotected using "Reagent B" (TFA:water:phenol:triisopropylsilane, 88:5:5:2, v/v/w/v) for 4 h. After the cleavage reaction was complete the peptide may be precipitated, washed with diethyl ether and dried.

The following procedures for cyclization of the linear di-cysteine containing peptides may be used to provide optimal scale-up of monomer peptides. Generally the aerial oxidation of linear di-cysteine peptides may be carried out at ca 0.5-5 mg/mL (for the disclosed peptide monomers ~0.18-1.8 mM in peptide, ~0.36-3.6 mM in cysteine thiol). In order to work at significantly higher concentrations DMSO-assisted cyclization of di-cysteine peptides allows the cyclization of ~10 g of the linear peptides in good yields in as little as ~50 mL of solution. Therefore the crude linear di-cysteine peptides may be cyclized in 95% DMSO-H$_2$O (5 mL/g) at pH 8.5 at ambient temperature. The progress of the cyclization may be routinely followed by mass spectroscopy and HPLC. Although cyclization may be essentially complete in ~36 h, the reaction mixture may be generally stirred for up to 48 h. The cyclic disulfide peptides may be precipitated from the reaction mixture by dilution with CH$_3$CN and the resulting off-white crude solid peptides may be collected by filtration. This is a convenient method for removing DMSO from the crude cyclic peptide.

Purification and isolation of monomer peptide (12), Ac-AGPTWC*EDDWYYC*WLFGTGGGK [K(ivDde)]-NH$_2$ may be accomplished as described below. Note that as used herein the designation "C*" refers to a cysteine residue that contributes to a disulfide bond. Attempts to dissolve 0.5 g of the crude peptide in up to 300 mL of 30% CH$_3$CN in water (0.1% TFA) have been unsuccessful. Therefore, as an alternative, the crude peptide, (0.5 g) may be dissolved in DMSO (5 mL/g) and this solution may be diluted to a final volume of 100 mL with 20% CH$_3$CN-water. The solution may be filtered. The filtered solution may be loaded onto the preparative HPLC column (Waters, XTerra® Prep MS C18, 10μ, 300 Å, 50×250 mm) equilibrated with 10% CH$_3$CN (0.1% TFA) in water (0.1% TFA), and the column may be eluted with 10% CH$_3$CN (0.1% TFA) in water (0.1% TFA) to wash DMSO from the column. The composition of the eluent then may be ramped to 35% CH$_3$CN-water (0.1% TFA) over 1 min, and a linear gradient may be initiated at a rate of 0.5%/min of CH$_3$CN (0.1% TFA) into water (0.1% TFA) and run for 50 min. Eluted fractions may be checked for purity on an analytical reversed phase C18 column (Waters XTerra MS-C18, 10μ, 120 Å, 4.6×50 mm) and fractions containing the product in >95% purity may be combined and freeze-dried. For each purification of 0.5 g of crude peptide 0.1 g (20%) for (12), Ac-AGPTWC*EDDWYYC*WLFGTGGGK [K(ivDde)]-NH$_2$ may be isolated. Repeat purifications have been found to provide the peptide consistently in the same yield and purity.

The peptide monomer (13), Ac-VC*WEDSWGGEVC*FRYDPGGGK(Adoa-Adoa)-NH$_2$ may be purified and isolated as described for peptide monomer (12) except that the subject peptide may be dissolved in 20% CH$_3$CN (0.1% TFA) in 0.1% aqueous TFA (0.5 g peptide/100 mL) instead of a DMSO-containing diluent. The resulting solution of crude peptide may be loaded onto the preparative HPLC column (Waters, XTerra® Prep MS C18, 10μ, 300 Å, 50×250 mm, flow rate 100 mL/min) equilibrated with 10% CH$_3$CN in water (0.1% TFA). The column may be eluted with 10% CH$_3$CN (0.1% TFA)/water (0.1% TFA) at 100 mL/min for 5 min. Then the composition of the eluent may be ramped to 30% CH$_3$CN (0.1% TFA)/water (0.1% TFA) over 1 min and a linear gradient rate of 0.5%/min of CH$_3$CN (0.1% TFA) into water (0.1% TFA) may be initiated, and maintained until the desired peptide is completely eluted from the column. Product-containing fractions may be analyzed on a Waters XTerra analytical reversed phase C-18 column (10μ, 120 Å) and fractions containing the product in >95% purity may be pooled and freeze-dried to afford the cyclic disulfide peptide monomer (13) (0.12 g, 24% yield) in >95% purity. The 10 g of crude peptide monomer may be purified serially in this manner.

Described below is a representative method for preparing the precursor dimer peptide (16), Ac-AGPTWCEDDWYY-CWLFGTGGGK[Ac-VCWEDSWGGEVCFRYDPGGGK(-Adoa-Adoa-Glut-K)][-NH$_2$ cyclic (2-12) disulfide]-NH$_2$ cyclic (6-13) disulfide. The preparation of the precursor dimer peptide may be accomplished by the tethering of the monomer peptides in a two step procedure. First, Ac-AGPTWC*EDDWYYC*WLFGTGGGK-[K(ivDde)]-NH$_2$ (12) may be reacted with disuccinimidyl glutarate (DSG, 5 eq.) in DMF in the presence of DIEA (5 eq.) for 30 min. The reaction mixture may be diluted with ethyl acetate, which results in precipitation of the glutaric acid monoamide mono-NHS ester of the peptide. The supernatant, containing unreacted DSG, may be decanted and the mono-NHS ester may be washed several times with ethyl acetate to remove traces of DSG. Mass spectral data confirms the formation of the mono-NHS ester as a clean product. This may be redissolved in DMF and reacted with monomer peptide Ac-VC*WEDSWGGEVC*FRYDPGGGK(Adoa-Adoa)-NH$_2$ (13) in the presence of DIEA (5 eq). HPLC and MS results indicate the formation of the ivDde-bearing dimer, as a single major product. The ivDde protecting group on the ϵ-amine of Lys of the dimer may be removed by stirring the reaction mixture with hydrazine (10%) in DMF for 20 min. The solution then may be acidified with TFA and diluted with 10% CH$_3$CN (0.1% TFA)-water (0.1% TFA), applied to a preparative reversed phase C18 HPLC column and purified by a gradient elution of acetonitrile (0.1% TFA) into 0.1% aqueous TFA. In order to provide the needed quantity of the precursor dimer peptide, the reaction may be conducted employing from 0.5 g to as much as 1 g of each of the monomer peptides. In every case the required precursor dimer peptide may be isolated in ~32% yield and >95% purity confirming the reproducibility and scalability of the procedures.

The final step in the synthesis may be the conjugation of DSPE-PEG2000-NH$_2$ phospholipid ammonium salt (18) to the precursor dimer peptide. As mentioned previously, the PEG2000 moiety of DSPE-PEG2000-NH$_2$ is nominally comprised of 45 ethylene glycol units. It should be understood, however, that this material is a distribution of PEG containing species whose centroid is the nominal compound containing 45 ethylenoxy units.

Conjugation of the DSPE-PEG2000-NH$_2$ to the precursor dimer peptide may be accomplished by preparation of a glutaric acid monoamide mono NHS ester of the precursor dimer and reaction of this with the free amino group of the phospholipid ammonium salt. Thus the ivDde bearing precursor dimer peptide (16) may be reacted with DSG (4 eq.) in DMF in the presence of DIEA (5 eq.) for 30 min. As in the preparation of the precursor dimer peptide the solution may be diluted with ethyl acetate to precipitate the glutaric acid monoamide mono-NHS ester of the dimer (17), as a solid. The supernatant may be decanted to remove the un-reacted DSG. The solid glutaric acid monoamide mono-NHS ester of the dimer peptide (17) may then be washed several times with ethyl acetate to remove traces of DSG. Mass spectral results confirm the formation of the glutaric acid monoamide mono-NHS ester of the peptide dimer as a clean product.

The dimer glutaric acid monoamide mono-NHS ester (17) may be dissolved in DMF-CH$_2$Cl$_2$ (8:2) and reacted with DSPE-PEG2000-NH$_2$ phospholipid ammonium salt (0.9 eq.) in the presence of DIEA (4 eq.) for 24 h. The NHS ester (17) may be used in excess to maximize the consumption of the phospholipid ammonium salt because any free phospholipid may complicate the purification and isolation of the final product. The reaction mixture may be diluted with water (0.1% TFA)-CH$_3$CN—CH$_3$OH (1:1) (0.1% TFA) (~100 mL), applied to a reversed phase C4 column (Kromasil® Prep C4, 10μ, 300 Å, 50×250 mm, flow rate 100 mL/min) and the column may be eluted with water (0.1% TFA)-CH$_3$CN—CH$_3$OH (1:1) (0.1% TFA) solvent mixture to remove hydrophilic impurities. Then the product may be eluted using a gradient of CH$_3$CN—CH$_3$OH (1:1) (0.1% TFA) into water (0.1% TFA). The collected fractions may be analyzed by reversed phase HPLC using an ELS detector which allows the detection of the desired product and the often difficult to separate DSPE-PEG2000-NH$_2$ phospholipid ammonium salt which has no strong UV chromophore. This indicates the clear separation of dimeric peptide phospholipid conjugate and DSPE-PEG2000-NH$_2$ phospholipid ammonium salt. The pure product-containing fractions may be collected, concentrated on a rotary evaporator (to reduce the content of methanol) and freeze-dried to provide the dimer peptide phospholipid conjugate as a colorless solid.

In order to prepare the required quantity of the dimer peptide phospholipid conjugate, several runs may be conducted employing 0.5 g to 1.0 g of the precursor dimer peptide. In all cases the target dimer peptide phospholipid conjugate may be isolated in 57-60% yield and in >99% purity. The bulk quantity of dimer peptide phospholipid conjugate, obtained from the serial runs described above may be obtained by dissolution of the product from the individual runs in t-butanol-acetonitrile-water (1:1:3) followed by lyophilization. The procedure of Ellman for quantitative estimation of free thiol may be applied to the bulk sample of the dimeric peptide phospholipid conjugate; free thiol, if present will be below the limit of detection. Amino acid composition analysis gives results within the acceptable limits, supporting the assigned structure of the peptide derivative. MALDI-TOF mass spectral analysis also supports the presumed structure of the dimeric peptide phospholipid conjugate.

Methods of Preparation of Dimer-Phospholipid Conjugates Having Low or Negligible Levels of TFA The present invention also provides methods for producing dimeric peptide-phospholipid conjugates having very low levels of TFA. While certain methods provide for the synthesis and purification of such conjugates on a gram scale, formation of a lyso-version of the conjugates has been observed upon storage of lyophilized material at 5° C. or upon storage of aqueous solutions of the conjugates. It is believed that the lyso-compound is formed by TFA-promoted acid hydrolysis of one of the phospholipid fatty acid esters in dimer peptide-phospholipid conjugates.

To obtain the phospholipid peptide as a stable material bearing a pharmaceutically acceptable counterion, highly efficient methods for obtaining dimer peptide-phospholipid conjugates were discovered which convert the TFA salts of the dimer peptide-phospholipid conjugate, or any suitable precursor(s), to analogous pharmaceutical acetate salt(s). Representative embodiments of these methods are provided below.

Figure 6:
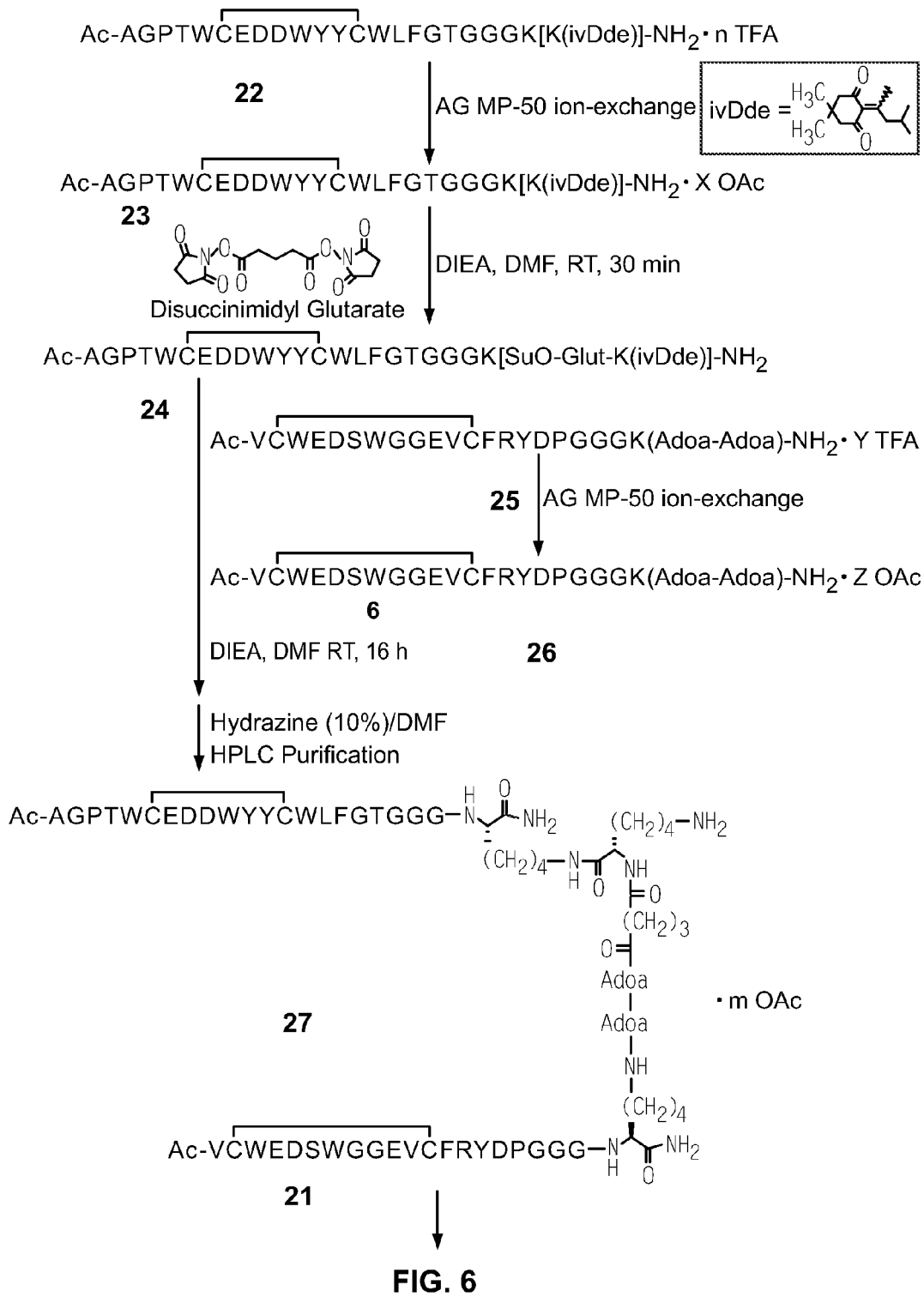
FIG. 6 illustrates a method for the production of dimer peptide-phospholipid conjugates (such as (21)) having minimal levels of TFA.
Figure 7:
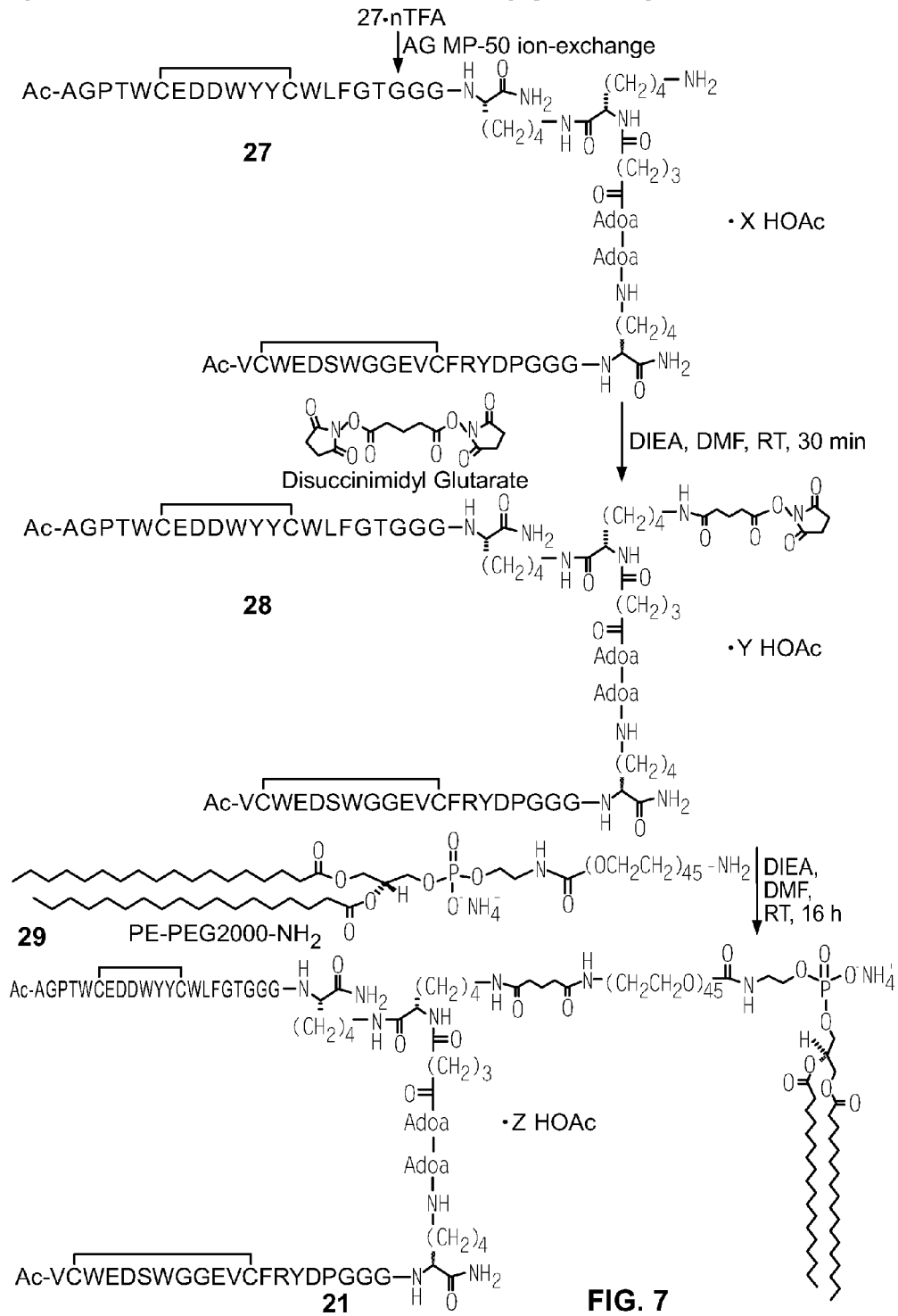
FIG. 7 illustrates another method for the production of dimer peptide-phospholipid conjugates (such as (21)) having minimal levels of TFA.
Figure 8:
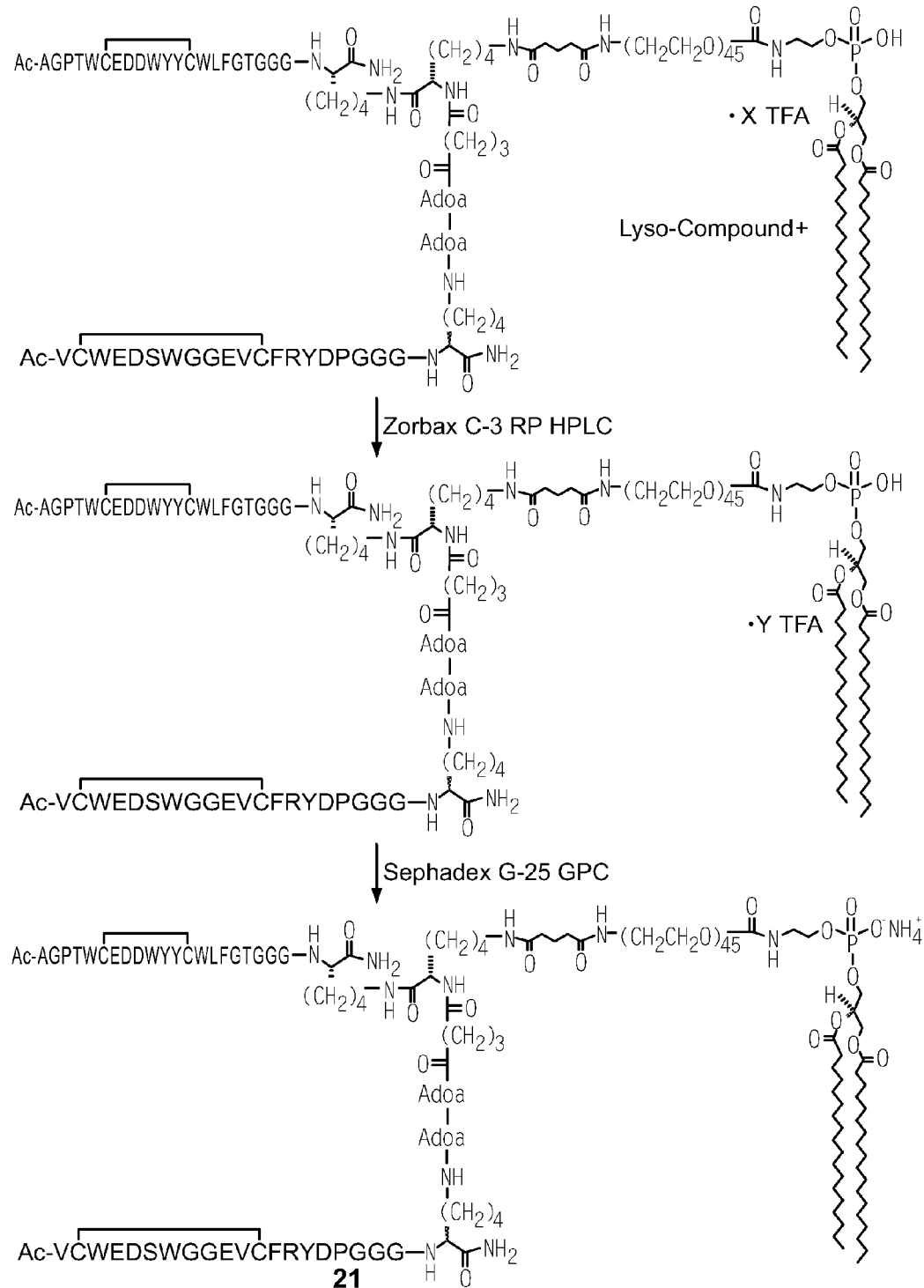
FIG. 8 illustrates another method for the production of dimer peptide-phospholipid conjugates having minimal levels of TFA.

Table 3 provides a description for the identification labels shown in FIGS. 6, 7 and 8.

TABLE 3

| | |
|---|---|
| 21 | Ac-AGPTWCEDDWYYCWLFGTGGGK{Ac-VCWEDSWGGEVCFRYDPGGGK[-Adoa-Adoa-Glut-K(DSPE-PEG2000-NH-Glut)]-$NH_2$ cyclic (2-12) disulfide}-$NH_2$ cyclic (6-13) disulfide |
| 22 | Ac-AGPTWCEDDWYYCWLFGTGGGK[K(ivDde)]-$NH_2$ cyclic (2-12) disulfide • nTFA |
| 23 | Ac-AGPTWCEDDWYYCWLFGTGGGK[K(ivDde)]-$NH_2$ cyclic (2-12) disulfide • xHOAc |
| 24 | mono-NHS ester of glutaryl-peptide 23 Ac-AGPTWCEDDWYYCWLFGTGGGK[NHS-Glut-K(ivDde)]-$NH_2$ cyclic (2-12) disulfide |
| 25 | Ac-VCWEDSWGGEVCFRYDPGGGK(Adoa-Adoa)-$NH_2$ cyclic (2-12) disulfide • yTFA |
| 26 | Ac-VCWEDSWGGEVCFRYDPGGGK(Adoa-Adoa)-$NH_2$ cyclic (2-12) disulfide • zHOAc |
| 27 | Ac-AGPTWCEDDWYYCWLFGTGGGK[Ac-VCWEDSWGGEVCFRYDPGGGK(-Adoa-Adoa-Glut-K)-$NH_2$ cyclic (2-12) disulfide]-$NH_2$ cyclic (6-13) disulfide • X HOAc |
| 28 | Mono-NHS ester of glutaryl-peptide 27 Ac-AGPTWCEDDWYYCWLFGTGGGK{Ac-VCWEDSWGGEVCFRYDPGGGK(-Adoa-Adoa-Glut-K(NHS-Glut)]-$NH_2$ cyclic (2-12) disulfide}-$NH_2$ cyclic (6-13) disulfide |
| 29 | DSPE-PEG2000-$NH_2$ |

Where m, n, x, y, z are variable depending on lyophilization conditions.

Referring now to FIGS. 6 and 7, in certain embodiments monomer peptide components of heterodimer peptide (27), namely TFA salts compounds (22) and (25), are subjected to ion exchange chromatography on the macroporous sulfonic acid cation exchange resin AG MP-50 using a step gradient of ammonium acetate to convert them to their acetate salts. Then the two peptide monomer acetates (23) and (26) may be tethered through a glutaryl linker to form the dimer (27) as an acetate salt. Purification of the crude dimer acetate salt of (27), by C-18 preparative HPLC using a linear gradient method employing $CH_3CN/H_2O$ each containing 10 mM $NH_4OAc$ provides the pure dimer acetate (27). Conjugation of this dimer to DSPE-PEG2000-$NH_2$ (29) and final purification of the crude mixture by C-3 preparative HPLC using $CH_3CN/H_2O/NH_4OAc$ provides compound (21) as the acetate salt.

More specifically, compounds (22), (25) and (27) all bear side-chain carboxylic acid and amino groups. AG MP-50, a macroporous cation-exchange resin, may be used to allow full penetration of the resin by the peptides and to exploit the immobilization of the peptides via their basic (amino and guanidine groups). TFA salts of the peptides may be adsorbed to an AG MP-50 column (sulfonic acid form) and the column may be washed with water and then eluted with a step gradient of $NH_4OAc$ in 0 or 30% $CH_3CN/H_2O$, depending on the solubility of the peptides. The peptides may be eluted at about 600 mM $NH_4OAc$ and the acetate form of the peptides then may be obtained in pure form. Both IC fluorine analysis and CE TFA counter-ion analysis consistently show very low TFA content of the peptides.

Preferred methods also include redissolution/relyophilization of the final peptides several times to remove residual NH$_4$OAc. Otherwise, residual traces of NH$_4$OAc present in the peptides may give rise to free ammonia in the presence of DIEA. This may result in the formation of unwanted peptide-Glut-amide as a major product in subsequent preparation of (27) from the monomers (23) and (26) or final phospholipid-peptide conjugate (21) from the acetate salt of (27).

Referring now to FIG. 7, another embodiment provides the conversion of the TFA salt of dimer (27) to its analogous acetate salt by ion exchange chromatography on the macroporous sulfonic acid cation exchange resin AG MP-50. This dimer acetate then may be conjugated with DSPE-PEG2000-NH$_2$ followed by purification of the crude material by C-3 preparative column using CH$_3$CN/H$_2$O/NH$_4$OAc to give the final compound (21) as an acetate salt.

While the methods described above and in FIGS. 6 and 7 provide excellent results, the second approach has the advantage of requiring fewer steps. Additional details are provided below in the Examples section.

Turning to FIG. 8, another embodiment provides methods for providing dimeric conjugates having minimal amounts of TFA utilizing the size differential between the phospholipid-peptide conjugate (21) and TFA ions. In this embodiment 21●nTFA adduct may be eluted down a size exclusion column in the presence of ammonium bicarbonate buffer. The crude 21●nTFA initially may be freed of the lyso-compound by preparative HPLC on a Zorbax C-3 column using a linear gradient of acetonitrile into water. Both phases may be buffered with 10 mM ammonium acetate. This provides separation of the lyso-compound as indicated by analytical HPLC.

To further reduce the amount of TFA, the material may be applied to a Sephadex G-25 column and eluted with aqueous ammonium bicarbonate solution. The eluate may be monitored by HPLC. Product-containing fractions may be pooled and lyophilized to afford the desired material (21) essentially free of TFA and with high recovery rates. Additional detail is provided below in the Examples section.

Both the monomeric and dimeric peptide phospholipid conjugates described herein may be incorporated into ultrasound contrast agents such as, for example, gas filled microvesicles. Such gas filled microvesicles include, for example, gas filled microbubbles, gas filled microballoons, gas filled microcapsules, etc. In a preferred embodiment, the peptide phospholipid conjugates may be incorporated into ultrasound contrast agents comprising gas filled microbubbles. Methods of preparation of gas filled microbubbles from phospholipids and phospholipid conjugates are known to those skilled in the art. For example, microbubbles according to the present invention can be prepared by methods described in any one of the following patents: EP 554213, WO 04/069284, U.S. Pat. No. 5,413,774, U.S. Pat. No. 5,578,292, EP 744962, EP 682530, U.S. Pat. No. 5,556,610, U.S. Pat. No. 5,846,518, U.S. Pat. No. 6,183,725, EP 474833, U.S. Pat. No. 5,271,928, U.S. Pat. No. 5,380,519, U.S. Pat. No. 5,531,980, U.S. Pat. No. 5,567,414, U.S. Pat. No. 5,658,551, U.S. Pat. No. 5,643,553, U.S. Pat. No. 5,911,972, U.S. Pat. No. 6,110,443, U.S. Pat. No. 6,136,293, EP 619743, U.S. Pat. No. 5,445,813, U.S. Pat. No. 5,597,549, U.S. Pat. No. 5,686,060, U.S. Pat. No. 6,187,288, and U.S. Pat. No. 5,908,610, which are incorporated by reference herein in their entirety. The methods disclosed in WO 04/069284 are particularly preferred.

Suitable phospholipids include esters of glycerol with one or two molecules of fatty acids (the same or different) and phosphoric acid, wherein the phosphoric acid residue is in turn bonded to a hydrophilic group, such as choline, serine, inositol, glycerol, ethanolamine, and the like groups. Fatty acids present in the phospholipids are in general long chain aliphatic acids, typically containing from 12 to 24 carbon atoms, preferably from 14 to 22, that may be saturated or may contain one or more unsaturations. Examples of suitable fatty acids are lauric acid, myristic acid, palmitic acid, stearic acid, arachidic acid, behenic acid, oleic acid, linoleic acid, and linolenic acid. Mono esters of phospholipids are known in the art as the "lyso" forms of the phospholipid.

Further examples of phospholipids are phosphatidic acids, i.e., the diesters of glycerol-phosphoric acid with fatty acids, sphingomyelins, i.e., those phosphatidylcholine analogs where the residue of glycerol diester with fatty acids is replaced by a ceramide chain, cardiolipins, i.e. the esters of 1,3-diphosphatidylglycerol with a fatty acid, gangliosides, cerebrosides, etc.

As used herein, the term phospholipids includes either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins. Examples of semisynthetic phospholipids are the partially or fully hydrogenated derivatives of the naturally occurring lecithins.

Examples of synthetic phospholipids are e.g., dilauryloyl-phosphatidylcholine ("DLPC"), dimyristoylphosphatidylcholine ("DMPC"), dipalmitoyl-phosphatidylcholine ("DPPC"), diarachidoylphosphatidylcholine ("DAPC"), distearoyl-phosphatidylcholine ("DSPC"), 1-myristoyl-2-palmitoylphosphatidylcholine ("MPPC"), 1-palmitoyl-2-myristoylphosphatidylcholine ("PMPC"), 1-palmitoyl-2-stearoylphosphatidylcholine ("PSPC"), 1-stearoyl-2-palmitoyl-phosphatidylcholine ("SPPC"), dioleoylphosphatidylycholine ("DOPC"), 1,2 Distearoyl-sn-glycero-3-Ethylphosphocholine (Ethyl-DSPC), dilauryloyl-phosphatidylglycerol ("DLPG") and its alkali metal salts, diarachidoylphosphatidylglycerol ("DAPG") and its alkali metal salts, dimyristoylphosphatidylglycerol ("DMPG") and its alkali metal salts, dipalmitoyl-phosphatidylglycerol ("DPPG") and its alkali metal salts, distearolyphosphatidylglycerol ("DSPG") and its alkali metal salts, dioleoylphosphatidylglycerol ("DOPG") and its alkali metal salts, dimyristoyl phosphatidic acid ("DMPA") and its alkali metal salts, dipalmitoyl phosphatidic acid ("DPPA") and its alkali metal salts, distearoyl phosphatidic acid ("DSPA"), diarachidoyl phosphatidic acid ("DAPA") and its alkali metal salts, dimyristoyl phosphatidyl-ethanolamin-e ("DMPE"), dipalmitoyl phosphatidylethanolamine ("DPPE"), distearoyl phosphatidyl-ethanolamine ("DSPE"), dimyristoyl phosphatidylserine ("DMPS"), diarachidoyl phosphatidylserine ("DAPS"), dipalmitoyl phosphatidylserine ("DPPS"), distearoylphosphatidylserine ("DSPS"), dioleoylphosphatidylserine ("DOPS"), dipalmitoyl sphingomyelin ("DPSP"), and distearoyl sphingomyelin ("DSSP").

Suitable phospholipids further include phospholipids modified by linking a hydrophilic polymer thereto. Examples of modified phospholipids are phosphatidylethanolamines (PE) modified with polyethyleneglycol (PEG), in brief "PE-PEGs", i.e. phosphatidylethanolamines where the hydrophilic ethanolamine moiety is linked to a PEG molecule of variable molecular weight (e.g. from 300 to 5000 daltons), such as DPPE-PEG, DSPE-PEG, DMPE-PEG or DAPE-PEG (where DAPE is 1,2-diarachidoyl-sn-glycero-3-phosphoethanolamine). The compositions also may contain other amphiphilic compounds including, for instance, fatty acids, such as palmitic acid, stearic acid, arachidonic acid or oleic acid; sterols, such as cholesterol, or esters of sterols with fatty acids or with sugar acids; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate; tertiary or quaternary alkyl-ammonium salts, such as 1,2-distearoyl-3-trimethylammonium-propane (DSTAP), 1,2-dipalmitoyl-3-trimethylammonium-propane (DPTAP), and mixtures or combinations thereof.

Preferably, the formulation comprises at least one component bearing an overall net charge, such as, for instance, phosphatidic acid, PE-PEG, palmitic acid, stearic acid, Ethyl-DSPC or DSTAP, preferably in a molar amount of less than about 50%. Particularly preferred formulations may include mixtures of two or more of the following components: DSPC, DPPG, DPPA, DSPE-PEG1000, DSPE-PEG2000, palmitic acid and stearic acid. Some preferred phospholipids and formulations are set forth in the examples Any of the gases disclosed herein or known to the skilled artisan may be employed; however, inert gases, such as $SF_6$ or perfluorocarbons like $CF_4$, $C_3F_8$ and $C_4F_{10}$, are preferred, optionally in admixture with other gases such as air, nitrogen, oxygen or carbon dioxide The preferred microbubble suspensions of the present invention may be prepared from phospholipids using known processes such as a freeze-drying or spray-drying solutions of the crude phospholipids in a suitable solvent or using the processes set forth in EP 554213; WO 04/069284; U.S. Pat. No. 5,413,774; U.S. Pat. No. 5,578,292; EP 744962; EP 682530; U.S. Pat. No. 5,556,610; U.S. Pat. No. 5,846,518; U.S. Pat. No. 6,183,725; EP 474833; U.S. Pat. No. 5,271,928; U.S. Pat. No. 5,380,519; U.S. Pat. No. 5,531,980; U.S. Pat. No. 5,567,414; U.S. Pat. No. 5,658,551; U.S. Pat. No. 5,643,553; U.S. Pat. No. 5,911,972; U.S. Pat. No. 6,110,443; U.S. Pat. No. 6,136,293; EP 619743; U.S. Pat. No. 5,445,813; U.S. Pat. No. 5,597,549; U.S. Pat. No. 5,686,060; U.S. Pat. No. 6,187,288; and U.S. Pat. No. 5,908,610, which are incorporated by reference herein in their entirety. Preferably, as disclosed in International patent application WO 04/069284, a microemulsion can be prepared which contains the phospholipids (e.g DSPC and/or DSPA) in admixture with a lyoprotecting agent (such as, for instance, carbohydrates, sugar alcohols, polyglycols and mixtures thereof, as indicated in detail hereinafter) and optionally other amphiphilic materials (such as stearic acid), dispersed in an emulsion of water and of a water immiscible organic solvent. Preferred organic solvents are those having solubility in water of 1.0 g/l or lower, preferably lower about 0.01 g/l, and include, for instance, pentane, hexane, heptane, octane, nonane, decane, 1-pentene, 2-pentene, 1-octene, cyclopentane, cyclohexane, cyclooctane, 1-methyl-cyclohexane, benzene, toluene, ethylbenzene, 1,2-dimethylbenzene, 1,3-dimethylbenzene, di-butyl ether and di-isopropylketone, chloroform, carbon tetrachloride, 2-chloro-1-(difluoromethoxy)-1,1,2-trifluoroethane (enflurane), 2-chloro-2-(difluoromethoxy)-1,1,1-trifluoroethane (isoflurane), tetrachloro-1,1-difluoroethane, perfluoropentane, perfluorohexane, perfluoroheptane, perfluorononane, perfluorobenzene, perfluorodecalin, methylperfluorobutylether, methylperfluoroisobutylether, ethylperfluorobutylether, ethylperfluoroisobutylether and mixtures thereof. The peptide-phospholipid conjugate of the invention can be admixed together with the phospholipid forming the microvesicle's envelope, in the microemulsion. Preferably, an aqueous suspension of the peptide-phospholipid conjugate and of a PE-PEG (e.g. DSPE-PEG2000) is first prepared, which is then admixed together with an aqueous-organic emulsion comprising the phospholipid and the lyoprotecting agent. Preferably said mixing is effected under heating, e.g. form about 40° C. to 80° C.

Prior to formation of the suspension of microbubbles by dispersion in an aqueous carrier, the freeze dried or spray dried phospholipid powders are contacted with air or another gas. When contacted with the aqueous carrier the powdered phospholipids whose structure has been disrupted will form lamellarized or laminarized segments that will stabilize the microbubbles of the gas dispersed therein. This method permits production of suspensions of microbubbles that are stable even when stored for prolonged periods and are obtained by simple dissolution of the dried laminarized phospholipids (which have been stored under a desired gas) without shaking or any violent agitation.

Alternatively, microbubbles can be prepared by suspending a gas into an aqueous solution at high agitation speed, as disclosed e.g. in WO 97/29783. A further process for preparing microbubbles is disclosed in WO 2004/069284, herein incorporated by reference, which comprises preparing an emulsion of an organic solvent in an aqueous medium in the presence of a phospholipid and subsequently lyophilizing said emulsion, after optional washing and/or filtration steps. Some preferred preparation methods are disclosed in the examples.

The formulation for the preparation of the gas-filled microbubbles may advantageously further comprise a lyophilization additive, such as an agent with cryoprotective and/or lyoprotective effect and/or a bulking agent, for example an amino-acid such as glycine; a carbohydrate, e.g. a sugar such as sucrose, mannitol, maltose, trehalose, glucose, lactose or a cyclodextrin, or a polysaccharide such as dextran; or a polyglycol such as polyethylene glycol (e.g. PEG-4000).

Any of these ultrasound compositions should also be, as far as possible, isotonic with blood. Hence, before injection, small amounts of isotonic agents may be added to any of above ultrasound contrast agent suspensions. The isotonic agents are physiological solutions commonly used in medicine and they comprise aqueous saline solution (0.9% NaCl), 2.6% glycerol solution, 5% dextrose solution, etc. Additionally, the ultrasound compositions may include standard pharmaceutically acceptable additives, including, for example, emulsifying agents, viscosity modifiers, cryoprotectants, lyoprotectants, bulking agents etc.

Any biocompatible gas may be used in the ultrasound contrast agents of the invention. The term "gas" as used herein includes any substances (including mixtures) substantially in gaseous form at the normal human body temperature. The gas may thus include, for example, air, nitrogen, oxygen, $CO_2$, argon, xenon or krypton, fluorinated gases (including for example, perfluorocarbons, $SF_6$, $SeF_6$) a low molecular weight hydrocarbon (e.g., containing from 1 to 7 carbon atoms), for example, an alkane such as methane, ethane, a propane, a butane or a pentane, a cycloalkane such as cyclopropane, cyclobutane or cyclopentene, an alkene such as ethylene, propene, propadiene or a butene, or an alkyne such as acetylene or propyne and/or mixtures thereof. However, fluorinated gases are preferred. Fluorinated gases include materials that contain at least one fluorine atom such as $SF_6$, freons (organic compounds containing one or more carbon atoms and fluorine, i.e., $CF_4$, $C_2F_6$, $C_3F_8$, $C_1F_{10}$, $C_4F_{10}$, $CBrF_3$, $CCl_2F_2$, $C_2ClF_5$, and $CBrClF_2$) and perfluorocarbons. The term perfluorocarbon refers to compounds containing only carbon and fluorine atoms and includes, in particular, saturated, unsaturated, and cyclic perfluorocarbons. The saturated perfluorocarbons, which are usually preferred, have the formula $C_nF_n+2$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8C_4F_8$, $C_4F_{10}$, $C_5F_{12}$, $C_6F_2$, $C_7F_{14}$, $C_8F_{18}$, and $C_9F_{20}$. Most preferably the gas or gas mixture comprises $SF_6$ or a perfluorocarbon selected from the group consisting of $C_3F_8$ $C_4F_8$, $C_4F_{10}$, $C_5F_2$, $C_6F_{12}$, $C_7F_{14}$, $C_8F_{18}$, with $C_4F_{10}$ being particularly preferred. See also WO 97/29783, WO 98/53857, WO 98/18498, WO 98/18495, WO 98/18496, WO 98/18497, WO 98/18501, WO 98/05364, WO 98/17324. In a preferred embodiment the gas comprises $C_4F_{10}$ or $SF_6$, optionally in admixture with air, nitrogen, oxygen or carbon dioxide.

In certain circumstances it may be desirable to include a precursor to a gaseous substance (e.g., a material that is capable of being converted to a gas in vivo, often referred to as a "gas precursor"). Preferably the gas precursor and the gas it produces are physiologically acceptable. The gas precursor may be pH-activated, photo-activated, temperature activated, etc. For example, certain perfluorocarbons may be used as temperature activated gas precursors. These perfluorocarbons, such as perfluoropentane, have a liquid/gas phase transition temperature above room temperature (or the temperature at which the agents are produced and/or stored) but below body temperature; thus they undergo a phase shift and are converted to a gas within the human body.

As discussed above, the gas can comprise a mixture of gases. The following combinations are particularly preferred gas mixtures: a mixture of gases (A) and (B) in which, at least one of the gases (B), present in an amount of between 0.5-41% by vol., has a molecular weight greater than 80 daltons and is a fluorinated gas and (A) is selected from the group consisting of air, oxygen, nitrogen, carbon dioxide and mixtures thereof, the balance of the mixture being gas A.

Unless it contains a hyperpolarized gas, known to require special storage conditions, the lyophilized product may be stored and transported without need of temperature control of its environment and in particular it may be supplied to hospitals and physicians for on site formulation into a ready-to-use administrable suspension without requiring such users to have special storage facilities. Preferably in such a case it can be supplied in the form of a two-component kit, which can include two separate containers or a dual-chamber container. In the former case preferably the container is a conventional septum-sealed vial, wherein the vial containing the lyophilized residue of step b) is sealed with a septum through which the carrier liquid may be injected using an optionally prefilled syringe. In such a case the syringe used as the container of the second component is also used then for injecting the contrast agent. In the latter case, preferably the dual-chamber container is a dual-chamber syringe and once the lyophilizate has been reconstituted and then suitably mixed or gently shaken, the container can be used directly for injecting the contrast agent. In both cases means for directing or permitting application of sufficient bubble forming energy into the contents of the container are provided. However, as noted above, in the stabilised contrast agents according to the invention the size of the gas microbubbles is substantially independent of the amount of agitation energy applied to the reconstituted dried product. Accordingly, no more than gentle hand shaking is generally required to give reproducible products with consistent microbubble size.

It can be appreciated by one of ordinary skilled in the art that other two-chamber reconstitution systems capable of combining the dried powder with the aqueous solution in a sterile manner are also within the scope of the present invention. In such systems, it is particularly advantageous if the aqueous phase can be interposed between the water-insoluble gas and the environment, to increase shelf life of the product. Where a material necessary for forming the contrast agent is not already present in the container (e.g. a targeting ligand to be linked to the phospholipid during reconstitution), it can be packaged with the other components of the kit, preferably in a form or container adapted to facilitate ready combination with the other components of the kit.

No specific containers, vial or connection systems are required; the present invention may use conventional containers, vials and adapters. The only requirement is a good seal between the stopper and the container. The quality of the seal, therefore, becomes a matter of primary concern; any degradation of seal integrity could allow undesirable substances to enter the vial. In addition to assuring sterility, vacuum retention is essential for products stoppered at ambient or reduced pressures to assure safe and proper reconstitution. The stopper may be a compound or multicomponent formulation based on an elastomer, such as poly(isobutylene) or butyl rubber.

In ultrasound applications the contrast agents formed by phospholipid stabilized microbubbles can be administered, for example, in doses such that the amount of phospholipid injected is in the range 0.1 to 200 μg/kg body weight, preferably from about 0.1 to 30 μg/kg.

Ultrasound imaging techniques that can be used in accordance with the present invention include known techniques, such as color Doppler, power Doppler, Doppler amplitude, stimulated acoustic imaging, and two- or three-dimensional imaging techniques. Imaging may be done in harmonic (resonant frequency) or fundamental modes, with the second harmonic preferred.

The ultrasound contrast agents of the present invention may further be used in a variety of therapeutic imaging methods. The term therapeutic imaging includes within its meaning any method for the treatment of a disease in a patient which comprises the use of a contrast imaging agent (e.g. for the delivery of a therapeutic agent to a selected receptor or tissue), and which is capable of exerting or is responsible to exert a biological effect in vitro and/or in vivo. Therapeutic imaging may advantageously be associated with the controlled localized destruction of the gas-filled microvesicles, e.g. by means of an ultrasound burst at high acoustic pressure (typically higher than the one generally employed in non-destructive diagnostic imaging methods). This controlled destruction may be used, for instance, for the treatment of blood clots (a technique also known as sonothrombolysis), optionally in combination with the localized release of a suitable therapeutic agent. Alternatively, said therapeutic imaging may include the delivery of a therapeutic agent into cells, as a result of a transient membrane permeabilization at the cellular level induced by the localized burst of the microvesicles. This technique can be used, for instance, for an effective delivery of genetic material into the cells; optionally, a drug can be locally delivered in combination with genetic material, thus allowing a combined pharmaceutical/genetic therapy of the patient (e.g. in case of tumor treatment).

The term "therapeutic agent" includes within its meaning any substance, composition or particle which may be used in any therapeutic application, such as in methods for the treatment of a disease in a patient, as well as any substance which is capable of exerting or responsible to exert a biological effect in vitro and/or in vivo. Therapeutic agents thus include any compound or material capable of being used in the treatment (including diagnosis, prevention, alleviation, pain relief or cure) of any pathological status in a patient (including malady, affliction, disease lesion or injury). Examples of therapeutic agents are drugs, pharmaceuticals, bioactive agents, cytotoxic agents, chemotherapy agents, radiotherapeutic agents, proteins, natural or synthetic peptides, including oligopeptides and polypeptides, vitamins, steroids and genetic material, including nucleosides, nucleotides, oligonucleotides, polynucleotides and plasmids.

Materials and Analytical Methods

Solvents for reactions, chromatographic purification and HPLC analyses were E. Merck Omni grade solvents from VWR Corporation (West Chester, Pa.). N-Methylpyrrolidinone (NMP) and N,N-dimethylformamide (DMF) were obtained from Pharmco Products Inc. (Brookfield, Conn.), and were peptide synthesis grade or low water/amine-free Biotech grade quality. Piperidine (sequencing grade, redistilled 99+%) and trifluoroacetic acid (TFA) (spectrophotometric grade or sequencing grade) were obtained from Sigma-Aldrich Corporation (Milwaukee, Wis.) or from the Fluka Chemical Division of Sigma-Alrich Corporation. N,N'-Diisopropylcarbodiimide (DIC), phenol (99%), N,N-diisopropylethylamine (DIEA) and triisopropylsilane (TIS) were purchased from Sigma-Aldrich Corporation. Fmoc-protected amino acids, pseudoproline dipeptides, Fmoc-Asp(O-tBu)-Ser($\psi^{Me,Me}$pro)-OH and Fmoc-Gly-Thr($\psi^{Me,Me}$pro)-OH and N-hydroxybenzotriazole (HOBt) were obtained from Novabiochem (San Diego, Calif.). Fmoc-8-amino-3,6-dioxaoctanoic acid (Adoa) was obtained from NeoMPS Corp (San Diego, Calif.) or Suven Life Sciences (Hyderabad, India). Disuccinimidyl glutarate (DSG) and 1,2-distearoyl-sn-glycero-3-phospho-ethanolamine-N-[amino(polyethyleneglycol) 2000] ammonium salt, [DSPE-PEG2000-NH$_2$] were obtained from Pierce Chemical Co. (Rockford, Ill.) and Avanti® Polar Lipids (Alabaster, Ala.), respectively. Fmoc-Gly-Gly-Gly-OH and Fmoc-Gly-Gly-OH were prepared in-house from the corresponding triglycine or diglycine by the reaction with Fmoc-OSu. An AG MP-50 ion-exchange resin was obtained from Bio-Rad (Hercules, Calif.).

Analytical HPLC data were generally obtained using a Shimadzu LC-10AT VP dual pump gradient system employing a Waters XTerra MS-C18 4.6×50 mm column, (particle size: 5μ; 120 Å pore size) and gradient or isocratic elution systems using water (0.1% TFA) as eluent A and CH$_3$CN (0.1% TFA) or CH$_3$CN—CH$_3$OH (1:1, v/v) (0.1% TFA) as eluent B. Detection of compounds was accomplished using UV at 220 and 254 nm. The purity of the phospholipid-PEG-peptide derivatives was determined on a YMC C-4 (5 μM, 300 Å, 4.6×250 mm) column or on a Zorbax 300 SB-C3 (3.5 μM; 300 Å, 3×150 mm) column using a SEDEX 55 Light Scattering Detector (LSD) and with a UV detector.

Preparative HPLC was conducted on a Shimadzu LC-8A dual pump gradient system equipped with a SPD-10AV UV detector fitted with a preparative flow cell. Generally the solution containing the crude peptide was loaded onto a reversed phase C18, C4 or C3 column, depending on the compound characteristics, using a third pump attached to the preparative Shimadzu LC-8A dual pump gradient system. After the solution of the crude product mixture was applied to the preparative HPLC column the reaction solvents and solvents employed as diluents, such as DMF or DMSO, were eluted from the column at low organic phase composition. Then the desired product was eluted using a gradient elution of eluent B into eluent A. Product-containing fractions were combined based on their purity as determined by analytical HPLC and mass spectral analysis. The combined fractions were freeze-dried to provide the desired product.

Amino acid composition analyses were performed at the Keck Biotechnology Resource Laboratory at Yale University, New Haven, Conn. Mass spectral data were obtained from MScan Inc. (606 Brandywine Parkway, West Chester Pa. 19380) or obtained in-house on an Agilent LC-MSD 1100 Mass Spectrometer. For the purposes of fraction selection and characterization of the products mass spectral values were usually obtained using API-ES in negative ion mode. Generally the molecular weight of the target peptides was ~3000; the mass spectra usually exhibited doubly or triply negatively charged ion mass values rather than [M-H]$^-$. These were generally employed for selection of fractions for collection and combination to obtain the pure peptide during HPLC purification. In some cases fractions exhibited dominant peaks attributable to [M-2H]/2+57 or [M-2H]/2+114 in the mass spectrum. These peaks are due to the formation of adducts of one or two molecules of trifluoroacetic acid per molecule of the peptide. After careful collection of fractions by comparing MS results and HPLC purities and freeze-drying process, a small amount of the isolated fluffy solid was dissolved in water (0.5 mg/mL) and treated with a drop of aqueous N-methyl-D-glucamine (~0.5 M). This solution was analyzed by HPLC and MS for final purity results of the purified peptide. Peptide solutions in the presence of N-methyl-D-glucamine did not exhibit [M-2H]/2+57 or [M-2H]/2+114 mass value peaks in the mass spectrum, instead the expected [M-2H]/2 or [M-3H]/3 peaks were observed.

The following non-limiting Examples provide additional detail on efficient processes used for obtaining large quantities of highly purified forms of the monomeric and dimeric peptide phospholipid conjugates. These non-limiting Examples also describe the preparation of representative targeted microbubbles which include these monomeric and dimeric peptide phospholipid conjugates. These Examples also describe the use of such targeted microbubbles in static binding tests on KDR-transfected cells and dynamic binding tests on rh VEGF-R2/Fc chimeric protein. The Examples further describe the evaluation of ultrasound contrast agents containing KDR binding lipopeptides in a rabbit VX2 tumor model.

EXAMPLES

Examples 1-2 below refer to the monomeric peptide phospholipid conjugate shown in FIG. 2. A process for synthesizing this compound is shown in FIG. 1. Although these Examples refer more specifically to the process for synthesizing the compound shown in FIG. 2, a similar process may used to prepare the monomeric peptide phospholipid conjugate shown in FIG. 10 and the linear peptide monomer (32) shown in FIG. 9 as well as other monomer peptide-phospholipid conjugates. Additionally, co-pending U.S. application Ser. No. 10/661,156, filed Sep. 11, 2003, sets forth methods for the preparation of the peptide monomers and is incorporated by reference herein in its entirety.

Example 1

Solid Phase Synthesis (SPPS) and Purification of Linear Peptide Monomer (2) Ac-RAQDWYY-DEILSMADQLRHAFLSGGGGGK-NH$_2$, (SEQ ID NO. 2) Ac-Arg-Ala-Gln-Asp-Trp-Tyr-Tyr-Asp-Glu-Ile-Leu-Ser-Met-Ala-Asp-Gln-Leu-Arg-His-Ala-Phe-Leu-Ser-Gly-Gly-Gly-Gly-Gly-Lys-NH$_2$; N-acetyl-L-alanyl-L-glutaminyl-L-aspartyl-L-tryptophyl-L-tyrosyl-L-tyrosyl-L-aspartyl-L-glutamyl-L-isoleucyl-L-leucyl-L-seryl-L-methionyl-L-alanyl-L-aspartyl-L-glutamyl-L-leucyl-L-arginyl-L-histidyl-L-alanyl-L- phenylalanyl-L-leucyl-L-seryl-glycyl-glycyl-glycyl-glycyl-glycyl-L-lysinamide The linear peptide monomer (2) was synthesized by an established automated protocol on a SONATA®/Pilot Peptide Synthesizer using Fmoc-Pal-Peg-PS resin (0.2 mmol/g), Fmoc-protected amino acids and DIC-mediated HOBt ester activation in DMF. The peptide sequence was synthesized in stepwise fashion by SPPS methods on the Fmoc-Pal-Peg-PS resin, typically on a 10 mmol scale. The amino acid couplings were carried out with a 4-fold excess each of amino acid and the DIC-HOBt reagent pair in DMF.

In a typical coupling of an amino acid, 5 mL of dry DMF per gram of resin was used. The total volume of DMF, calculated on the basis of resin used, was allocated among amino acid, HOBt and DIC for solution preparation. For example, for the synthesis involving 50 g (10 mmol scale) of resin, the calculated volume of 250 mL of DMF was distributed among amino acid (150 mL), HOBt (50 mL) and DIC (50 mL). The amino acid vessel on the Sonata Pilot Peptide Synthesizer was charged with the solid dry amino acid (4-fold excess with respect to the resin). At inception of the coupling step, the software of the instrument was employed to deliver successively the chosen volume of DMF (for dilution of the amino acid) and HOBt (4 eq.) in DMF and DIC (4 eq.) in DMF and mixing by nitrogen bubbling was initiated and conducted for 4 min. This served to pre-activate the amino acid and to insure complete dissolution of all components of the mixture. After activation, the software mediated the transfer of the solution of the activated Fmoc-amino acid to the reaction vessel containing the resin. After transfer was complete the vessel was agitated for 3 h with recurrent nitrogen bubbling. After the 3 h coupling time, the resin was washed thoroughly with DMF (5 mL/g, 6×) and the cleavage of the Fmoc-group was performed with 25% piperidine in DMF (5 mL/g) containing HOBt (0.1M) (2×10 min). The resin was thoroughly washed with DMF (5 mL/g, 6×) to assure complete removal of piperidine from the resin in preparation for the ensuing amino acid coupling. In the case of Fmoc-Gly-Gly-Gly-OH and Fmoc-Gly-Gly-OH, the pre-activation in the amino acid bottle was not conducted in order to minimize the formation of diketopiperazine during the activation time as discussed in the text. Therefore, in these two cases, the solutions of amino acid, HOBt and DIC were added to the reaction vessel sequentially and the coupling process was conducted with 'in situ' activation.

After chain elongation was completed, the Fmoc group of the N-terminal amino acid was removed in the standard manner followed by the standard wash with DMF (vide supra). The N-terminal amino acid was then capped by treatment with freshly prepared acetylation mixture (0.5M acetic anhydride, 0.125M DIEA and 0.015M HOBt in DMF/6 mL/g of resin), 2×20 min. After completion of the peptide synthesis, the resin was treated with the cleavage cocktail, 'Reagent B' (TFA:water:phenol:triisopropylsilane, 88:5:5:2, v/v/w/v) (10 mL/g of resin) for 4 h. The volatiles were removed and the paste thus obtained was triturated with ether to provide a solid which was washed with ether (3×) with intervening centrifugation (to compact the suspended solids in order to allow decantation of the supernatant) and then dried under vacuum to provide the required peptide as an off-white solid. A 10 mmol scale synthesis of the linear peptide monomer (2) gave 33.82 g (103% of theory) of the crude peptide. The greater than theoretical yield was most likely due to moisture and residual solvents.

Purification of the Linear Peptide Monomer (2) Ac-RAQDWYYDEILSMADQLRHAFLSGGGGGK-NH$_2$ (SEQ ID NO. 2); Ac-Arg-Ala-Gln-Asp-Trp-Tyr-Tyr-Asp-Glu-Ile-Leu-Ser-Met-Ala-Asp-Gln-Leu-Arg-His-Ala-Phe-Leu-Ser-Gly-Gly-Gly-Gly-Gly-Lys-NH$_2$; N-acetyl-L-alanyl-L-glutaminyl-L-aspartyl-L-tryptophyl-L-tyrosyl-L-tyrosyl-L-aspartyl-L-glutamyl-L-isoleucyl-L-leucyl-L-seryl-L-methionyl-L-alanyl-L-aspartyl-L-glutamyl-L-leucyl-L-arginyl-L-histidyl-L-alanyl-L- phenylalanyl-L-leucyl-L-seryl-glycyl-glycyl-glycyl-glycyl-glycyl-L-lysinamide A ~0.5 g portion of the crude linear peptide monomer (2) was dissolved in a minimum amount of CH$_3$CN (~20 mL). The volume of the solution was adjusted to ~100 mL with water and employing a third pump the solution was loaded onto a reversed phase C18 preparative column (Waters, XTerra® Prep MS C18, 10μ, 300 Å, 50×250 mm, flow rate 100 mL/min) which had been pre-equilibrated with 10% CH$_3$CN in water (0.1% TFA). The column was not eluted with the equilibrating eluent during application of the sample solution. After the sample solution was applied to the column, the composition of the eluent was ramped to 20% CH$_3$CN-water (0.1% TFA) over 1 min, and a linear gradient at a rate of 0.6%/min of CH$_3$CN (0.1% TFA) into water (0.1% TFA) was initiated and maintained for 50 min. Fractions (15 mL) were manually collected using UV at 220 nm as an indicator of product elution. The collected fractions were analyzed on a Waters XTerra analytical reversed phase C-18 column (5μ particle, 120 Å pore) and product-containing fractions of >95% purity were pooled and freeze-dried to afford the corresponding pure linear peptide monomer (2). Typically the purification of 0.5 g of crude (2) afforded 0.12 g (24% yield) of the desired product (>95% purity).

Example 2

Preparation of Monomeric Peptide Phospholipid Conjugate (1) Ac-RAQDWYYDEILSMADQL-RHAFLSGGGGGK(DSPE-PEG2000-NH-Glut)-NH$_2$ (SEQ ID NO. 1); Ac-Arg-Ala-Gln-Asp-Trp-Tyr-Tyr-Asp-Glu-Ile-Leu-Ser-Met-Ala-Asp-Gln-Leu-Arg-His-Ala-Phe-Leu-Ser-Gly-Gly-Gly-Gly-Gly-Lys-(DSPE-PEG2000-NH-Glut)-NH$_2$; N-acetyl-L-arginyl-L-alanyl-L-glutaminyl-L-aspartyl-L-tryptophyl-L-tryptophyl-L-aspartyl-L-isoleucyl-L-glutamyl-L-leucyl-1-serinyl-L-methionyl-L-alanyl-L-aspartyl-L-glutaminyl-L-leucyl-L-arginyl-L-histidyl-L-alanyl-L-phenylalanyl-L-leucyl-L-serinyl-glycyl-glycyl-glycl-glycyl-glycyl-L-lysinamide The monomeric peptide phospholipid conjugate (1), Ac-RAQDWYYDEILSMADQLRHAFLSGGGGGK (DSPE-PEG2000-NH-Glut)-NH$_2$(SEQ ID NO. 1), was prepared by conjugation of (3), the glutaric acid monoamide mono-NHS ester of peptide monomer (2), with DSPE-PEG2000-NH$_2$ phospholipid ammonium salt (4).

A round-bottomed flask equipped with magnetic stir bar and septum cap was charged sequentially with anhydrous dimethylformamide (7.5 mL), disuccinimidyl glutarate (DSG, 0.25 g, 0.75 mmol) and diisopropylethylamine (0.10 g, 0.78 mmol) with stirring. Solid linear peptide monomer (2) (0.5 g, 0.152 mmol) was added portionwise to the above solution over a period of 2 min; then the solution was stirred for 30 min at ambient temperature. The reaction mixture was diluted to ~50 mL with anhydrous ethyl acetate; this resulted in precipitation of the intermediate mono-NHS ester (3), the glutaric acid monoamide mono-NHS ester of peptide monomer (2). The solution was centrifuged to bring down mono-NHS ester (3)) as a colorless solid. The supernatant containing excess DSG was decanted from the compacted solid mono-NHS ester (3) which was again dispersed in ethyl acetate, centrifuged and washed twice more to remove the remaining traces of DSG. The solid intermediate mono-NHS ester (3) thus obtained was dissolved in anhydrous DMF (10.0 mL); diisopropylethylamine (0.10 g, 0.78 mmol) was added; and the mixture was stirred.

Meanwhile, DSPE-PEG2000-NH$_2$ phospholipid ammonium salt (4) (0.38 g, 0.14 mmol, 0.9 eq.) was suspended in dry dichloromethane (2 mL) in a separate flask and trifluoroacetic acid (2 drops) was added to protonate the phosphodiester oxygen facilitating solubilization of phospholipid ammonium salt in dichloromethane. The clear solution was then evaporated on a rotary evaporator to remove the volatiles and dried further under vacuum.

The solid phospholipid ammonium salt (4) was dissolved in DMF (5 mL) and transferred to the stirred solution of mono-NHS ester (3) and the resulting mixture was stirred for 24 h at ambient temperature. The reaction mixture was diluted to 100 mL with a 1:1 mixture of $CH_3OH$ and $CH_3CN$-water (1:1, v/v) and the insolubles were filtered. Half of the filtered solution was loaded onto a reversed phase C2 preparative column (Kromasil® Prep C2, 10μ, 300 Å, 50×250 mm) which had been pre-equilibrated with 3:1 (v/v) mixture of water (0.1% TFA) and $CH_3OH$—$CH_3CN$ (1:1, v/v, 0.1% TFA) at a flow rate of 100 mL/min. Note that the column was not eluted with the equilibrating eluent during loading of the sample. After the sample solution was loaded the column was washed with the equilibration eluent until the plug of DMF was eluted. The composition of the eluent was ramped to 70% $CH_3OH$—$CH_3CN$ (1:1, 0.1% TFA) over 9 min and a linear gradient of 0.75%/min of $CH_3OH$—$CH_3CN$ (1:1, 0.1% TFA) into water (0.1% TFA) was initiated and run for 40 min. Fractions (15 mL) were collected using UV (220 nm) as an indicator of product elution. Fractions were checked for purity on an analytical HPLC system (column: YMC C-4, 5μ, 300 Å, 4.6×250 mm) using UV at 220 nm and an evaporative light scattering detector (ELSD). The latter detector (ELSD) was employed to detect DSPE-PEG2000-$NH_2$ phospholipid ammonium salt (4) which has very little UV absorbance at 220 nm. Product-containing fractions of >98% purity, and devoid of DSPE-PEG2000-$NH_2$ phospholipid ammonium salt (4) were combined and concentrated on a rotary evaporator to reduce the content of $CH_3OH$. The concentrated solution was then diluted with 10% $CH_3CN$ in water until a faint flocculent precipitate formed. The resulting solution was freeze-dried to provide monomeric peptide phospholipid conjugate (1) as a colorless solid. The second portion of crude monomeric peptide phospholipid conjugate (1) was purified as described above. The combined yield of the target monomeric peptide phospholipid conjugate (1) was 0.40 g (47% yield).

Examples 3-5 below refer to the dimeric peptide phospholipid conjugate shown in FIG. 5. Representative methods of synthesizing the dimeric conjugate are shown in FIGS. 3, 4, 6, 7 and 8.

Example 3

Solid Phase Synthesis (SPPS), Cyclization and Purification of Monomer Peptides (12) Ac-AGPTWC*EDDWYYC*WLFGTGGGK[K(ivDde)]-$NH_2$ and (13) Ac-VC*WEDSWGGEVC*FRYDPGGGK(Adoa-Adoa)-$NH_2$ The linear peptides were synthesized by an established automated protocol on a SONATA®/Pilot Peptide Synthesizer using Fmoc-Pal-Peg-PS resin (0.2 mmol/g), Fmoc-protected amino acids and DCI-mediated HOBt ester activation in DMF. The peptide sequence on the Fmoc-Pal-Peg-PS resin was synthesized in stepwise fashion by SPPS methods typically on a 10 mmol scale. The amino acid coupling was carried out with a 4-fold excess each of amino acid and DIC-HOBt reagent in DMF.

In a typical coupling of an amino acid in the sequence, 5 mL of dry DMF per gram of resin was used. The total volume of DMF, calculated on the basis of resin used, was allocated among amino acid, HOBt and DIC for solution preparation. For example, for the synthesis involving 50 g of resin, the calculated volume of 250 mL of DMF was distributed among amino acid (150 mL), HOBt (50 mL) and DIC (50 mL). The amino acid vessel on the Sonata® Pilot Peptide Synthesizer was charged with the solid dry amino acid (4-fold excess with respect to the resin). At inception of the coupling step, the chosen volume of DMF and HOBt (4 eq.) in DMF and DIC (4 eq.) in DMF were delivered successively and after each delivery mixing by nitrogen bubbling was conducted. After the last reagent was delivered mixing by nitrogen bubbling was initiated and conducted for 4 min. This served to preactivate the amino acid and to insure complete dissolution of all components of the mixture.

After activation, the solution of the activated Fmoc-amino acid was transferred to the reaction vessel containing the resin. After transfer was complete the vessel was agitated for 3 h with recurrent nitrogen bubbling. After the 3 h coupling time, the resin was washed thoroughly with DMF (5 mL/g, 6×) and the cleavage of the Fmoc-group was performed with 25% piperidine in DMF (5 mL/g) containing HOBt (0.1M) (2×10 min). The resin was thoroughly washed with DMF (5 mL/g, 6×) to assure complete removal of piperidine from the resin in preparation for the ensuing amino acid coupling. In the case of Fmoc-Gly-Gly-Gly-OH and Fmoc-Gly-Gly-OH, the pre-activation in the amino acid bottle was not conducted in order to minimize the formation of diketopiperazine during the activation time as discussed in the text. Therefore, in these two cases, the solution of the amino acid, HOBt and DIC were added to the reaction vessel sequentially and the coupling process was conducted with 'in situ' activation. After chain elongation was completed, the fmoc group of the N-terminal amino acid was removed in the standard manner followed by the standard wash with DMF (vide supra). The N-terminal amino acid was then capped by treatment with freshly prepared acetylation mixture (0.5M acetic anhydride, 0.125M DIEA and 0.015M HOBt in DMF—6 mL/g of resin), 2×20 min.

Functionalization of the ε-amino group of C-terminal Lysine moieties of the monomer peptides (with Fmoc-Adoa or with Fmoc-Lys(ivDde) as required) was accomplished by first removing the ivDde group of the ε-amino group with freshly prepared 10% hydrazine in DMF (5 mL/g of resin—2×10 min). For appending of Fmoc-Adoa or Fmoc-Lys (ivDde) the coupling time was increased to 10 h. After completion of the peptide synthesis, the resin was treated with the cleavage cocktail, 'Reagent B' (TFA:water:phenol:triisopropylsilane, 88:5:5:2, v/v/w/v) (10 mL/g of resin) for 4 h. After evaporation of the volatiles under vacuum, the paste was triturated with ether to provide a solid which was collected by filtration washed with diethyl ether and dried. A 10 mmol scale synthesis of (12), Ac-AGPTWC*EDDWYYC*WLFGTGGGK[K(ivDde)]-$NH_2$ gave 30 g (103% of theory) of the crude peptide. In the case of (13) Ac-VC*WEDSWGGEVC*FRYDPGGGK(Adoa-Adoa)-$NH_2$, a 10 mmol scale synthesis gave 28 g (107% of theory) of crude peptide. The greater than theoretical yields are most likely due to moisture and residual solvents.

Cyclization of the Linear Di-Cysteine Peptides to Cyclic Disulfide Peptides

Cyclic disulfide peptides were prepared from the corresponding linear di-cysteine peptides by DMSO-assisted oxidation using DMSO/water (95/5, v/v). The crude linear peptide was dissolved in the solvent mixture (5 mL/g) in a wide mouth beaker, and the pH of the solution was adjusted to 8.5 by the addition of solid N-methyl-D-glucamine in portions.

The resulting mixture was stirred for 36 h at ambient temperature. The solution was then diluted with acetonitrile (50 mL/g) and the mixture was stirred for 2 min. The solid cyclic disulfide peptide was collected by filtration, washed with diethyl ether and dried.

Purification of Monomer Peptides Peptide Monomer (11) Ac-AGPTWC*EDDWYYC*WLFGTGGGK[K (ivDde)]-NH$_2$; Ac-Ala-Gly-Pro-Thr-Trp-Cys-Glu-Asp-Asp-Trp-Tyr-Tyr-Cys-Trp-Leu-Phe-Gly-Thr-Gly-Gly-Gly-Lys[Lys(ivDde)]-NH$_2$ cyclic (6-13) disulfide A ~0.5 g portion of the crude cyclic disulfide peptide monomer (12) was dissolved in a minimum amount of DMSO (~3 mL). The volume of the solution was adjusted to ~100 mL with 20% CH$_3$CN-water and employing a third pump, the solution was loaded onto a reversed phase C18 preparative column (Waters, XTerra® Prep MS C18, 10μ, 300 Å, 50×250 mm, flow rate 100 mL/min), which had been pre-equilibrated with 10% CH$_3$CN in water (0.1% TFA). During application of the sample solution to the column the flow of the equilibrating eluent from the preparative HPLC system was stopped. After the sample solution was applied to the column, the flow of equilibrating eluent from the gradient HPLC system was reinitiated and the column was eluted with 10% CH$_3$CN-water (0.1% TFA) until the DMSO was eluted. Then the eluent composition was ramped to 35% CH$_3$CN-water (0.1% TFA) over 1 min after which a linear gradient at a rate of 0.5%/min CH$_3$CN (0.1% TFA) into water (0.1% TFA) was initiated and maintained for 50 min. Fractions (15 mL) were manually collected using UV at 220 nm as an indicator of product elution. The collected fractions were analyzed on a Waters XTerra analytical reversed phase C-18 column (5 μparticle, 120 Å pore) and product-containing fractions of >95% purity were pooled and freeze-dried to afford the corresponding cyclic disulfide peptide monomer (12). Typically the purification of 0.5 g of crude peptide monomer (12) afforded 0.1 g (20% yield) of the desired product (>95% purity).

Peptide Monomer (13) Ac-VC*WEDSWGGEVC*FRYDPGGGK(Adoa-Adoa)-NH$_2$; Ac-Val-Cys-Trp-Glu-Asp-Ser-Trp-Gly-Gly-Glu-Val-Cys-Phe-Arg-Tyr-Asp-Pro-Gly-Gly-Gly-Lys(Adoa-Adoa)-NH$_2$ cyclic (2-12) disulfide Following the procedure employed for the HPLC purification of peptide monomer (2), the crude cyclic disulfide peptide monomer (13) Ac-VC*WEDSWGGEVC*FRYDPGGGK(Adoa-Adoa)-NH$_2$ (0.5 g) dissolved in 20% CH$_3$CN-water mixture (100 mL) was loaded onto a reversed phase C18 preparative column (Waters, XTerra® Prep MS C18, 50×250 mm, 10 μparticle, 300 Å pore, flow rate 100 mL/min), which had been pre-equilibrated with 10% CH$_3$CN (0.1% TFA) in water (0.1% TFA). During application of the sample solution to the column the flow of the equilibrating eluent from the preparative HPLC system was stopped. After the sample solution was applied to the column, the flow of equilibrating eluent from the gradient HPLC system was reinitiated and the column was eluted with 10% CH$_3$CN-water (0.1% TFA) for 5 min. Then the eluent composition was ramped to 30% CH$_3$CN (0.1% TFA)-water (0.1% TFA) over 1 min and a linear gradient elution at a rate of 0.5%/min of CH$_3$CN (0.1% TFA) into water (0.1% TFA) was initiated and maintained for 50 min. Fractions (15 mL) were manually collected using UV at 220 nm as an indicator of product elution. The fractions were analyzed on a Waters XTerra analytical reversed phase C-18 column (4.6 mm i.d.×50 mm, 5μ particle, 120 Å pore) and product-containing fractions of >95% purity were pooled and freeze-dried to afford the corresponding cyclic disulfide peptide monomer (13). Typically the purification of 0.5 g of crude peptide monomer (3) afforded 0.12 g (24% yield) of the desired product (>95% purity).

Example 4

Preparation and Purification of Precursor Dimer Peptide (16) Ac-AGPTWCEDDWYYCWLFGTGGGK [Ac-VCWEDSWGGEVCFRYDPGGGK(-Adoa-Adoa-Glut-K)]-NH$_2$ cyclic (2-12) disulfide]-NH$_2$ cyclic (6-13) disulfide; Ac-Ala-Gly-Pro-Thr-Trp-Cys-Glu-Asp-Asp-Trp-Tyr-Tyr-Cys-Trp-Leu-Phe-Gly-Thr-Gly-Gly-Gly-Lys[Ac-Val-Cys-Trp-Glu-Asp-Ser-Trp-Gly-Gly-Glu-Val-Cys-Phe-Arg-Tyr-Asp-Pro-Gly-Gly-Gly-Lys(-Adoa-Adoa-Glut-Lys)]-NH$_2$ cyclic (2-12) disulfide]-NH$_2$ cyclic (6-13) disulfide As shown in FIG. 3, disuccinimidyl glutarate (DSG, 0.28 g, 0.86 mmol) was dissolved in stirred anhydrous dimethylformamide (2.0 mL) and diisopropylethylamine (0.11 g, 0.85 mmol) was added in one portion. Then solid peptide monomer (12) Ac-AGPTWC*EDDWYYC*WLFGTGGGK-[K (ivDde)]-NH$_2$ (0.50 g, 0.17 mmol) was added in portions to the stirred solution of DSG over a period of two min. After stirring for 30 min at room temperature, the solution was diluted with anhydrous ethyl acetate to ~50 mL, (this served to precipitate intermediate mono-NHS ester (14)). The entire mixture was centrifuged and the supernatant was decanted leaving intermediate mono-NHS ester (14) as a colorless solid. The solid was resuspended with ethyl acetate; the solution containing the suspended solid mono-NHS ester (14) was centrifuged to separate the solid and the supernatant was again decanted. This washing process was repeated twice to remove completely the excess DSG.

The solid mono-NHS ester (14) was dissolved in stirred anhydrous dimethylformamide (2.0 mL) and diisopropylethylamine (0.11 g, 0.85 mmol) was added. Then solid peptide monomer (13), Ac-VC*WEDSWGGEVC*FRYDPGGGK(Adoa-Adoa)-NH$_2$, (0.50 g, 0.19 mmol, 1.12 eq.) was added in portions to the stirred solution over a three min. period and the resulting mixture was stirred for 18 h. The reaction was monitored by mass spectrometry; after the complete consumption of the peptide monomer glutaric acid monoamide mono-NHS ester (14) was confirmed, neat hydrazine (0.1 mL) was added to remove the ivDde protecting group of the ivDde-bearing dimer (15) and the mixture was stirred for 20 min at room temperature.

The solution was then acidified by dropwise addition of TFA and the mixture was diluted to 100 mL with 10% CH$_3$CN (0.1% TFA) in water (0.1% TFA). The solution was filtered to remove particulates and half of the clarified solution was loaded onto a reversed phase C18 preparative column (Waters, XTerra® Prep MS C18, 10μ, 50×250 mm, flow rate 100 mL/min) pre-equilibrated with 10% CH$_3$CN in water (0.1% TFA). During application of the sample solution to the column the flow of the equilibrating eluent from the preparative HPLC system was stopped. After the sample solution was applied to the column, the flow of equilibrating eluent from the gradient HPLC system was reinitiated and the column was eluted with 10% CH$_3$CN-water (0.1% TFA) in order to flush DMF from the column. After elution of the DMF plug was completed the eluent composition was increased to 20% $CH_3CN$ over one min. and the elution was continued with a linear gradient rate of 0.6%/min of $CH_3CN$ (0.1% TFA) into water (0.1% TFA). Fractions (15 mL) were collected using UV (220 nm) as an indicator of product elution. The fractions were analyzed on a reversed phased C18 column (Waters MS C18, 4.6 mm i.d.×50 mm, 5μ particle, 120 Å pore) and the product-containing fractions of >95% purity were pooled and freeze-dried to provide precursor dimer peptide (16) as a colorless, fluffy solid. The remaining crude precursor dimer peptide (16) was purified in the same manner. From 0.5 g each of monomer peptides (12) and (13), 320 mg (overall yield 33%) of the desired dimer (16) was obtained (>95% purity).

Example 5

Preparation of KDR-Binding Dimeric Peptide Phospholipid Conjugate (11) Acetyl-L-alanyl-glycyl-L-prolyl-L-threonyl-L-tryptophyl-L-cystinyl-L-glutamyl-L-aspartyl-L-aspartyl-L-tryptophyl-L-tyrosyl-L-tyrosyl-L- cystinyl-L-tryptophyl-1-leucyl-L-phenylalanyl-glycyl-L-threonyl-glycyl-glycyl-glycyl-L-lysyl[Acetyl-L-valyl-L-cystinyl-L-tryptophyl-L-glutamyl-L-aspartyl-L-seryl-L-tryptophyl-glycyl-glycyl-L-glutamyl-L-valyl-L-cystinyl-L-phenylalanyl-L-arginyl-L-tyrosyl-L-aspartyl-L-prolyl-glycyl-glycyl-glycyl-L- lysyl (distearylphosphoethanolaminocarbonoxy-PEG2000-amino-8-amino-3,6-dioxaoctanoyl-8-amino-3,6-dioxaoctanoyl-glutaryl-L-lysyl) amide cyclic (2-12) disulfide]-amide cyclic (6-13) disulfide; Ac-AGPTWCEDDWYYCWLFGTGGGK {Ac-VCWEDSWGGEVCFRYDPGGGK[-Adoa-Adoa-Glut-K(DSPE-PEG2000-NH-Glut)]-$NH_2$ cyclic (2-12) disulfide}-$NH_2$ cyclic (6-13) disulfide; Ac-Ala-Gly-Pro-Thr-Trp-Cys-Glu-Asp-Asp-Trp-Tyr-Tyr-Cys-Trp-Leu-Phe-Gly-Thr-Gly-Gly-Gly-Lys{Ac-Val-Cys-Trp-Glu-Asp-Ser-Trp-Gly-Gly-Glu-Val-Cys-Phe-Arg-Tyr-Asp-Pro-Gly-Gly-Gly-Lys[-Adoa-Adoa-Glut-Lys(DSPE-PEG2000-NH-Glut)-]-$NH_2$ cyclic (2-12) disulfide}-$NH_2$ cyclic (6-13) disulfide The KDR-binding dimer (11) may be prepared by conjugation of precursor dimer peptide (16), Ac-AGPTWCEDDWYYCWLFGTGGGK[Ac-VCWEDSWGGEVCFRYDPGGGK(-Adoa-Adoa-Glut-K)][-$NH_2$ cyclic (2-12) disulfide]-$NH_2$ cyclic (6-13) disulfide, with DSPE-PEG2000-$NH_2$ phospholipid ammonium salt (18) as shown in FIG. 4.

Solid precursor dimer peptide (16) (0.5 g, 0.092 mmol) was added portionwise to a solution of disuccinimidyl glutarate (DSG, 0.15 g, 0.46 mmol), and diisopropylethylamine (0.06 g, 0.47 mmol) in anhydrous DMF (3.0 mL) with stirring over a period of 3 min. Then the solution was stirred at ambient temperature for 30 min. The reaction mixture was diluted to ~50 mL with anhydrous ethyl acetate; this resulted in precipitation of the dimer glutaric acid monoamide mono-NHS ester (17), the glutaric acid monoamide mono-NHS ester of the precursor dimer peptide (16). The solution was centrifuged to pellet 6 (m/z, neg. ion, 1887.3 (M-3H)/3, 1415.1 (M-4H)/4, 1131.9 (M-5H)/5) as a colorless solid. The supernatant ethyl acetate layer containing excess DSG was decanted from the compacted solid dimer glutaric acid monoamide mono-NHS ester (17) which was again resuspended in ethyl acetate, centrifuged and washed twice more to remove the remaining traces of DSG. The solid intermediate glutaric acid monoamide mono-NHS ester dimer derivative (17) thus obtained was dissolved in anhydrous $DMF/CH_2Cl_2$ (8:2, v/v) (3.0 mL); diisopropylethylamine (0.06 g, 0.47 mmol) was added and the solution was stirred.

Meanwhile, DSPE-PEG2000-$NH_2$ phospholipid ammonium salt (18) (0.235 g, 0.084 mmol, 0.9 eq.) was suspended in dry dichloromethane (2 mL) in a separate flask and TFA (2 drops) was added to protonate the phosphodiester oxygen, facilitating solubilization of phospholipid ammonium salt (18) in dichloromethane. The clear solution was concentrated to remove the volatiles and dried further under vacuum.

The solid phospholipid ammonium salt (18) was dissolved in DMF (2 mL) and transferred to the stirred solution of glutaric acid monoamide mono-NHS ester dimer derivative (17) and the resulting mixture was stirred for 24 h at ambient temperature. The reaction mixture was diluted with a solution of 50% $CH_3OH$, 25% $CH_3CN$ and 25% water (1:1) to ~100 mL and the insolubles were filtered. Half of the filtered solution was loaded onto a reverse phased C4 preparative column (Kromasil® Prep C4, 10μ, 300 Å, 50×250 mm) which had been pre-equilibrated with 1:1 mixture of $CH_3OH$ and $CH_3CN$ (1:1, 0.1% TFA) and water (0.1% TFA) at a flow rate of 100 mL/min. During application of the sample solution to the column the flow of the equilibrating eluent from the preparative HPLC system was stopped. After the sample solution was loaded the flow of the equilibrating eluent was reinitiated and the column was washed until the plug of DMF was eluted.

The composition of the eluent was then ramped to 70% $CH_3OH$—$CH_3CN$ (1:1, 0.1% TFA)-water (0.1% TFA) over 1 min and a linear gradient of 0.75%/min of $CH_3OH$—$CH_3CN$ (1:1, 0.1% TFA) into water (0.1% TFA) was initiated. The elution was continued after reaching 100% B in order to achieve complete elution of the product from the column. Fractions (15 mL) were collected using UV (220 nm) as an indicator of product elution and after the main product was eluted fraction collection was continued for several minutes in order to insure elution of trace amounts of starting phospholipid ammonium salt (18). Fractions were checked for purity on an analytical HPLC system (column: YMC C4, 5 μM, 300 Å, 4.6×250 mm) using UV at 220 nm and an evaporative light scattering detector (ELSD). The latter detector is employed to detect DSPE-PEG2000-$NH_2$ which has a weak chromophore at 220 nm. Product-containing fractions of >98% purity, and devoid of DSPE-PEG2000-$NH_2$ phospholipid ammonium salt (8) were combined and concentrated to reduce the content of $CH_3OH$. The solution was then diluted with 10% $CH_3CN$ in water until a faint flocculent precipitate formed. The resulting solution was freeze-dried to afford the dimeric peptide phospholipid conjugate (11) as a colorless solid. The second portion of crude dimeric peptide phospholipid conjugate (11) was purified as described above. The combined yield of the target dimeric peptide phospholipid conjugate (11) was 0.39 g (57% yield). The samples of the dimeric peptide phospholipid conjugate (11) made from different sample purification runs were pooled together, dissolved in tert-butanol-acetonitrile-water mixture and re-lyophilized to provide the dimeric peptide phospholipid conjugate (11) as a colorless, fluffy solid which was further dried under vacuum.

Examples 6-8 below refer to the preparation of the dimer peptide-phospholipid conjugate shown in FIG. 5, wherein the dimeric conjugate contains very low levels of TFA. FIGS. 6-8 illustrate the methods described in the Examples below.

Example 6

Preparation of Dimeric Conjugate Having Low TFA Levels Via the Use of a Glutaryl Linker Preparation of (23), (26) and Dimer Peptide (27) Acetate Salt by Conversion of (22), (25) and Dimer Peptide 27 ●nTFA Salts to Acetates by AG MP-50 Ion-Exchange Resin For compound (23) an AG MP-50 ion-exchange resin (1.5 meq/mL resin bed) was suspended in 20% of $CH_3CN/H_2O$. The suspension was packed in a 3×30 cm glass column and the final volume was 150 mL. The column was connected to a pump and a conductivity meter. It was washed with 20% of $CH_3CN/H_2O$ at 17 mL/min flow rate until the conductivity was below 1 μs/cm. Compound (22) (210 mg) was dissolved in 20% of $CH_3CN/H_2O$ (80 mL) and the resulting solution was loaded to the column. The column was washed again with the same eluent until its conductivity was below 1 μs/cm. A gradient of $NH_4OAc$ in 20% of $CH_3CN/H_2O$ was applied at 200 mM, 400 mM, 600 mM and 800 mM, 250 mL each. The compound came out at 600 mM $NH_4OAc$. The fractions were analyzed by HPLC and the ones containing the compound were combined and lyophilized several times until the weight of the material was constant. 176 mg of the pure material (23) was obtained as a white fluffy solid. The yield was 83.8%.

Additional parameters and results were as follows: HPLC: Ret. Time: 5.6 min; Assay >98% (area %); Column: Waters XTerra MS-C18, 4.6×50 mm, 5μ particle, 120 Å pore; Eluent: A: $H_2O$ (0.1% TFA), B: $CH_3CN$ (0.1% TFA); Elution: Initial condition: 15% B, linear gradient 15-50% B over 8 min; Flow rate: 3 mL/min; Detection: UV at 220 nm; Mass Spectrum: API-ES; Mode: Negative ion; 1441.7 [M-2H]/2, 960.9 [M-3H]/3. CE analysis (counter-ion % wt./wt.): TFA estimated to be 0.3%; acetate 1.1%.

For compound (26), following the same procedure for compound (23), 300 mg of the peptide TFA salt (25) in 80 mL of water was loaded at 17 mL/min. to a 150 mL of AG MP-50 column, which was washed with $H_2O$ to conductivity of 1 μs/cm. The column was then washed with $H_2O$ again after loading, and the same step gradient of aqueous $NH_4OAc$ into $H_2O$ as employed for the ion exchange of compound (23) was applied. Lyophilization of the combined fractions to a constant weight afforded 200 mg of the acetate (26) as a white fluffy solid. The yield was 66.7%.

Additional parameters and results were as follows: HPLC: Ret. Time: 5.6 min; Assay 97.0% (area %); Column: Waters XTerra MS-C18, 4.6×50 mm, 5μ particle, 120 Å pore; Eluent: A: $H_2O$ (0.1% TFA), B: $CH_3CN$ (0.1% TFA); Elution: Initial condition: 15% B, linear gradient 15-50% B over 8 min; Flow rate: 3 mL/min; Detection: UV at 220 nm; Mass Spectrum: API-ES; Mode: Negative ion; 1336.9 [M-2H]/2, 890.8 [M-3H]/3; CE analysis (counter-ion % wt./wt.): TFA estimated to be 0.4%; acetate 4.2%; IC analysis (F %): 0.26.

For the dimer peptide (27) acetate salt, similar to the procedure for compound (23), an AG MP-50 column (100 mL wet volume) was washed with 30% $CH_3CN/H_2O$ until the conductivity was below 1 μs/cm. Compound (27) as the TFA salt, (120 mg in 80 mL of 30% of $CH_3CN/H_2O$) was loaded onto the column and the column was washed with the same eluent until the conductivity was stable at 1 μs/cm. A step gradient of $NH_4OAc$ 30% of $CH_3CN/H_2O$ into 30% of $CH_3CN/H_2O$ was run as for compound (23) and the compound was eluted at ca 600 mM $NH_4OAc$. The combined fractions were lyophilized and then relyophilized several times until the material displayed a constant weight to provide 104 mg of the pure material (27) as an acetate salt. The yield was 86.7%.

Additional parameters and results were as follows: HPLC: Ret. time: 5.2 min; Assay >99% (area %); Column: Waters XTerra MS-C18, 4.6×50 mm, 5μ particle, 120 Å pore; Eluent: A: $H_2O$ (0.1% TFA), B: $CH_3CN$ (0.1% TFA); Elution: Initial condition: 20% B, linear gradient 20-60% B over 8 min; Flow rate: 3 mL/min; Detection: UV at 220 nm; Mass Spectrum: API-ES; Mode: Negative ion; 1816.3 [M-3H]/3, 1362.0 [M-4H]/4, 1089.2 [M-5H]/5; CE analysis (counter-ion % wt./wt.): TFA estimated to be 0.2%; acetate 0.15%.

Preparation and Purification of the Dimer Peptide (27) Acetate Salt from Compound (23) and Compound (26)

To a solution of disuccinimidyl glutarate (18 mg, 0.055 mmol) in anhydrous DMF (0.1 mL) was added a solution of compound (23) (61 mg, 0.021 mmol) in 0.2 mL of anhydrous DMF dropwise (pH 8, neutralized by DIEA). The clear solution was stirred at RT for 0.5 h. HPLC and MS showed the completion of the reaction. Solvent was removed in vacuo and EtOAc (8 mL) was added to precipitate the intermediate (24). The mixture was centrifuged and decanted to remove excess glutarate. This EtOAc washing was repeated 3 more times and the resulting solid was dried using a stream of dry nitrogen. It was then dissolved in 0.3 mL of anhydrous DMF. Compound (26), (56 mg, 0.021 mmol) was added and the pH of the solution was adjusted to 8 by addition of DIEA. The solution was stirred for 16 h at room temperature after which by HPLC and MS analysis indicated completion of the reaction. A 30 μL aliquot of $NH_2NH_2$ was added and the mixture was stirred for 5 min to cleave the ivDde group. The reaction mixture was analyzed by HPLC and MS, which indicated complete removal of the ivDde group.

Before purification of the dimer peptide (27) acetate, caution was taken to carefully wash the whole preparative HPLC system including the column with TFA-free eluents, $CH_3CN/H_2O/10$ mM $NH_4OAc$. The crude reaction mixture was then applied to a reverse phase C-18 preparative column (Atlantis C-18, 5 μm particle, 100 Å pore, 30×150 mm, flow rate 30 mL/min), pre-equilibrated with 15% B (A: 10 mM $NH_4OAc$ in $H_2O$; B: 10 mM $NH_4OAc$ in $CH_3CN/H_2O$, 9/1, v/v). The column was washed with the same eluent until the DMF plug was eluted. The eluent composition was increased to 25% B over 2 min. and then ramped to 65% B over 40 min. The fractions were analyzed on an analytical reverse phase C-18 column (Waters MS C-18, 4.6×50 mm, 5 μm particle, 100 Å pore, flow rate 3 mL/min) and the product-containing fractions of >95% purity were pooled and freeze-dried to afford 25 mg of the dimer peptide (27) as its acetate salt as a fluffy white solid. The yield was 21.8%.

Additional parameters and results were as follows: HPLC: Ret. time: 5.2 min; Assay >99% (area %); Column: Waters XTerra MS-C18, 4.6×50 mm, 5μ particle, 120 Å pore; Eluent: A: $H_2O$ (0.1% TFA), B: $CH_3CN$ (0.1% TFA); Elution: Initial condition: 20% B, linear gradient 20-60% B over 8 min; Flow rate: 3 mL/min; Detection: UV at 220 nm; Mass Spectrum: API-ES; Mode: Negative ion; [M-3H]/3, 1362.0 [M-4H]/4, 1089.2 [M-5H]/5; CE analysis (counter-ion % wt./wt.): TFA estimated to be less than 0.2%; acetate 1.1%.

Example 7

FIG. 7

Preparation of Dimer Peptide-Phospholipid Conjugates Having Low TFA Levels Via Ion Exchange Resin Preparation and Purification of the Phospholipid Peptide Conjugate (21) as its Acetate Salt from Dimer Peptide (27) Acetate Salt To a solution of disuccinimidyl glutarate-DSG (3.7 mg, 11.3 μmol) in anhydrous DMF (0.1 mL) was added a solution of neutralized dimer peptide (27) acetate salt, (15 mg, 2.75 μmol) in anhydrous DMF (0.2 mL), dropwise. The reaction solution was stirred at RT for 0.5 h. HPLC analysis with a Waters Xterra C-18 column and MS showed the completion of the reaction. The solvent was evaporated and EtOAc (8 mL) was added to precipitate the intermediate (28). The vessel containing the precipitated intermediate (28) was centrifuged and the liquid layer was decanted. This procedure was repeated 3 times to remove the excess of DSG. The solid was dried with a stream of dry nitrogen and then dissolved in 0.3 mL of anhydrous DMF. DSPE-PEG2000-$NH_2$ ammonium salt (29) (6.5 mg, 2.33 µmol) was added in solid form and the pH of the mixture was adjusted to (28). The reaction mixture was stirred at RT for 16 h. The mixture was analyzed by MS and HPLC with a Zorbax 300 SB-C3 column and this indicated that the reaction was complete.

To minimize the potential contamination of the product with TFA, the crude reaction mixture was purified by preparative HPLC equipped using a new Zorbax 300SB-C3 column (21.2×150 mm, 5µ particle) which had never been exposed to TFA. The HPLC system was pre-washed by $CH_3CN/H_2O/NH_4OAc$ extensively to remove traces of TFA. The reaction mixture was loaded onto the column which was pre-equilibrated with 20% B (A: 10 mM $NH_4OAc$ in $H_2O$; B: 10 mM $NH_4OAc$ in $CH_3CN/H_2O$, 9/1 v/v) at a flow rate of 30 mL/min. The column was eluted at 30 mL/min with the same eluent until the plug of DMF was eluted. The eluent composition was then increased to 40% B over 3 min and then ramped to 90% B over 50 min. The collected fractions were analyzed on an analytical reverse phase C-3 column (Zorbax 300SB-C3, 3×150 mm, 3.5 µm particle, 300 Å pore, flow rate: 0.5 mL/min), where detection was accomplished using UV at 220 nm and an evaporative light scattering detector (ELSD). The fractions containing the pure product were pooled and lyophilized. A 6.5 mg portion of the final product (21) acetate salt was obtained. The yield was 33.0%.

Additional parameters and results were as follows: HPLC: Ret. Time: 13.3 min; Assay >99% (area %); Column: Zorbax 300SB-C3, 3×150 mm, 3.5 µm, 300 Å pore; Eluent: A: $H_2O$ (0.1% TFA), B: $CH_3CN$/MeOH 1/1 (0.1% TFA); Elution: Initial condition: 60% B, linear gradient 60-90% B over 3 min; Flow rate: 0.5 mL/min; Detection: UV at 220 nm and ELSD; CE analysis (counter-ion % wt./wt.): % wt. TFA: 0.3%; % wt acetate 0.4%.

Example 8

FIG. 8

Preparation of Dimeric Conjugate Having Low TFA Levels Via Sequential Purification Using Zorbax C-3 RP Preparative HPLC and Sephadex G-25 Gel Permeation Chromatography Materials used and conditions for the analytical HPLC system include the following: Column: Zorbax 300SB C-3; 3 mm i.d.×150 mm; 3.5 µm particle; Eluent A: $H_2O$ (HPLC Grade with 0.1% TFA by volume); Eluent B: $CH_3CN$ (0.1% TFA by volume). Elution: Initial condition: 50% B then a linear gradient of 50-90% B over 3 min, hold at 90% B for 11 min; Flow rate: 0.5 mL/min; Detection: UV at 220 nm. Ret. time: (Compound (21)): 6.77 min, Rt (lyso): 4.06 min.

Preparative HPLC Using Preparative Zorbax C-3 Column to Remove the Lyso-Compound from (21)

The crude compound was loaded at a concentration of 30% eluent B. Materials used and conditions include: Conditions: Column: Waters Zorbax 300SB C-3; 21.2 mm i.d.×150 mm; 3.5 µm particle; Eluents: Eluent A: $H_2O$ (HPLC Grade with 10 mM $NH_4OAc$); Eluent B: $CH_3CN/H_2O$, 9/1 (final $NH_4OAc$ concentration: 10 mM).

The composition of the eluent was then changed to 45% B over 2 min, then the column was eluted with a linear gradient of 45-100% B over 40 min; Flow rate: 30 mL/min; Detection: UV at 220 nm.

The crude compound (100 mg) was dissolved in 25 mL of a solution of 30% B. The preparative HPLC system was equilibrated at 30% B. The compound was loaded on to the Zorbax C-3 column. The mobile phase composition was ramped to 45% B over 2 min. A linear gradient from 45-100% B over 40 min was used for the elution of (21). The product eluted between 26.5-33 min.

The fractions that contained (21) were combined and lyophilized to give a white fluffy solid. This was dissolved in water-acetonitrile, then lyophilized again. This provided 70 mg product devoid of the lyso-compound. The recovery was about 70%. After chromatography was completed, the system was washed with 95% B for 15 min at a flow rate of 30 mL/min. The column was then washed with $CH_3CN/H_2O$ (50/50, without TFA or buffer) for 30 min at a flow rate of 15 mL/min. The column was then stored at room temperature for future use. Analytical HPLC confirmed the absence of the lyso-compound in the isolated material. Further analysis confirmed that no lyso-compound formed after 5 days at room temperature. The material still contained significant amounts (4.2 wt %) of TFA.

Removal of TFA from (21) by Gel Permeation Chromatography on Sephadex G-25

A Sephadex G-25 column (100 g resin, bead size 20-80 µm, total gel volume ~500 mL, column height: 27 cm) was equilibrated with 4 L of 50 mM ammonium bicarbonate. Then (21) (70 mg) was dissolved in 30 mL (final volume) of 60 mM ammonium bicarbonate in 10% aqueous acetonitrile. The solution was filtered and then loaded on to the Sephadex G-25 column. The column was eluted with 50 mM ammonium bicarbonate buffer with collection of 10 mL fractions. The collected fractions were monitored by analytical HPLC (UV detection at 220 nm). The results are provided in Table 4 below.

TABLE 4

| Fraction # | Volume (mL) | Compound present (by HPLC analysis of fraction) |
|---|---|---|
| 1 | 10 | No |
| 3 | 10 | No |
| 6 | 10 | No |
| 9 | 10 | No |
| 12 | 10 | No |
| 15 | 10 | No |
| 18 | 10 | No |
| 19 | 10 | No |
| 20 | 10 | Yes |
| 21 | 10 | Yes |
| 24 | 10 | Yes |
| 27 | 10 | Yes |
| 28 | 10 | Yes |
| 29 | 10 | No |

Fractions 20-28 were pooled and lyophilized. The lyophilized material obtained was re-dissolved in a small volume of water and the solution was frozen and lyophilized to remove residual amounts of ammonium bicarbonate. The final weight of the desired material was 58 mg. The recovery was 83%.

To ascertain the effective removal of TFA, the sample was subjected to CE analysis for TFA and acetate ions. The TFA is clearly present in the starting material (4.2%) according to the previous assay, while it is hardly detected (0.2%) after the gel permeation procedure. No acetate ion was detected.

Analytical Data for (21) Obtained by Serial Zorbax C-3 Preparative HPLC and Sephadex G-25 Gel Permeation Chromatography Materials used and conditions for collecting analytical data include: Fluorine analysis (IC by QTI): 751 ppm (0.15% TFA wt/wt); Mass Spectrum: Method: MALDI-TOF; Mode: Positive Ion; Average molecular weight detected was 8461 the typical PEG2000 mass distribution curve was observed. HPLC: System A: Column: Zorbax 300SB C-3; 3 mm i.d.× 150 mm; 3.5 µm particle; Eluent A: Water (HPLC Grade with 0.1% TFA by volume); Eluent B: Acetonitrile (0.1% TFA by volume). Initial condition: 50% B; Elution: linear gradient of 50-90% B over 3 min, hold at 90% B for 11 min; Flow rate: 0.5 mL/min; Detection: UV at 220 nm. Ret time: 6.77 min; Area %: 99.6%. System B: Column: Zorbax 300SB C-3; 3 mm i.d.×150 mm; 3.5 µm particle; Eluent A: Water (HPLC Grade with 0.1% TFA by volume); Eluent B: Acetonitrile (0.1% TFA by volume). Initial condition: 50% B; Elution: linear gradient of 50-90% B over 3 min then ramp to 100% B over 12 min. Flow rate: 0.5 mL/min; Detection: LSD; Ret: time: 13.98 min. Area %: 99.3%.

Table 5 below provides definitions for the abbreviations used and the sources of materials referred to in Examples 9-12.

TABLE 5

| | |
|---|---|
| DSPA.Na | (Genzyme) IUPAC: 1,2-Distearoyl-sn-glycero-3-phosphosphatidic acid, sodium salt |
| DPPG.Na | (Genzyme) IUPAC: 1,2-Dipalmitoyl-sn-glycero-3-phosphoglycerol, sodium salt |
| DPPE | (Genzyme) IUPAC: 1,2-Dipalmitoyl-sn-glycero-3-phosphoethanolamine |
| DSPC | Distearoyl-glycero-phosphatidylcholine (Genzyme) IUPAC: 1,2-Distearoyl-sn-glycero-3-phosphocholine |
| DSPG.Na | (Genzyme) IUPAC: 1,2-Distearoyl-sn-glycero-3-phosphoglycerol, sodium salt |
| DSPE-PEG1000 | Distearoyl-glycero-phosphoethanolamine-N-methoxy(polyethylene glycol)1000 (Avanti Polar) |
| DSPE-PEG2000 | Distearoyl-glycero-phosphoethanolamine-N-methoxy(polyethylene glycol)2000 (Avanti Polar) |
| Stearate* | Sodium Stearate (Fluka) |
| PEG4000 | (polyethylene glycol) MW 4000 (Fluka) |
| Mannitol | (Fluka) |

*the acid form, i.e., stearic acid, can also be used in any of the microbubble preparations herein.

Example 9

Preparation of Targeted Microbubbles with DSPC/DPPG Envelope

Example 9A 383 mg of a mixture of DSPC/DPPG/and the dimeric peptide phospholipid conjugate (11) shown in FIG. 5 (molar ratio 49.75/49.75/0.5, corresponding to 187.1, 176.4 and 19.8 mg of the three components, respectively) and PEG-4000 (22.6 g) were solubilized in 120 g of t-butyl alcohol at 60° C., in a water bath. The solution was filled in vials with 0.8 mL of solution each. The samples were frozen at −45° C. and lyophilized. The air in the headspace was replaced with a mixture of $C_4F_{10}$/Nitrogen (50/50) and vials capped and crimped. The lyophilized samples were reconstituted with 5 mL of $H_2O$ per vial.

Example 9B

Example 9A was repeated using a mixture of DSPC/DPPG/and the monomeric peptide phospholipid conjugate (31) shown in FIG. 10 (molar ratio 49.5/49.5/1, corresponding to 182.8, 172.3 and 28.2 mg of the three components, respectively)

Example 10

Preparation of Targeted Microbubbles with DPPE/DPPG Envelope

Example 10A

An aqueous suspension of DSPE-PEG1000 (0.43 mg-0.24 µmole) and the monomeric peptide phospholipid conjugate (31) shown in FIG. 10 (3.0 mg-0.5 µmole) was prepared in 500 µL of distilled water at 60° C. to obtain a micellar suspension.

Separately, DPPE (15.8 mg-22.8 µmoles) and DPPG (4.2 mg-5.7 µmoles) were dispersed in a solution of mannitol 10% in distilled water (20 mL) at 70° C. for 20 minutes. The dispersion was then cooled to room temperature. Perfluoroheptane (1.6 mL) was emulsified in the aqueous phase using a high speed homogenizer (Polytron PT3000, probe diameter of 3 cm) for 1 minute at 10500 rpm to obtain an emulsion.

The micellar suspension was added to the emulsion and the resulting mixture was heated at 60° C. for 1 hour under stirring. After cooling to room temperature (1 hour), the obtained emulsion was divided in 4 mL fractions in 50 mL round bottom flasks. The emulsion was frozen at −45° C. for 5 minutes and freeze-dried at 0.2 mBar for 24 hours (Freeze-Drier Christ Beta 1-8K).

Before redispersion, the lyophilisate was exposed to an atmosphere containing C4F10/nitrogen (50/50 by volume). The lyophilized product was then dispersed in a volume of water twice the initial one by gentle hand shaking.

Example 10B

An aqueous suspension of DSPE-PEG1000 (0.5 mg-0.27 µmole) and dimeric peptidephospholipid conjugate (11) shown in FIG. 5 (5.3 mg-0.63 µmole) was prepared in 500 µL of distilled water at 60° C. to obtain a micellar suspension.

Separately, DPPE (15.8 mg-22.8 µmoles) and DPPG (4.2 mg-5.7 µmoles) were dispersed in a solution of PEG4000 10% in distilled water (20 mL) at 70° C. for 20 minutes. The dispersion was then cooled to room temperature. Perfluoroheptane (1.6 mL) was emulsified in the aqueous phase using a high speed homogenizer (Polytron PT3000, probe diameter of 3 cm) for 1 minute at 10000 rpm to obtain an emulsion.

The micellar suspension was added to the emulsion and the resulting mixture was heated at 80° C. for 1 hour under stirring. After cooling to room temperature (1 hour), the obtained emulsion was washed once by centrifugation (200 g/10 min—Sigma centrifuge 3K10) to eliminate the excess of phospholipid. The separated pellet (containing emulsified microdroplets of solvent) was recovered and re-suspended with the initial volume of a 10% PEG4000 aqueous solution.

The obtained emulsion was sampled into DIN8R vials (1 mL/vial). Then vials were cooled at −50° C. (Christ Epsilon 2-12DS Freeze Dryer) and freeze-dried at −25° C. and 0.2 mBar for 12 hours with a final drying step at 30° C. and 0.1 mBar for 7 hours.

Vials were exposed to an atmosphere containing C4F10/nitrogen (35/65 by volume) and sealed. The lyophilized product was redispersed in a volume of water twice the initial one by gentle hand shaking.

Example 11

Preparation of Targeted Microbubbles with DSPC/DSPA Envelope

Example 11A

An aqueous suspension of DSPE-PEG1000 (2.5 mg-1.4 µmole) and dimeric peptide conjugate (11) shown in FIG. 5 (7.0 mg-0.84 µmole) was prepared in 1 mL of distilled water at 60° C. to obtain a micellar suspension.

Separately, DSPC (16.3 mg-20.6 µmoles) and DSPA (3.7 mg-5.15 µmoles) were dissolved in cyclooctane (1.6 mL) at 80° C. This organic phase was added to a PEG4000 10% solution in water (20 mL) using a high speed homogenizer (Polytron T3000, probe diameter of 3 cm) for 1 minute at 8000 rpm, to obtain an emulsion.

The micellar suspension was mixed with the emulsion and the resulting mixture was heated at 80° C. for 1 hour under agitation. After cooling to room temperature (1 hour), the obtained emulsion was washed once by centrifugation (1500 g/10 min—Sigma centrifuge 3K10) to eliminate the excess of the phospholipid. The separated supernatant (containing emulsified microdroplets of solvent) was recovered and re-suspended in twice the initial volume of a 10% PEG 4000 aqueous solution.

The obtained suspension was sampled into DIN8R vials (1 mL/vial). Then vials were cooled to −50° C. (Christ Epsilon 2-12DS Freeze Dryer) and freeze-dried at −25° C. and 0.2 mbar for 12 hours, with a final drying step at 30° C. and 0.1 mbar for 7 hours.

Vials were exposed to an atmosphere containing $C_4F_{10}$/Nitrogen (35/65 by volume) and sealed. The lyophilized product was then dispersed in a volume of water twice the initial one by gentle hand shaking.

Example 11B

Example 11A was repeated, but using 0.7 mg of DSPE-PEG2000 (0.26 µmoles) and 1.6 mg of monomeric peptide-phospholipid conjugate (1) shown in FIG. 2 (0.26 µmole) to prepare the micellar suspension.

Example 11C

DSPC (16.3 mg-20.6 µmoles), DSPA (3.7 mg-5.15 µmoles) and monomeric peptide phospholipid conjugate (1) shown in FIG. 1 (1.6 mg-0.26 µmole) were dissolved in cyclooctane (1.6 mL) at 80° C. This organic phase was emulsified in a PEG4000 10% aqueous phase (20 mL) using a high speed homogenizer (Polytron PT3000, probe diameter of 3 cm) for 1 minute at 8000 rpm to obtain an emulsion.

The resulting emulsion was heated at 80° C. for 1 hour under stirring. After cooling to room temperature (1 hour), the obtained emulsion was diluted with 20 ml of a PEG4000 10% aqueous solution.

The emulsion was sampled into DIN8R vials (1 mL/vial). Then vials were cooled at −50° C. (Christ Epsilon 2-12DS Freeze Dryer) and freeze-dried at −25° C. and 0.2 mBar for 12 hours with a final drying step at 30° C. and 0.1 mBar for 7 hours.

Vials were exposed to an atmosphere containing C4F10/nitrogen (35/65 by volume) and sealed. The lyophilized product was redispersed in a volume of water twice the initial one by gentle hand shaking.

Example 12

Preparation of Targeted Microbubbles with DSPC/Stearate Envelope

Example 12A

An aqueous suspension of DSPE-PEG2000 (2.5 mg-0.9 µmoles) and the dimeric phospholipid conjugate (11) shown in FIG. 5 (2.5 mg-0.3 µmoles) was prepared in 660 µL of distilled water at 60° C. to obtain the micellar suspension.

Separately, DSPC (18.2 mg-23.1 µmoles) and stearate (1.8 mg-5.8 µmoles) were dissolved in cyclooctane (1.6 mL) at 80° C. This organic phase was added to a PEG4000 10% solution in water (20 mL) using a high speed homogenizer (Polytron T3000, probe diameter of 3 cm) for 1 minute at 9000 rpm, to obtain an emulsion.

The micellar solution was mixed with the emulsion and the resulting mixture was heated at 80° C. for 1 hour under agitation. After cooling to room temperature (1 hour), the obtained emulsion was washed once by centrifugation (1500 g/10 min—Sigma centrifuge 3K10) to eliminate the excess of phospholipids. The separated supernatant (containing emulsified microdroplets of solvent) was recovered and re-suspended with twice the initial volume of a 10% PEG 4000 aqueous solution.

The obtained suspension was sampled into DIN8R vials (1 mL/vial). Then vials were cooled to −50° C. (Christ Epsilon 2-12DS Freeze Dryer) and freeze-dried at −25° C. and 0.2 mbar for 12 hours, with a final drying step at 30° C. and 0.1 mbar for 7 hours.

Vials were exposed to an atmosphere containing $C_4F_{10}$/Nitrogen (35/65 by volume) and sealed. The lyophilized product was dispersed in a volume of water twice the initial one by gentle hand shaking.

Example 12B

Example 12A was repeated by replacing the dimeric peptide phospholipid conjugate (11) shown in FIG. 5 with the same relative molar amount of the monomeric peptide phospholipid conjugate (1) shown in FIG. 2.

Example 12C

Example 11C was repeated with DSPC (18.2 mg-23.1 µmoles), sodium stearate (1.8 mg-5.8 µmoles) and the dimeric peptide phospholipid conjugate (11) shown in FIG. 5 (2.2 mg-0.26 µmole). The agitation speed for emulsification was fixed to 9000 rpm. After cooling to room temperature (1 hour), the obtained emulsion was washed once by centrifugation (1500 g/10 min—Sigma centrifuge 3K10) to eliminate the excess of the phospholipid. The separated supernatant (containing emulsified microdroplets of solvent) was recovered and re-suspended in twice the initial volume of a 10% PEG 4000 aqueous solution.

Example 13

Static Binding Test on KDR-Transfected Cells

Plasmid Production and Purification

Full-length KDR was cloned into the pcDNA6 vector and the plasmid was amplified in competent DH5α *E. coli*. Plasmid amplification and purification was performed using *E. coli* JM 109 and a kit from Quiagen.

Transfection of 293H Cells on Thermanox® Coverslips

Cells were grown on poly-D-lysine-coated Thermanox® circular coverslips in 24-well plate. Transfection was done as recommended in the lipofectamine 2000 protocol (Invitrogen, cat#11668-019) using 1 μg of DNA (pc-DNA6-fKDR)/per coverslip (1.3 cm2) in 0.1 mL. Transfection was done in serum-free media, the transfection reagent mix was removed from cells after 2 hours and replaced with regular serum-containing medium. Some of the cell-coated coverslips were mock-transfected (with no DNA). The next day, expression of the KDR receptor was assessed by immunocytochemistry and the binding assay was performed.

Bubble Binding Assay

The transfected cells were incubated with KDR-targeted microbubbles resuspended in 50% human plasma in PBS. For the incubation with the transfected cells a small plastic cap was filled with a suspension containing a $1.3 \times 10^8$ bubbles and the cap was covered with an inverted Thermanox® coverslip so as to put the transfected cells in contact with the targeted microbubbles. After 30 min of incubation at RT, the coverslip was lifted with tweezers, rinsed three times in PBS and examined under a microscope to assess binding of the targeted microbubbles.

Determination of the % of Surface Covered by Microbubbles

Images were acquired with a digital camera DC300F (Leica) and the percent of surface covered by bound microbubbles in the imaged area was determined using the software QWin version 3.1 (Leica Microsystem AG, Basel, Switzerland). Pictures were taken of each Thermanox®coverslip. For each preparation of Examples 9 and 10, the binding assay was repeated a minimum of two times thus obtaining an average value of the surface covered. In the following Tables 6 and 7, the binding activity of the microbubbles prepared according to Examples 9 and 10 above are recorded.

As indicated by the Tables, the same peptide may show different binding activities when included (as a lipopeptide) in different phospholipid formulations forming the stabilizing envelope of the microbubble. Microbubbles containing KDR binding lipopeptides of the invention bind specifically to KDR-expressing cells while they did not bind appreciably to mock transfected cells.

Example 14

Dynamic Binding Test on Rh VEGF-R2/Fc Chimeric Protein

Preparation of Fc-VEGF-R2-Coated Coverslips

Glass coverslips (40 mm in diameter, Bioptechs Inc., Butler, Pa., USA) were coated with recombinant human VEGF-R2/Fc Chimeric protein (R&D Systems) according the following methodology.

A surface of dimensions 14×25 mm was delimited on the glass coverslip using a special marker (Dako Pen) and 400 μL of Fc-VEGF-R2 solution at 4 μg/mL in PBS was deposited on this surface. After an overnight incubation at 4° C., the solution was aspirated, replaced by 0.5 mL of a solution of BSA 1% w/v in PBS-0.05% Tween 80, pH 7.4 and incubated for 3 hours at RT. Then the coverslip was washed three times with 5 ml of PBS-0.05% Tween 80.

Binding Assay

Binding studies of targeted bubbles were carried out using a parallel-plate flow chamber (FCS2, Bioptech Inc., Butler, Pa., USA) with a chamber gasket of 0.25 mm in thickness, with a customized adapter for upside-down chamber inversion. The coated coverslip was inserted as a plate of the flow chamber. Microbubbles ($5 \times 10^6$ bubbles/mL in 50% human plasma in PBS) were drawn through the flow chamber using an adjustable infusion pump (Auto Syringe® AS50 Infusion Pump, Baxter, Deerfield, Ill., USA) with a 60 mL syringe (Terumo). The pump flow rate was adjusted to 1 mL/min to obtain the desired shear rate of about 114 $s^{-1}$. After 10 minutes, the flow was stopped and pictures were taken randomly at different positions on the coverslip (on areas of about 0.025 $mm^2$) using a 40× objective and a CCD monochrome camera (F-View II, Soft Imaging Systems, Germany) connected to an inverted Olympus IX 50 microscope.

The number of microbubbles on each picture was determined, averaged with respect to the total number of pictures and the obtained value was then divided by ten (to obtain the "slope", i.e. the average amount of bound microbubbles per minute).

For each preparation of Examples 11 and 12, the binding assay was repeated four times thus obtaining an average value of the slope.

The slope represents the bubble binding rate on the target substrate. For instance, a slope value of 8 indicates that an average of eighty (80) microbubbles was bound on the coated coverslip in ten minutes. A higher slope indicates a better capacity of bubbles to bind to the target under flow conditions.

In the following tables 8 and 9, the binding activity of the microbubbles prepared according to Examples 11 and 12 above were illustrated.

As inferable from the tables, the same peptide may show different binding activities when included (as a peptide-phospholipid conjugate or lipopeptide) in different phospholipid formulations forming the stabilizing envelope of the microbubble.

TABLE 6

| Example | KDR | Mock | KDR-Mock |
|---|---|---|---|
| 9A | 28.6% | 0.4% | 28.3% |
| 9B | 28.0% | 0.3% | 27.7% |

TABLE 7

| Example | KDR | Mock | KDR-Mock |
|---|---|---|---|
| 10A | 23.6% | 0.2% | 23.5% |
| 10B | 28.0% | 0.0% | 28.0% |

TABLE 8

| Example | Slope |
|---|---|
| 11A | 8.2 |
| 11B | 8.1 |
| 11C | 5.8 |

TABLE 9

| Example | Slope |
|---|---|
| 12A | 9.0 |
| 12B | 8.0 |
| 12C | 7.8 |

Example 15

In Vivo Evaluation of Ultrasound Contrast Agents Targeted to KDR

The ability of ultrasound contrast agents containing KDR binding lipopeptides of the invention to bind to KDR-expressing tissue in vivo was assessed using a known model of angiogenesis: the rabbit VX2 tumor model.

A known model of angiogenic tissue was used to examine the ability of the KDR-targeted ultrasound microbubbles to localize to and provide an image of angiogenic tissue. The VX2 rabbit carcinoma was serially implanted in the dorsal muscle of New Zealand rabbits (Charles River Laboratories, France) weighting 2.5/3 kg.

Preparation of Tumor Homogenate

Tumor was surgically removed, placed into McCoy's culture medium containing 10% fetal calf serum, antibiotics, 1.5 mM Glutamax I and cut into small pieces that were rinsed to remove blood and debris. Then tumor pieces (3 to 5 cm$^3$) were placed in a 50 ml Falcon tube containing 5 mL of complete medium. The tumor tissue was ground (Polytron) until no more solid pieces were visible. The murky fluid was centrifuged for 5 minutes at 300 g and the supernatant discarded. Seven mL of fresh medium was added per 5 mL of pellet.

Tumor Implantation

Rabbits received first 0.3 mL of Vetranquil (Acepromazine, Sanofi, injected intramuscularly) and were then anesthetized with an intramuscular injection of Ketaminol®5/Xylazine (Veterinaria AG/Sigma) mixture (50/10 mg/mL, 0.7 mL/kg). One hundred microliters of VX2 tumor homogenate was injected intramuscularly. Fifteen days after implantation of VX2 tumors, animals were anesthetized again with the same mixture, plus subcutaneous injection of 50% Urethane (2 mL/kg, s.c.) (Sigma) for imaging experiments.

In Vivo Ultrasound Imaging

VX2 tumor imaging was performed using an ultrasound imaging system ATL HDI 5000 apparatus equipped with a L7-4 linear probe. B-mode pulse inversion at high acoustic power (MI=0.9) was used to evaluate accumulation of targeted microbubbles on the KDR receptor expressed on the endothelium of neovessels. The linear probe was fixed on the skin directly over the implanted tumors.

After bubble injection (0.1 µL/kg of gas) using the preparations of either Example 16 or Example 17, insonation was stopped allowing bubbles to accumulate for 25 minutes. Then, insonation was reactivated at high acoustic power (MI 0.9) destroying all the bubbles present in the tumor. The amount of free circulating bubbles was then assessed by recording the signal obtained after 20 sec accumulation without insonation.

Figure 11A:
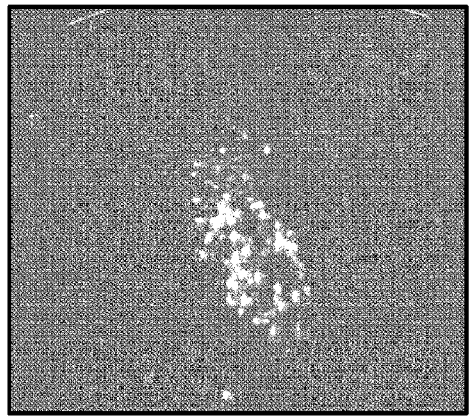
FIGS. 11A-C show images obtained by using the dimer peptide-phospholipid conjugate (11) (shown in FIG. 52) in a contrast agent at: 1) baseline (FIG. 11A); 2) after 25 minutes (FIG. 11B); and 3) after subtraction of the baseline and free circulating bubbles (FIG. 11C).
Figure 11B:
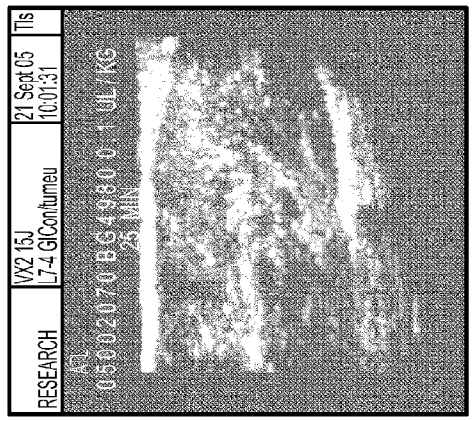
Figure 11C:
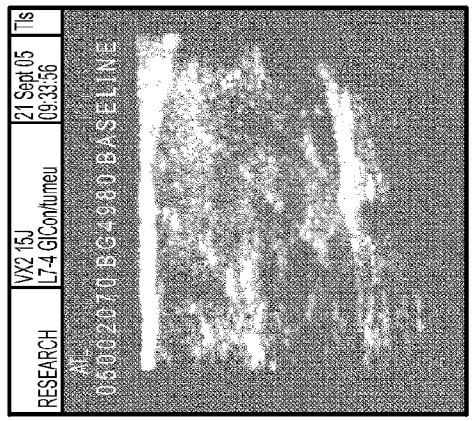
Figure 12A:
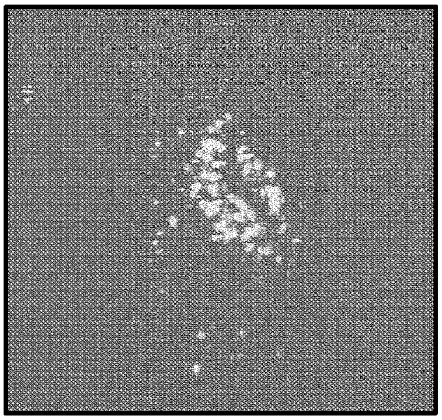
FIGS. 12A-C show images obtained by using the monomeric phospholipid peptide conjugate (1) (shown in FIG. 2) in a contrast agent at baseline (FIG. 12A); after 25 minutes (FIG. 12B); and after subtraction of the baseline and free circulating bubbles (FIG. 12C).
Figure 12B:
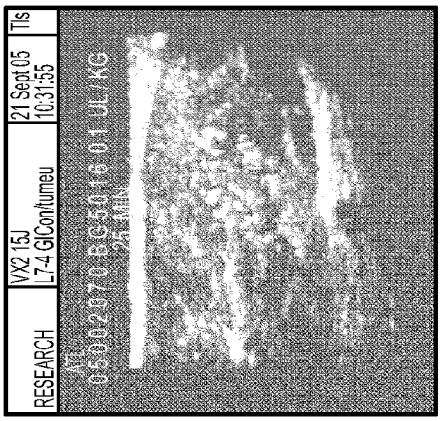
Figure 12C:
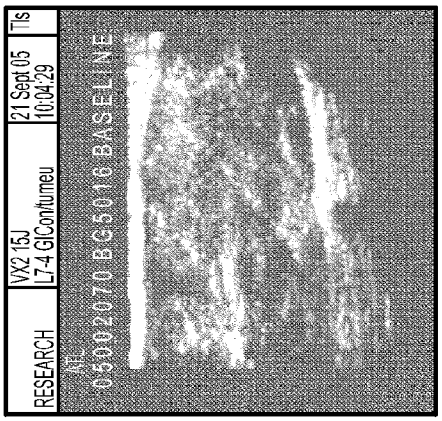

Video frames from VX2 tumor imaging experiments were captured with video-capture and analysed with Image-Pro Plus 2.0 software. The image representing free circulating bubbles was subtracted from the image obtained at 25 min, to provide an image representing bound bubbles. Referring to FIG. 11 (which shows the results with the preparation of Example 16) and FIG. 12 (which shows the results with the preparation of Example 17), FIGS. 11A and 12A show an image before bubble injection (baseline); FIGS. 11B and 12B show retention of bubble contrast in the tumor 25 minutes post injection; and FIGS. 11C and 12C show the result obtained after subtraction of the baseline and free circulating bubbles and represent bound microbubbles containing KDR lipopeptides according to the present invention. Examples 15-17 and FIGS. 11 and 12 confirm that ultrasound contrast agents bearing such KDR binding moieties localize to KDR expressing (and thus angiogenic) tissue in animal models.

Example 16

Example 12A was repeated by replacing DSPE-PEG2000 with DSPE-PEG1000 (2.7 mg, 1.54 µmol) and using 2.5 mg (0.31 µmol) of dimeric peptide phospholipid conjugate (11) shown in FIG. 5.

Example 17

Example 16 was repeated by replacing the dimeric peptide phospholipid conjugate with the same molar amount of monomeric phospholipid conjugate (1) shown in FIG. 2.

---

What is claimed is:

1. A method of making a peptide phospholipid conjugate having less than or equal to 0.3% trifluoroacetic acid (TFA) comprising the steps of:
   converting a peptide TFA salt to an acetate salt via anion exchange; and
   conjugating the peptide to a phospholipid, wherein said phospholipid at the time of conjugation is not included in a gas-filled ultrasound contrast agent.

2. The method of claim 1, wherein the peptide comprises a peptide dimer.

3. The method of claim 1, wherein the peptide dimer comprises Ac-AGPTWCEDDWYYCWLFGTGGGK[Ac-VCWEDSWGGEVCFRYDPGGGK(-Adoa-Adoa-Glut-K)-NH₂ cyclic (2-12) disulfide]-NH₂ cyclic (6-13) disulfide.

4. The method of claim 1, wherein the anion exchange chromatography comprises a step gradient of ammonium acetate.

5. The method of claim 1, wherein the phospholipid is pegylated.

6. The method of claim 1, wherein the pegylated phospholipid is DSPE-PEG2000-NH₂.

* * * * *